US007179301B2

(12) United States Patent  
Vidal et al.

(10) Patent No.: US 7,179,301 B2
(45) Date of Patent: Feb. 20, 2007

(54) DYEING COMPOSITIONS FOR KERATINOUS FIBERS CONTAINING PARAPHENYLENEDIAMINE DERIVATIVES WITH PYRROLIDINYL GROUP

(75) Inventors: Laurent Vidal, Paris (FR); Eric Terranova, Magagnosc (FR); Stéphane Sabelle, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/959,913

(22) PCT Filed: Mar. 13, 2001

(86) PCT No.: PCT/FR01/00745

§ 371 (c)(1),
(2), (4) Date: Apr. 9, 2002

(87) PCT Pub. No.: WO01/68043

PCT Pub. Date: Sep. 20, 2001

(65) Prior Publication Data

US 2003/0093866 A1 May 22, 2003

(30) Foreign Application Priority Data

Mar. 14, 2000 (FR) .................................. 00 03250

(51) Int. Cl.
*A61K 7/13* (2006.01)
(52) U.S. Cl. ................... 8/405; 8/406; 8/408; 8/410; 8/411; 8/412; 8/421; 8/463; 514/408
(58) Field of Classification Search .............. 8/405, 8/406, 408, 410, 411, 412, 421, 463; 514/408
See application file for complete search history.

(56) References Cited

U.S. PATENT DOCUMENTS

| 2,261,002 | A | 10/1941 | Ritter | 260/570 |
|---|---|---|---|---|
| 2,271,378 | A | 1/1942 | Searle | 167/22 |
| 2,273,780 | A | 2/1942 | Dittmar | 260/28 |
| 2,375,853 | A | 5/1945 | Kirby et al. | 260/583 |
| 2,388,614 | A | 11/1945 | Kirby et al. | 167/22 |
| 2,454,547 | A | 11/1948 | Bock et al. | 260/567.6 |
| 3,061,432 | A | 10/1962 | Menzel et al. | 96/55 |
| 3,206,462 | A | 9/1965 | McCarty | 260/256.4 |
| 3,227,554 | A | 1/1966 | Barr et al. | 96/55 |
| 3,419,391 | A | 12/1968 | Young | 96/56.5 |
| 3,725,067 | A | 4/1973 | Bailey et al. | 96/56.5 |
| 3,758,309 | A | 9/1973 | Bailey et al. | 96/136 |
| 3,874,870 | A | 4/1975 | Green et al. | 71/67 |
| 3,915,921 | A | 10/1975 | Schlatzer, Jr. | 260/17.4 |
| 3,926,631 | A | 12/1975 | Arai et al. | 96/29 |
| 3,929,990 | A | 12/1975 | Green et al. | 424/78 |
| 3,966,904 | A | 6/1976 | Green et al. | 424/78 |
| 4,001,432 | A | 1/1977 | Green et al. | 424/329 |
| 4,003,699 | A | 1/1977 | Rose et al. | 8/10.2 |
| 4,005,193 | A | 1/1977 | Green et al. | 424/168 |
| 4,025,617 | A | 5/1977 | Green et al. | 424/78 |
| 4,025,627 | A | 5/1977 | Green et al. | 424/248.4 |
| 4,025,653 | A | 5/1977 | Green et al. | 424/325 |
| 4,026,945 | A | 5/1977 | Green et al. | 260/567.6 |
| 4,027,020 | A | 5/1977 | Green et al. | 424/248.96 |
| 4,128,425 | A | 12/1978 | Greenwald | 96/66 |
| 4,157,388 | A | 6/1979 | Christiansen | 424/70 |
| 4,349,532 | A | 9/1982 | Vanlerberghe et al. | 424/47 |
| 4,390,689 | A | 6/1983 | Jacquet et al. | 528/335 |
| 4,500,548 | A | 2/1985 | Silva | 426/19 |
| 4,500,630 | A | 2/1985 | Sato et al. | 426/19 |
| 4,509,949 | A | 4/1985 | Huang et al. | 586/558 |
| 4,540,654 | A | 9/1985 | Sato et al. | 430/381 |
| 4,608,250 | A | 8/1986 | Jacquet et al. | 424/71 |
| 4,621,046 | A | 11/1986 | Sato et al. | 430/381 |
| 4,698,065 | A | 10/1987 | Hoeffkes et al. | 8/406 |
| 4,702,906 | A | 10/1987 | Jacquet et al. | 424/70 |
| 4,719,282 | A | 1/1988 | Nadolsky et al. | 528/310 |
| 4,823,985 | A | 4/1989 | Grollier et al. | 222/1 |
| 4,842,849 | A * | 6/1989 | Grollier et al. | 424/70.13 |
| 4,996,059 | A | 2/1991 | Grollier et al. | 424/71 |
| 5,061,289 | A | 10/1991 | Clausen et al. | 8/405 |
| 5,135,543 | A | 8/1992 | Chan et al. | 81/406 |
| 5,196,189 | A | 3/1993 | Jacquet et al. | 424/72 |
| 5,249,740 | A | 10/1993 | Serra Tosio et al. | 236/44 |
| 5,256,526 | A | 10/1993 | Suzuki et al. | 430/384 |
| 5,278,034 | A | 1/1994 | Ohki et al. | 430/440 |
| 5,279,619 | A | 1/1994 | Cotteret et al. | 8/406 |

(Continued)

FOREIGN PATENT DOCUMENTS

DE 23 59 399 6/1975

(Continued)

OTHER PUBLICATIONS

Joseph Bailey, "Synthesis of 1*H*-Pyrazolo[3,2-c]-s-Triazoles and Derived Azamethine Dyes", Journal of The Chemical Society, pp. 2047-2052, 1977.

(Continued)

*Primary Examiner*—Eisa Elhilo
(74) *Attorney, Agent, or Firm*—Finnegan, Henderson, Farabow, Garrett & Dunner, L.L.P.

(57) ABSTRACT

The invention concerns novel dyeing compositions for keratinous fibers comprising at least a paraphenylenediamine derivative with pyrrolidinyl group as oxidation base, a dyeing method and a dyeing kit using said composition.

94 Claims, No Drawings

U.S. PATENT DOCUMENTS

| | | | |
|---|---|---|---|
| 5,344,463 A | 9/1994 | Chan et al. | 8/408 |
| 5,380,340 A | 1/1995 | Neunhoeffer et al. | 8/409 |
| 5,430,159 A | 7/1995 | Neunhoeffer et al. | 548/371 |
| 5,441,863 A | 8/1995 | Tang et al. | 430/558 |
| 5,457,210 A | 10/1995 | Kim et al. | 548/262.4 |
| 5,494,490 A | 2/1996 | Audousset et al. | 8/409 |
| 5,538,516 A | 7/1996 | Audousset et al. | 8/412 |
| 5,567,421 A | 10/1996 | Cotteret et al. | 424/70.1 |
| 5,690,696 A | 11/1997 | Bone et al. | 8/411 |
| 5,707,786 A | 1/1998 | Schmuck et al. | 430/373 |
| 5,708,151 A | 1/1998 | Möckli | 534/608 |
| 5,735,908 A * | 4/1998 | Cotteret et al. | 8/410 |
| 5,766,576 A | 6/1998 | Löwe et al. | 424/62 |
| 5,769,903 A * | 6/1998 | Audousset et al. | 8/409 |
| 5,785,717 A * | 7/1998 | Maubru et al. | 8/409 |
| 5,851,237 A | 12/1998 | Anderson et al. | 8/409 |
| 5,863,300 A | 1/1999 | Audousset et al. | 8/411 |
| 5,876,464 A | 3/1999 | Lim et al. | 8/409 |
| 5,993,491 A * | 11/1999 | Lim et al. | 8/409 |
| 6,042,620 A | 3/2000 | Braun et al. | 8/410 |
| 6,099,592 A | 8/2000 | Vidal et al. | 8/409 |
| 6,099,593 A | 8/2000 | Terranova et al. | 8/409 |
| 6,132,475 A | 10/2000 | Chassot et al. | 8/409 |
| 6,165,230 A | 12/2000 | Rose et al. | 8/408 |
| 6,379,396 B1 | 4/2002 | Audousset | 8/407 |
| 6,461,391 B1 | 10/2002 | Lim et al. | 8/405 |
| 6,464,731 B1 | 10/2002 | Genet et al. | 8/405 |
| 6,500,213 B1 | 12/2002 | Braun et al. | 8/405 |
| 6,521,761 B2 | 2/2003 | Lim et al. | 548/557 |
| 6,565,614 B1 | 5/2003 | Genet et al. | 8/406 |
| 6,613,313 B2 * | 9/2003 | Kimura | 424/70.1 |
| 6,638,321 B1 | 10/2003 | Genet et al. | 8/407 |
| 6,673,124 B2 | 1/2004 | Laurent et al. | 8/406 |
| 2002/0197223 A1 | 12/2002 | Kimura | 424/70.1 |
| 2003/0093866 A1 | 5/2003 | Vidal et al. | 8/405 |
| 2003/0150066 A1 | 8/2003 | Richard | 8/405 |
| 2004/0064902 A1 | 4/2004 | Sabelle et al. | 8/405 |
| 2004/0074013 A1 | 4/2004 | Terranova et al. | 8/405 |
| 2004/0078905 A1 | 4/2004 | Terranova et al. | 8/405 |
| 2004/0083559 A1 | 5/2004 | Sabelle et al. | 8/405 |
| 2004/0088799 A1 | 5/2004 | Sabelle et al. | 8/405 |

FOREIGN PATENT DOCUMENTS

| | | | |
|---|---|---|---|
| DE | 38 43 892 | | 6/1990 |
| DE | 41 33 957 | | 4/1993 |
| DE | 42 34 886 A1 | | 4/1994 |
| DE | 42 41 532 | | 6/1994 |
| DE | 42 41 532 A1 * | | 6/1994 |
| DE | 195 43 988 | | 5/1997 |
| DE | 299 01 593 | | 4/1999 |
| DE | 299 02 262 | | 5/1999 |
| DE | 100 34 617 A1 | | 1/2002 |
| EP | 0 119 860 | | 9/1984 |
| EP | 0 122 324 | | 10/1984 |
| EP | 0 173 109 | | 3/1986 |
| EP | 0 216 479 | | 4/1987 |
| EP | 0 244 160 | | 11/1987 |
| EP | 0 285 274 | | 10/1988 |
| EP | 0 304 001 | | 2/1989 |
| EP | 0 456 226 | | 11/1991 |
| EP | 0 488 248 | | 6/1992 |
| EP | 0 488 909 | | 6/1992 |
| EP | 0 518 238 | | 12/1992 |
| EP | 0 557 851 | | 9/1993 |
| EP | 0 578 248 | | 1/1994 |
| EP | 0 714 954 | | 6/1996 |
| EP | 0 770 375 | | 5/1997 |
| EP | 0 943 614 A2 | | 9/1999 |
| EP | 0 962 452 | | 12/1999 |
| EP | 1 018 508 A1 | | 7/2000 |
| FR | 1 400 366 | | 4/1965 |
| FR | 2 075 583 | | 10/1971 |
| FR | 2 270 846 | | 12/1975 |
| FR | 2 316 271 | | 1/1977 |
| FR | 2 320 330 | | 3/1977 |
| FR | 2 336 434 | | 7/1977 |
| FR | 2 413 907 | | 8/1979 |
| FR | 2 586 913 | | 3/1987 |
| FR | 2 733 749 | | 11/1996 |
| FR | 2 750 048 | | 12/1997 |
| FR | 2 766 178 A1 | | 1/1999 |
| FR | 2 801 308 | | 5/2001 |
| GB | 1 021 400 | | 3/1966 |
| GB | 1 026 978 | | 4/1966 |
| GB | 1 153 196 | | 5/1969 |
| GB | 1 458 377 | | 12/1976 |
| GB | 1 597 034 | | 9/1981 |
| GB | 2 239 265 | | 6/1991 |
| JP | 54-062335 | | 5/1979 |
| JP | 56-092812 | | 7/1981 |
| JP | 58-42045 | | 3/1983 |
| JP | 59-98437 | | 6/1984 |
| JP | 59-99437 | | 6/1984 |
| JP | 59-162548 | | 9/1984 |
| JP | 59-171956 | | 9/1984 |
| JP | 60-33552 | | 2/1985 |
| JP | 60-43659 | | 3/1985 |
| JP | 60-172982 | | 9/1985 |
| JP | 60-190779 | | 9/1985 |
| JP | 61-165315 | | 7/1986 |
| JP | 62-279337 | | 12/1987 |
| JP | 1-115048 | | 5/1989 |
| JP | 2-19576 | | 1/1990 |
| JP | 88-169571 | | 1/1990 |
| JP | 4-235909 | | 8/1992 |
| JP | 5-163124 | | 6/1993 |
| JP | 6-199642 | | 7/1994 |
| JP | 6-236011 | | 8/1994 |
| JP | 6-329522 | | 11/1994 |
| JP | 7-36159 | | 2/1995 |
| JP | 7-076509 | | 3/1995 |
| JP | 7-84348 | | 3/1995 |
| JP | 7-92632 | | 4/1995 |
| JP | 7-98489 | | 4/1995 |
| JP | 7-244361 | | 9/1995 |
| JP | 7-267832 | | 10/1995 |
| JP | 7-267835 | | 10/1995 |
| JP | 7-325375 | | 12/1995 |
| JP | 8-034714 | | 2/1996 |
| JP | 8-231359 | | 9/1996 |
| JP | 11-071247 | | 3/1999 |
| JP | 11-158048 | | 6/1999 |
| JP | 11-292745 | | 10/1999 |
| WO | WO 94/08969 | | 4/1994 |
| WO | WO 94/08970 | | 4/1994 |
| WO | WO 95/01772 | | 1/1995 |
| WO | WO 95/15144 | | 6/1995 |
| WO | WO 96/15765 | | 5/1996 |
| WO | WO 98/01106 | | 1/1998 |
| WO | WO 98/20847 | | 5/1998 |
| WO | WO 98/38175 | | 9/1998 |
| WO | WO 98/01434 | | 1/1999 |
| WO | WO 99/03819 | | 1/1999 |
| WO | WO 99/11229 | | 3/1999 |
| WO | WO 99/17725 | * | 4/1999 |
| WO | WO 99/64417 | | 12/1999 |
| WO | WO 01/68043 | | 9/2001 |

WO  WO 02/45675 A1  6/2002

OTHER PUBLICATIONS

Hans Beyer et al., "Über die Pyrazolbidung aus α-Chlor-acetessigester und Thiocarbohydrazid", Chemische Berichte, pp. 2550-2555, 1956.
R. Stollé, "Ueber die Ueberführung der secundären Säurehydrazide in Derivate des Furodiazols, Pyrrodiazols und Thiodiazols", Berichte Der Deutschen Chemischen Gesellschaft, pp. 797-798, 1899.
Mohamed Elnagdi et al., "Routes for the Synthesis of 3,5-Diaminopyrazoles, 2-Aminopyrazolo[1,5-a]pyrimidines and 5-Aminopyrazolo[1,5-a]pyrimidines", Journal Für Praktische Chemie, pp. 533-538, 1978.
E.J. Browne et al., "Triazoles. Part VII. Syntheses of Substituted 1,2,4-Triazoles", Journal of The Chemical Society, pp. 5149-5152, 1962.
Philip Magnus et al., "Synthesis of Helical Poly-β-pyrroles. Multiple Atropisomerism Resulting in Helical Enantiomorphic Conformations", Journal of the American Chemical Society, pp. 2465-2468, 1990.
Paul Carter et al., "Studies on the Synthesis of the Antitumor Agent CC-1065. Synthesis of PDE I and PDE II, Inhibitors of Cyclic Adenosine-3',5'-monophosphate Phosphodiesterase Using the 3,3'-Bipyrrole Strategy", Journal of the American Chemical Society, pp. 2711-2717, 1987.
H. Koopman, :"Investigations on Herbicides IV, The synthesis of 2,6-dichlorobenzonitrile", Recueil, pp. 1075-1083, 1961.
Lidia Wyzgowska, et al., "O ReakcjachTrikarboetoksymetanu", Acta Poloniae Pharmaceutica, pp. 83-88, 1982.
E. Hannig et al., "Kurze Orginalmitteilungen", Die Pharmazie, p. 231, 1980.
Mohamed Elnagdi et al., "Studies on 3,5-pyrazolidinediones. IV. Addition of 4-Arylazo-3,5-pyrazolidinediones to Ethyl Acrylate", Bulletin of the Chemical Society of Japan, vol. 46, 1973. pp. 1830-1833.
Giuliana Cardillo et al., "Sulle 1,2-difenil-3,5-dichetopirazolidine", Gazzetta Chimica Italiana, vol. 96, pp. 973-985, 1966.
Mohamed Ali et al., "Reactions with Thiazolo[3,2-b]-s-triazol-3(2H)-ones", Journal Für Praktische Chemie, pp. 12-18, 1976.
Eser Ilhan, et al., "Synthese von 6-Benzyliden-2-(α,α-diphenyl-α-hydroxyacetyl)-thiazolo[3,2-b]-s-frialzol-5-onen als potentiell biologisch wirksame Stroffe", Archiv der Pharmazie, pp. 825-826, 1994.
Thomas Kauffman et al., "Synthese von Amidrazonen aus Nitrilen und Natriumhydrazid", Chemische Berichte, pp. 3436-3443, 1964.
Henryk Foks et al., "Synthesis and Biological Activity of Thiazolo-1,2,4-Triazoles", Acta Poloniae Pharmaceutica—Drug Research, pp. 415-420, 1995.
Victor Cohen, "A New Method of Synthesis of Some 2-Aryl and 2-Heterocyclic Benzimidazole, Benzoxazole and Benzothiazole Derivatives", Journal of Heterocyclic Chemistry, 16, pp. 13-16, 1979.
S. Hiller et al., "Electron Density Distribution In Hetrocyclic Systems With Two Adjacent Nitrogen Atoms", Chemistry of Heterocyclic Compounds, pp. 93-96, 1965.
G. Fonnum et al., "Associative thickeners. Part I: Synthesis, rheology and aggregation behavior", Colloid & Polymer Science, 271, pp. 380-389, 1993.
R. L. Bent et al. "Chemical Constitution, Electrochemical, Photographic and Allergenic Properties of α-Amino-N-dialkylanilines", Journal of the American Chemical Society, pp. 3100-3125, 1951.
English language Derwent Abstract of JP 2019576, Jan. 23, 1990.
English language Derwent Abstract of JP 5163124, Jun. 29, 1993.
English language Derwent Abstract of JP 7036159, Feb. 7, 1995.
English language Derwent Abstract of JP 7084348, Mar. 31, 1995.
English language Derwent Abstract of JP 7092632, Apr. 7, 1995.
English language Derwent Abstract of JP 7098489, Apr. 11, 1995.
English language Derwent Abstract of JP 7244361, Sep. 19, 1995.
English language Derwent Abstract of JP 7325375, Dec. 12, 1995.
English language Derwent Abstract of JP 11-158048, Jun. 15, 1999.
English language Derwent Abstract of JP 58042045, Mar. 11, 1983.
English language Derwent Abstract of JP 5999437, Jun. 8, 1984.
English language Derwent Abstract of JP 6033552, Feb. 20, 1985.
English language Derwent Abstract of JP 6043659, Mar. 8, 1985.
English language Derwent Abstract of JP 60190779, Sep. 28, 1985.
English language Derwent Abstract of JP 6236011, Aug. 23, 1994.
English language Derwent Abstract of JP 62279337, Dec. 4, 1987.
English language Derwent Abstract of FR 2320330, Mar. 4, 1977.
English language Derwent Abstract of FR 2336434, Jul. 22, 1977.
English language Derwent Abstract of FR 2 750 048, Dec. 26, 1997.
English language Derwent Abstract of DE 4241532, Jun. 16, 1994.
English language Derwent Abstract of EP 0 770 375, May 2, 1997.
Co-pending U.S. Appl. No. 10/397,245, filed Mar. 27, 2003.
Co-pending U.S. Appl. No. 10/433,408, filed Jun. 4, 2003.
Co-pending U.S. Appl. No. 10/433,411, filed Oct. 29, 2003.
Co-pending U.S. Appl. No. 10/433,687, filed Jun. 5, 2003.
Co-pending U.S. Appl. No. 10/433,688, filed Nov. 5, 2003.
Co-pending U.S. Appl. No. 10/433,689, filed Nov. 12, 2003.
Co-pending U.S. Appl. No. 10/603,831, filed Jun. 26, 2003.
Co-pending U.S. Appl. No. 10/612,986, filed Jul. 7, 2003.
Co-pending U.S. Appl. No. 10/657,245, filed Dec. 9, 2003.
English language Derwent Abstract of DE 100 34 617.
English language Derwent Abstract of JP 11-071247.
English language Derwent Abstract of JP 1-115048.
English language Derwent Abstract of JP 7-267832.
English language Derwent Abstract of JP 7-267835.
English language Derwent Abstract of JP application 88-169571.
French Search Report for FR 02/03847, Nov. 25, 2002.
French Search Report for FR 02/07939, Feb. 17, 2003.
French Search Report for FR 02/08514, Mar. 20, 2003.
French Search Report for FR 02/11133, May 15, 2003.
International Search Report for PCT/FR 01/00745, Sep. 14, 2001.
International Search Report for PCT/FR 01/03540, Mar. 11, 2002.
International Search Report for PCT/FR 01/03541, Mar. 11, 2002.
International Search Report for PCT/FR 01/03542, Mar. 11, 2002.
International Search Report for PCT/FR 01/03543, Mar. 14, 2002.
International Search Report for PCT/FR 01/03571, Mar. 11, 2002.
Office Action in co-pending U.S. Appl. No. 10/433,687 dated Apr. 8, 2005.
Office Action in co-pending U.S. Appl. No. 10/433,411 dated Apr. 8, 2005.
Office Action in co-pending U.S. Appl. No. 10/433,411 dated Sep. 9, 2004.
Office Action in co-pending U.S. Appl. No. 10/433,687 dated Sep. 14, 2004.
Office Action in co-pending U.S. Appl. No. 10/433,688 dated Feb. 10, 2005.
Office Action in co-pending U.S. Appl. No. 10/433,688 dated Sep. 9, 2004.
Office Action in co-pending U.S. Appl. No. 10/433,689 dated Oct. 26, 2004.
Office Action in co-pending U.S. Appl. No. 10/433,687 dated Aug. 31, 2005.
Office Action in co-pending U.S. Appl. No. 10/433,408 dated Jul. 5, 2005.
Office Action in co-pending U.S. Appl. No. 10/433,411 dated Aug. 31, 2005.
Office Action in co-pending U.S. Appl. No. 10/433,689 dated Aug. 2, 2005.

* cited by examiner

DYEING COMPOSITIONS FOR KERATINOUS FIBERS CONTAINING PARAPHENYLENEDIAMINE DERIVATIVES WITH PYRROLIDINYL GROUP

The invention relates to novel compositions for the oxidation dyeing of keratin fibers, comprising at least one para-phenylenediamine derivative containing a pyrrolidinyl group as oxidation base, to a dyeing process and to a dyeing kit using this composition.

It is known practice to dye keratin fibers, and in particular human hair, with dye compositions containing oxidation dye precursors, in particular ortho- or para-phenylenediamines, ortho- or para-aminophenols, and heterocyclic bases such as diaminopyrazole derivatives, which are generally known as oxidation bases. These oxidation dye precursors (oxidation bases) are colorless or weakly colored compounds which, when combined with oxidizing products, can give rise to colored compounds and dyes by a process of oxidative condensation.

It is also known that the shades obtained with these oxidation bases can be varied by combining them with couplers or coloration modifiers, the latter being chosen in particular from aromatic meta-diamines, meta-aminophenols, meta-diphenols and certain heterocyclic compounds.

The variety of molecules used as oxidation bases and couplers allows a wide range of colors to be obtained.

The so-called "permanent" coloration obtained by means of these oxidation dyes should moreover satisfy a certain number of requirements. Thus, it should have no toxicological drawbacks, it should allow shades to be obtained in the desired intensity and it should have good staying power with respect to external agents (light, bad weather, washing, permanent-waving, perspiration or rubbing).

The dyes should also allow gray hair to be covered and, finally, they should be as unselective as possible, i.e. they should allow only the smallest possible differences in coloration to be obtained along the same keratin fiber, which may indeed be differently sensitized (i.e. damaged) between its tip and its root.

In the field of hair dyeing, para-phenylenediamine and para-toluylenediamine are oxidation bases that are widely used. With oxidation couplers, they make it possible to obtain a variety of shades.

However, there is a need to discover novel oxidation bases, also known as developers, which have a better toxicological profile than para-phenylenediamine or para-toluylenediamine, while at the same time making it possible to give the hair excellent properties of color intensity, of variety of shades, of color uniformity and of staying power with respect to external agents.

It has already been proposed, especially in patent application GB 2 239 265, to use 2-(β-hydroxyethyl)-para-phenylenediamine or N,N-bis(β-hydroxyethyl)-para-phenylenediamine as potential replacements for para-phenylenediamine and para-toluylenediamine. This is likewise the case for 2-(hydroxyalkoxy)-para-phenylenediamines (see especially U.S. Pat. No. 5,538,516).

However, N,N-bis-(β-hydroxyethyl)-para-phenylenediamine and 2-(β-hydroxyethyl)-para-phenylenediamine nevertheless have the drawback of giving a more limited variety of shades and of giving less color intensity and less uniformity to the hair than para-phenylenediamine or para-toluylenediamine. It is likewise the case for 2-(hydroxyalkoxy)-para-phenylenediamines, which give the hair a color which evolves and changes over time.

Moreover, it is known from the literature, see R. L. Bent et al., J.A.C.S. 73, 3100, 1951, that para-phenylenediamine derivatives in which one of the nitrogen atoms is included in a non-aromatic 6- or 7-membered carbon-based or heterocyclic ring are less oxidizable than para-phenylenediamine derivatives in which one of the nitrogen atoms is substituted with two disymmetric substituents, which are themselves less oxidizable than para-phenylenediamine derivatives in which one of the nitrogen atoms is substituted with two symmetrical substituents.

It is also mentioned in the same article that the para-phenylenediamine derivative in which one of the nitrogen atoms is included in a non-aromatic 5-membered carbon-based ring is more oxidizable than each of the derivatives mentioned above. This particular class of N-pyrrolidine derivatives of para-phenylenediamine thus makes it possible to obtain kinetically accelerated condensation reactions with couplers in basic and oxidative medium when compared with the para-phenylenediamine derivatives mentioned above.

However, oxidation bases which are too oxidizable and which react with couplers at accelerated reaction rates generally lead to the formation of dyes on the exterior of the keratin fiber. Intensities, staying power and uniformity of the colorations thus obtained on the hair are generally insufficient.

However, U.S. Pat. No. 5,851,237 proposes the use of 1-(4-aminophenyl)pyrrolidine derivatives optionally substituted on the benzene nucleus, in order to replace para-phenylenediamine. In this respect, the same patent very preferentially proposes to use 1-(4-amino-phenyl)pyrrolidine as a replacement for para-phenylenediamine.

Now, it is known in the literature that 1-(4-aminophenyl)pyrrolidine has highly allergenic activity (R. L. Bent et al., J.A.C.S. 73, 3100, 1951).

U.S. Pat. No. 5,993,491 also proposes the use of N-(4-aminophenyl)-2-(hydroxymethyl)pyrrolidines optionally substituted on the benzene nucleus, in order to replace para-phenylenediamine. As very preferential compounds claimed, said patent proposes N-(4-aminophenyl)-2-(hydroxymethyl)pyrrolidine optionally substituted with a methyl radical in position 3.

However, it has been clearly established that these compounds do not make it possible to give the hair a coloration of equivalent quality to that obtained with para-phenylenediamine, due to a lack of intensity and uniformity of the color obtained.

Patent application JP 11 158 048 also proposes hair-coloring compositions which offer good properties of spreading, ease of application and resistance to shampoo. These dye compositions contain at least one compound chosen from para-phenylenediamine derivatives optionally substituted with 1 to 4 substituents on the benzene nucleus and one of the nitrogen atoms of which is included in a 5- to 7-membered carbon-based ring, or from para-phenylenediamine derivatives optionally substituted with 1 to 4 substituents on the benzene nucleus and one of the nitrogen atoms of which is substituted with a radical $Z_1$ and a radical $Z_2$, $Z_1$ being an alkyl or aryl group or a heterocycle, and $Z_2$ being a radical —$(CH_2—CH_2—O)—Z_3$ in which $Z_3$ represents a hydrogen atom, an alkyl or aryl group or a heterocycle.

In terms of coloring power, ease of application, uniformity of the coloration obtained and staying power especially with respect to the action of shampoos. It is seen in this Japanese patent application that the preferred derivatives, namely N-(3-isopropyloxy-4-aminophenyl)-2,5-diethylpyrrolidine, N-(3-methyl-4-aminophenyl)-3-(2-hydroxyethyl-oxy)pyrrolidine and N-(3-methyl-4-aminophenyl)-2-methyl-4-hydroxypyrrolidine behave like oxidation bases equivalent to 4-aminoaniline derivatives in which the nitrogen atom is included in a functionalized 6-membered piperidine ring.

However, it is known that when one of the nitrogen atoms of the para-phenylenediamine derivatives is included in a 6-membered ring, the activation energy to lead to the corresponding quinone-imine oxidized form is among the highest in the N,N-disubstituted para-phenylenediamine series. The consequence of these data is that the condensation reactions with couplers are less efficient and give the hair insufficient coloring properties in terms of intensity and uniformity of the color obtained, when compared with those obtained with para-phenylenediamine or para-toluylenediamine.

The result of this is that the solutions proposed in patent application JP 11 158 048, by means of para-phenylenediamine derivatives having a nitrogen atom included in a functionalized pyrrolidine ring, do not make it possible to give the hair dyeing results that are equivalent to those obtained with para-phenylenediamine or para-toluylenediamine.

It is thus clear that there is a real need to discover novel oxidation bases that have both a good toxicological profile and properties such that the compositions containing them make it possible to give the hair colorations with excellent properties of color intensity, of variety of shades, of color uniformity (that is to say a low selectivity) and of staying power with respect to the various external attacking factors to which the hair may be subjected.

The applicant has now discovered, entirely surprisingly and unexpectedly, that certain para-phenylenediamine derivatives containing a pyrrolidinyl group of formula (I) defined below, are not only well suited for use as oxidation bases for the oxidation dyeing of keratin fibers, but also lead to particularly powerful and relatively unselective colorations. They moreover make it possible to obtain dye compositions which give colorations that are resistant to the various attacking factors to which the hair may be subjected.

These discoveries form the basis of the present invention.

A first subject of the invention is thus a composition for the oxidation dyeing of keratin fibers, and in particular of human keratin fibers such as the hair, characterized in that it comprises, in a medium which is suitable for dyeing, at least one oxidation base chosen from para-phenylenediamine derivatives containing a pyrrolidinyl group of formula (I) below, and the addition salts thereof with an acid:

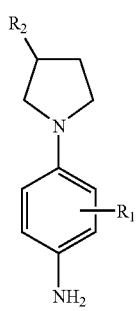

(I)

in which:

$R_1$ represents a hydrogen atom; a halogen atom chosen from a chlorine atom and a bromine atom; a linear or branched $C_1$–$C_7$ alkyl radical, the branch(es) possibly forming one or more 3- to 5-membered carbon-based rings, which may contain one or more double bonds and/or one or more triple bonds, said double bonds optionally being able to lead to aromatic groups, one or more carbon atoms of which may be replaced with an oxygen, nitrogen or sulfur atom or with an $SO_2$ group, and the carbon atoms of which may be, independently of each other, substituted with one or more halogen atoms; said radical $R_1$ containing no peroxide bond or diazo, nitro or nitroso radicals;

$R_2$ represents a hydroxyl radical; an amino radical; a group —$OR_3$ in which $R_3$ represents a linear or branched $C_1$–$C_4$ alkyl radical substituted with one or more radicals chosen from the group consisting of a halogen atom, $C_1$–$C_2$ alkoxy, amino or $C_1$–$C_2$ aminoalkyl or a $C_3$–$C_4$ alkyl radical substituted with one or more hydroxyl radicals; a group —$NR_4R_5$ in which $R_4$ and $R_5$ represent, independently of each other, a hydrogen atom, a linear or branched $C_1$–$C_4$ alkyl radical substituted with one or more radicals chosen from the group consisting of a halogen atom and a hydroxyl, $C_1$–$C_2$ alkoxy, amino or $C_1$–$C_2$ aminoalkyl radical.

As mentioned above, the colorations obtained with the oxidation dye composition in accordance with the invention are powerful and relatively unselective and also have excellent properties of resistance with respect to the action of the various external agents (light, bad weather, washing, permanent-waving, perspiration and rubbing). The oxidation dye compositions in accordance with the invention furthermore make it possible to achieve shades in a very broad range of colors.

According to the invention, when it is indicated that one or more of the carbon atoms of the radical $R_1$ can be replaced with an oxygen, nitrogen or sulfur atom or with an $SO_2$ group, and/or when said radical $R_1$ can contain one or more double bonds and/or one or more triple bonds, this means that, for example, the following conversions can be carried out;

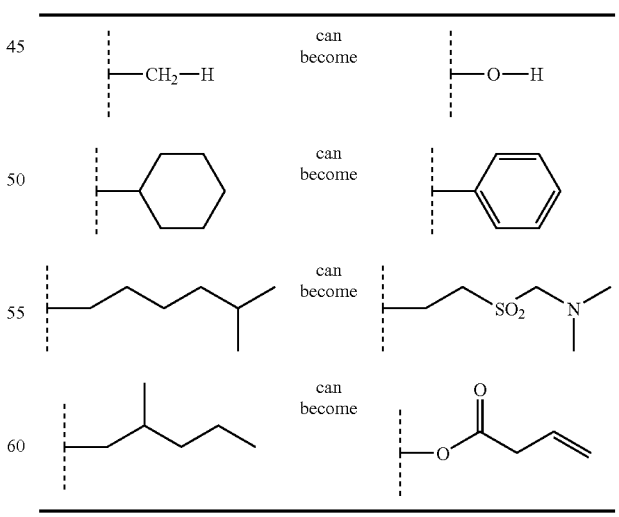

In particular, $R_1$ may be chosen from a hydrogen atom, a linear or branched, saturated or unsaturated hydrocarbon-based chain, alkoxy, alkoxyalkyl, mono- or polyhydroxyalkyl, aminoalkyl, carboxyalkyl, hydroxyaminoalkyl and hydroxyalkoxy groups. Among these substituents, $R_1$ may especially represent a hydrogen atom or a methyl, ethyl, isopropyl, vinyl, allyl, methoxymethyl, hydroxymethyl, 1-carboxymethyl, 1-aminomethyl, 2-carboxymethyl, 2-hydroxyethyl, 3-hydroxypropyl, 1,2-dihydroxyethyl, 1-hydroxy-2-aminoethyl, methoxy, ethoxy, allyloxy or 3-hydroxyethyloxy radical. Among these substituents, $R_1$ preferably represents a hydrogen atom or a methyl, hydroxymethyl, 2-hydroxyethyl, 1,2-dihydroxyethyl, methoxy or 2-hydroxyethoxy radical.

Among these substituents, $R_1$ even more preferentially represents a hydrogen atom or a methyl radical.

Among the substituents $R_2$ that are useful for the invention, $R_2$ represents a hydroxyl radical; an amino radical; a group —$OR_3$ in which $R_3$ represents a linear or branched $C_1$–$C_4$ alkyl radical substituted with one or more radicals chosen from the group consisting of a halogen atom, $C_1$–$C_2$ alkoxy, amino and $C_1$–$C_2$ aminoalkyl; a group —$NR_4R_5$ in which $R_4$ and $R_5$ represent, independently of each other, a hydrogen atom, a linear or branched $C_1$–$C_4$ alkyl radical substituted with one or more radicals chosen from the group consisting of a halogen atom and a hydroxyl, $C_1$–$C_2$ alkoxy, amino or $C_1$–$C_2$ aminoalkyl radical. Preferably, $R_2$ represents a hydroxyl, acetoxy, amino, methylamino, dimethylamino or 2-hydroxyethylamino radical. Among these substituents, $R_2$ even more preferentially represents a hydroxyl or amino radical.

Among the para-phenylenediamine derivatives containing a pyrrolidinyl group of formula (I) above, mention may be made especially of N-(4-aminophenyl)-3-hydroxypyrrolidine, N-(4-amino-2-methylphenyl)-3-hydroxypyrrolidine, N-(4-amino-2-ethylphenyl)-3-hydroxypyrrolidine, N-(4-amino-2-methoxyphenyl)-3-hydroxypyrrolidine, N-(4-amino-2-(2-hydroxy-ethyl)phenyl)-3-hydroxypyrrolidine, N-(4-amino-2-(1-hydroxyethyl)phenyl)-3-hydroxypyrrolidine, N-(4-amino-2-(1,2-dihydroxyethyl)phenyl)-3-hydroxypyrrolidine, N-(4-amino-3-methylphenyl)-3-hydroxypyrrolidine, N-(4-amino-3-ethylphenyl)-3-hydroxypyrrolidine, N-(4-amino-3-methoxyphenyl)-3-hydroxypyrrolidine, N-(4-amino-3-(2-hydroxy-ethyl)phenyl)-3-hydroxypyrrolidine, N-(4-amino-3-(1-hydroxyethyl)phenyl)-3-hydroxypyrrolidine, N-(4-amino-3-(1,2-dihydroxyethyl)phenyl)-3-hydroxypyrrolidine, N-(4-aminophenyl)-3-aminopyrrolidine, N-(4-amino-2-methylphenyl)-3-aminopyrrolidine, N-(4-amino-2-ethylphenyl)-3-aminopyrrolidine, N-(4-amino-2-methoxyphenyl)-3-aminopyrrolidine, N-(4-amino-2-(2-hydroxyethyl)-phenyl)-3-aminopyrrolidine, N-(4-amino-2-(1-hydroxy-ethyl)phenyl)-3-aminopyrrolidine, N-(4-amino-2-(1,2-dihydroxyethyl)phenyl)-3-hydroxypyrrolidine, N-(4-amino-3-methylphenyl)-3-aminopyrrolidine, N-(4-amino-3-ethylphenyl)-3-aminopyrrolidine, N-(4-amino-3-methoxyphenyl)-3-aminopyrrolidine, N-(4-amino-3-(2-hydroxyethyl)phenyl)-3-amino-pyrrolidine, N-(4-amino-3-(1-hydroxyethyl)phenyl)-3-aminopyrrolidine and N-(4-amino-3-(1,2-dihydroxyethyl)phenyl)-3-aminopyrrolidine, and the addition salts thereof with an acid.

The para-phenylenediamine derivatives containing a pyrrolidinyl group of formula (I), and processes for synthesizing them, are known; see in particular patent application DE 4 241 532 (AGFA).

The para-phenylenediamine derivative(s) containing a pyrrolidinyl group of formula (I) in accordance with the invention and/or the addition salt(s) thereof with an acid preferably represent(s) from 0.0005% to 12% by weight approximately relative to the total weight of the dye composition, and even more preferentially from 0.005% to 6% by weight approximately relative to this weight.

The medium which is suitable for dyeing (or support) generally consists of water or of a mixture of water and at least one organic solvent to dissolve the compounds which would not be sufficiently water-soluble. Organic solvents which may be mentioned, for example, include $C_1$–$C_4$ lower alkanols, such as ethanol and isopropanol; glycerol; glycols and glycol ethers, for instance 2-butoxyethanol, propylene glycol, propylene glycol monomethyl ether and diethylene glycol monoethyl ether and monomethyl ether, and also aromatic alcohols, for instance benzyl alcohol or phenoxyethanol, similar products and mixtures thereof.

The solvents may be present in proportions preferably of between 1% and 40% by weight approximately relative to the total weight of the dye composition, and even more preferentially between 5% and 30% by weight approximately.

The pH of the dye composition in accordance with the invention is generally between 3 and 12 approximately and preferably between 5 and 11 approximately. It may be adjusted to the desired value by means of acidifying or basifying agents usually used in the dyeing of keratin fibers, or alternatively using conventional buffer systems.

Among the acidifying agents which may be mentioned, for example, are mineral or organic acids, for instance hydrochloric acid, orthophosphoric acid, sulfuric acid, carboxylic acids, for instance acetic acid, tartaric acid, citric acid and lactic acid, and sulfonic acids.

According to one particular embodiment, the basifying agents are chosen from alkanolamines, diaminoalkanes and aqueous ammonia.

For the purposes of the present invention, the term "alkanolamine" means any saturated or unsaturated, linear or branched hydrocarbon-based compound containing from 2 to 100 carbon atoms and comprising (i) at least one amine function optionally substituted with one or two substituents which are preferably $C_1$–$C_4$ alkyl or substituted $C_1$–$C_4$ alkyl, such as, for example, mono- or polyhydroxyalkyl, and (ii) at least one hydroxyl function not borne by the amine function. Preferably, the hydrocarbon-based chain is saturated.

Among the alkanolamines which may be used according to the invention, mention may be made of monoethanolamine, diethanolamine, triethanolamine, triisopropanolamine, 2-amino-2-methyl-1-propanol, 2-amino-2-methyl-1,3-propanediol, 2-amino-2-ethyl-1,3-propanediol, 2-amino-1-butanol, tris(hydroxy-methyl)aminomethane, 2-aminoethylethanolamine, 1-diethylamino-2,3-propanediol, 2-dimethylamino-2-methyl-1-propanol, dimethylethanolamine, diethylethanolamine, ethylmonoethanolamine and methylethanolamine. Preferably, monoethanolamine is used.

The diaminoalkanes used according to the invention are preferably the diaminoalkanes of formula (II) below:

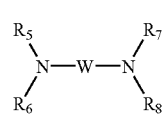

(II)

in which W is an alkylene residue optionally substituted with a hydroxyl group or a $C_1$–$C_4$ alkyl radical; $R_5$, $R_6$, $R_7$ and $R_8$, which may be identical or different, represent a hydrogen atom, a $C_1$–$C_4$ alkyl radical or a $C_1$–$C_4$ hydroxyalkyl radical. Preferably, W is a propylene residue. Even more preferentially, the diaminoalkane is diaminopropane.

Among all the alkaline agents which may be used according to the invention, aqueous ammonia is preferably used.

The alkaline agent(s) is (are) present in the ready-to-use oxidation dye composition or the composition intended for oxidation dyeing according to the invention in concentrations ranging from about 0.1% to about 20% by weight, and preferably from about 0.5% to about 10% by weight of active material relative to the total weight of the composition intended for oxidation dyeing or the ready-to-use oxidation dye composition.

According to one preferred embodiment, the oxidation dye composition in accordance with the invention also contains one or more couplers so as to modify the shades obtained by using the compounds of formula (I), or to enrich the shades with glints.

The couplers which may be used in the oxidation dye compositions in accordance with the invention may be chosen from couplers conventionally used in oxidation dyeing, and among which mention may be made especially of meta-phenylenediamines, meta-aminophenols, meta-diphenols, naphthols and heterocyclic couplers such as pyrazolo[1,5-b]-1,2,4-triazoles, pyrazolo[3,2-c]-1,2,4-triazoles, pyrazol-5-ones, pyridines, indoles, indolines, indazoles, benzimidazoles, benzothiazoles, benzoxazoles, 1,3-benzodioxoles and quinolines.

According to one particular embodiment, the coupler(s) is (are) chosen from heterocyclic couplers, substituted meta-diphenols, substituted meta-phenylenediamines, naphthols and acylated naphthols, and the meta-aminophenols of formula (III) below, and the addition salts thereof with an acid:

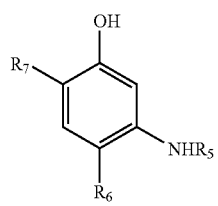

(III)

in which:
$R_5$ represents a hydrogen atom or a $C_1$–$C_4$ alkyl, $C_1$–$C_4$ monohydroxyalkyl or $C_2$–$C_4$ polyhydroxyalkyl radical,
$R_6$ represents a hydrogen atom, a $C_1$–$C_4$ alkyl or $C_1$–$C_4$ alkoxy radical or a halogen atom chosen from chlorine, bromine and fluorine,
$R_7$ represents a hydrogen atom or a $C_1$–$C_4$ alkyl, $C_1$–$C_4$ alkoxy, $C_1$–$C_4$ monohydroxyalkyl, $C_2$–$C_4$ polyhydroxyalkyl, $C_1$–$C_4$ monohydroxyalkoxy or $C_2$–$C_4$ polyhydroxyalkoxy radical.

Among the substituted meta-diphenols which may be used as couplers in the dye composition in accordance with the invention, the compounds which will preferably be used are those of formula (VI) below, and the addition salts thereof with an acid.

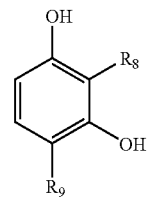

(VI)

in which:
$R_8$ and $R_9$, which may be identical or different, represent a hydrogen atom, a $C_1$–$C_4$ alkyl radical or a halogen atom chosen from chlorine, bromine and fluorine, it being understood that at least one of the radicals $R_8$ and $R_9$ is other than a hydrogen atom.

Among the substituted meta-diphenols of formula (VI) above which may be mentioned more particularly are 2-methyl-1,3-dihydroxybenzene, 4-chloro-1,3-dihydroxybenzene and 2-chloro-1,3-dihydroxybenzene, and the addition salts thereof with an acid.

Among the substituted meta-phenylenediamines which may be used as couplers in the dye composition in accordance with the invention, the compounds which will preferably be used are those of formula (V) below, and the addition salts thereof with an acid:

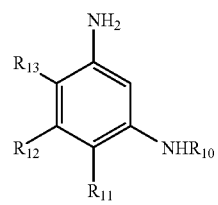

(V)

in which:
$R_{10}$ represents a hydrogen atom or a $C_1$–$C_4$ alkyl, $C_1$–$C_4$ monohydroxyalkyl or $C_2$–$C_4$ polyhydroxyalkyl radical;
$R_{11}$ and $R_{12}$, which may be identical or different, represent a hydrogen atom or a $C_1$–$C_4$ alkyl, $C_1$–$C_4$ monohydroxyalkoxy or $C_2$–$C_4$ polyhydroxyalkoxy radical;
$R_{13}$ represents a hydrogen atom, a $C_1$–$C_4$ alkoxy, $C_1$–$C_4$ aminoalkoxy, $C_1$–$C_4$ monohydroxyalkoxy or $C_2$–$C_4$ polyhydroxalkoxy radical or a 2,4-diaminophenoxyalkoxy radical; it being understood that at least one of the radicals $R_{10}$ to $R_{13}$ is other than a hydrogen atom.

Among the substituted meta-phenylenediamines of formula (V) above which may be mentioned more particularly are 3,5-diamino-1-ethyl-2-methoxybenzene, 3,5-diamino 2-methoxy-1-methylbenzene, 2,4-diamino-1-ethoxybenzene, 1,3-bis(2,4-diaminophenoxy)propane, bis(2,4-diaminophenoxy)methane, 1-(β-aminoethyloxy)-2,4-diaminobenzene, 2-amino-1-(β-hydroxyethyloxy)-4-methylaminobenzene, 2,4-diamino-1-ethoxy-5-methylbenzene, 2,4-diamino-5-(β-hydroxyethyloxy)-1-methylbenzene, 2,4-diamino-1-(β,γ-dihydroxypropyloxy)benzene, 2,4-diamino-1-(β-hydroxyethyloxy)benzene and 2-amino-4-N-(β-hydroxyethyl)amino-1-methoxybenzene, and the addition salts thereof with an acid.

Among the heterocyclic couplers which may be used in the dye composition in accordance with the invention, mention may be made especially of indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazolin-3,5-dione derivatives, pyrrolo[3,2-d]oxazole derivatives, pyrazolo[3,4-d]thiazole derivatives, thiazoloazole S-oxide derivatives and thiazoloazole S,S-dioxide derivatives, and the addition salts thereof with an acid.

Among the indole derivatives which may be used as heterocyclic couplers in the dye composition in accordance with the invention, mention may be made particularly of the compounds of formula (VI) below, and the addition salts thereof with an acid:

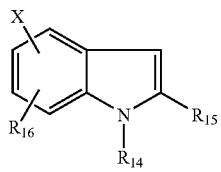

(VI)

in which:

$R_{14}$ represents a hydrogen atom, a $C_1$–$C_4$ alkyl, $C_1$–$C_4$ monohydroxyalkyl, $C_2$–$C_4$ polyhydroxyalkyl or $C_1$–$C_4$ aminoalkyl radical in which the amine is mono- or disubstituted with a $C_1$–$C_4$ alkyl group;

$R_{15}$ represents a hydrogen atom or a $C_1$–$C_4$ alkyl radical;

$R_{16}$ represents a hydrogen atom or a $C_1$–$C_4$ alkyl or hydroxyl radical;

X represents a hydroxyl radical or a radical $NHR_{17}$ in which $R_{17}$ represents a hydrogen atom or a $C_1$–$C_4$ alkyl or $C_1$–$C_4$ hydroxyalkyl radical.

Among the indole derivatives of formula (V) above which may be mentioned more particularly are 4-hydroxyindole, 6-hydroxyindole, 7-aminoindole, 6-aminoindole, 7-hydroxyindole, 7-ethyl-6-(β-hydroxyethyl)aminoindole, 4-aminoindole, 6-hydroxy-1-methylindole, 5,6-dihydroxyindole, 4-hydroxy-1-N-methylindole, 4-hydroxy-2-methylindole, 4-hydroxy-5-methylindole, 4-hydroxy-1-N-(β-hydroxyethyl)indole, 4-hydroxy-1-N-(β-hydroxypropyl)indole, 1-N-(β,γ-dihydroxypropyl)-4-hydroxyindole, 4-hydroxy-1-N-(β-hydroxyethyl)-5-methylindole and 1-N-(γ-dimethylaminopropyl)-4-hydroxyindole, and the addition salts thereof with an acid.

Among the indoline derivatives which may be used as heterocyclic couplers in the dye composition in accordance with the invention, mention may be made particularly of 4-hydroxyindoline, 6-hydroxyindoline, 6-aminoindoline and 5,6-dihydroxyindoline, and the addition salts thereof with an acid.

Among the benzimidazole derivatives which may be used as heterocyclic couplers in the dye composition in accordance with the invention, mention may be made more particularly of the compounds of formula (VII) below, and the addition salts thereof with an acid:

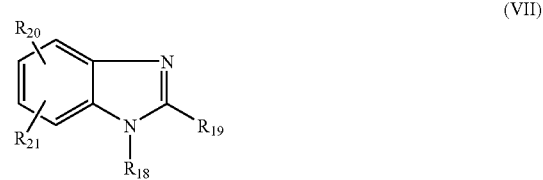

(VII)

in which:

$R_{18}$ represents a hydrogen atom or a $C_1$–$C_4$ alkyl radical, $R_{19}$ represents a hydrogen atom or a $C_1$–$C_4$ alkyl or phenyl radical, $R_{20}$ represents a hydroxyl, amino or methoxy radical, $R_{21}$ represents a hydrogen atom or a hydroxyl, methoxy or a $C_1$–$C_4$ alkyl radical, with the proviso that:

when $R_{20}$ denotes an amino radical, then it occupies position 4, when $R_{20}$ occupies position 4, then $R_{21}$ occupies position 7, when $R_{20}$ occupies position 5, then $R_{21}$ occupies position 6.

Among the benzimidazole derivatives of formula (VII) above, mention may be made more particularly of 4-hydroxybenzimidazole, 4-aminobenzimidazole, 4-hydroxy-7-methylbenzimidazole, 4-hydroxy-2-methylbenzimidazole, 1-butyl-4-hydroxybenzimidazole, 4-amino-2-methylbenzimidazole, 5,6-dihydroxybenzimidazole, 5-hydroxy-6-methoxybenzimidazole, 4,7-dihydroxybenzimidazole, 4,7-dihydroxy-1-methylbenzimidazole, 4,7-dimethoxybenzimidazole, 5,6-dihydroxy-1-methylbenzimidazole, 5,6-dihydroxy-2-methylbenzimidazole and 5,6-dimethoxybenzimidazole, and the addition salts thereof with an acid, Among the benzomorpholine derivatives which may be used as heterocyclic couplers in the dye composition in accordance with the invention, mention may be made more particularly of the compounds of formula (VIII) below, and the addition salts thereof with an acid:

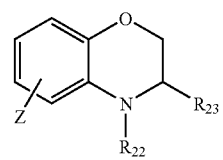

(VIII)

in which:

$R_{22}$ and $R_{23}$, which may be identical or different, represent a hydrogen atom or a $C_1$–$C_4$ alkyl radical, Z represents a hydroxyl or amino radical.

Among the benzomorpholine derivatives of formula (VIII) above which may be mentioned more particularly are 6-hydroxy-1,4-benzomorpholine, N-methyl-6-hydroxy-1,4-benzomorpholine and 6-amino-1,4-benzomorpholine, and the addition salts thereof with an acid.

Among the sesamol derivatives which may be used as heterocyclic couplers in the dye composition in accordance with the invention, mention may be made particularly of the compounds of formula (IX) below, and the addition salts thereof with an acid:

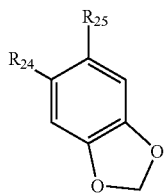
(IX)

in which:
R$_{24}$ denotes a hydroxyl, amino, C$_1$–C$_4$ alkylamino, C$_1$–C$_4$ monohydroxyalkylamino or C$_2$–C$_4$ polyhydroxyalkylamino radical, R$_{25}$ denotes a hydrogen or halogen atom or a C$_1$–C$_4$ alkoxy radical.

Among the sesamol derivatives of formula (IX) above which may be mentioned more particularly are 2-bromo-4,5-methylenedioxyphenol, 2-methoxy-4,5-methylenedioxyaniline and 2-(β-hydroxyethyl)amino-4,5-methylenedioxybenzene, and the addition salts thereof with an acid.

Among the pyrazoloazole derivatives which may be used as heterocyclic couplers in the dye composition in accordance with the invention, mention may be made more particularly of the compounds described in the following patents and patent applications:

FR-A-2 075 583, EP-A-0 119 860, EP-A-0 285 274, EP-A-0 244 160, EP-A-0 578 248, GB 1 458 377, U.S. Pat. Nos. 3,227,554, 3,419,391, 3,061,432, 4,500,630, 3,725,067, 3,926,631, 5,457,210, JP 84/99437, JP 83/42045, JP 84/162548, JP 84/171956, JP 85/33552, JP 85/43659, JP 85/172982, JP 85/190779 as well as in the following publications: Chem. Ber. 32, 797 (1899), Chem. Ber. 89, 2550, (1956), J. Chem. Soc. Perkin trans 1, 2047, (1977), J. Prakt. Chem., 320, 533, (1978); the teachings of which form an integral part of the present patent application.

Pyrazoloazole derivatives which may be mentioned most particularly are:
2-methylpyrazolo[1,5-b]-1,2,4-triazole,
2-ethylpyrazolo[1,5-b]-1,2,4-triazole,
2-isopropylpyrazolo[1,5-b]-1,2,4-triazole,
2-phenylpyrazolo[1,5-b]-1,2,4-triazole,
2,6-dimethylpyrazolo[1,5-b]-1,2,4-triazole,
7-chloro-2,6-dimethylpyrazolo[1,5-b]-1,2,4-triazole,
3,6-dimethylpyrazolo[3,2-c]-1,2,4-triazole,
6-phenyl-3-methylthiopyrazolo[3,2-c]-1,2,4-triazole,
6-aminopyrazolo[1,5-a]benzimidazole, and the addition salts thereof with an acid.

Among the pyrroloazole derivatives which may be used as heterocyclic couplers in the dye composition in accordance with the invention, mention may be made more particularly of the compounds described in the following patent applications and patents:

U.S. Pat. No. 5,256,526, EP-A-0 557 851, EP-A-0 578 248, EP-A-0 518 238, EP-A-0 456 226, EP-A-0 488 909, EP-A-0 488 248, and in the following publications:
D. R. Liljegren Ber. 1964, 3436;
E. J. Browne, J.C.S., 1962, 5149;
P. Magnus, J.A.C.S., 1990, 112, 2465;
P. Magnus, J.A.C.S., 1987, 109, 2711;
Angew. Chem. 1960, 72, 956; and
Rec. Trav. Chim. 1961, 80, 1075; the teachings of which form an integral part of the present patent application.

Pyrroloazole derivatives which may be mentioned most particularly are:
5-cyano-4-ethoxycarbonyl-8-methylpyrrolo[1,2-b]-1,2,4-triazole,
5-cyano-8-methyl-4-phenylpyrrolo[1,2-b]-1,2,4-triazole,
7-amido-6-ethoxycarbonylpyrrolo[1,2-a]benzimidazole, and the addition salts thereof with an acid.

Among the imidazoloazole derivatives which may be used as heterocyclic couplers in the dye composition in accordance with the invention, mention may be made more particularly of the compounds described in the following patent applications and patents: U.S. Pat. No. 5,441,863; JP 62-279 337; JP 06-236 011 and JP 07-092 632, the teachings of which form an integral part of the present patent application.

Imidazoloazole derivatives which may be mentioned most particularly are:
7,8-dicyanoimidazolo[3,2-a]imidazole,
7,8-dicyano-4-methylimidazolo[3,2-a]imidazole, and the addition salts thereof with an acid.

Among the pyrazolopyrimidine derivatives which may be used as heterocyclic couplers in the dye composition in accordance with the invention, mention may be made more particularly of the compounds described in the following patent application: EP-A-0 304 001, the teaching of which forms an integral part of the present patent application.

Pyrazolopyrimidine derivatives which may be mentioned most particularly are:
pyrazolo[1,5-a]pyrimidin-7-one,
2,5-dimethylpyrazolo[1,5-a]pyrimidin-7-one,
2-methyl-6-ethoxycarbonylpyrazolo[1,5-a]pyrimidin-7-one,
2-methyl-5-methoxymethylpyrazolo[1,5-a]pyrimidin-7-one,
2-tert-butyl-5-trifluoromethylpyrazolo[1,5-a]pyrimidin-7-one,
2,7-dimethylpyrazolo[1,5-a]pyrimidin-5-one, and the addition salts thereof with an acid.

Among the pyrazoline-3,5-dione derivatives which may be used as heterocyclic couplers in the dye composition in accordance with the invention, mention may be made more particularly of the compounds described in the following patent applications and patents: JP 07-036159, JP 07-084348 and U.S. Pat. No. 4,128,425, and in the following publications:
L. WYZGOWSKA, Acta. Pol. Pharm. 1982, 39 (1–3), 83.
E. HANNIG, Pharmazie, 1980, 35 (4), 231
M. H. ELNAGDI, Bull. Chem. Soc. Jap., 46 (6), 1830, 1973
G. CARDILLO, Gazz. Chim. Ital. 1966, 96, (8–9), 973, the teachings of which form an integral part of the present patent application.

Pyrazoline-3,5-dione derivatives which may be mentioned most particularly are:
1,2-diphenylpyrazoline-3,5-dione,
1,2-diethylpyrazoline-3,5-dione, and the addition salts thereof with an acid.

Among the pyrrolo[3,2-d]oxazole derivatives which may be used as heterocyclic couplers in the dye composition in accordance with the invention, mention may be made more particularly of the compounds described in patent application JP 07 325 375, the teaching of which forms an integral part of the present patent application.

Among the pyrazolo[3,4-d]thiazole derivatives which may be used as heterocyclic couplers in the dye composition in accordance with the invention, mention may be made more particularly of compounds described in patent application JP 07 244 361 and in J. Heterocycl. Chem. 16, 13, (1979).

Among the thiazoloazole S-oxide and thiazoloazole S,S-dioxide derivatives which may be used as heterocyclic couplers in the dye composition in accordance with the invention, mention may be made more particularly of the compounds described in the following documents:

JP 07 098 489;
Khim. Geterotsikl. Soedin, 1967, p. 93;
J. Prakt. Chem., 318, 1976, p. 12;
Indian J. Heterocycl. Chem. 1995, 5 (2), p. 135;
Acta. Pol. Pharm. 1995, 52 (5), 415;
Heterocycl. Commun. 1995, 1 (4), 297;
Arch. Pharm. (Weinheim, Ger.), 1994, 327 (12), 825.

Among the naphthols and acylated naphthols which may be used as couplers in the dye composition in accordance with the invention, the compounds which will preferably be used are those of formula (X) below, and the addition salts thereof with an acid:

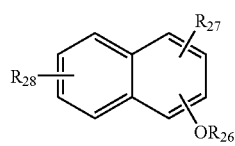

(X)

in which:
$R_{26}$ represents a hydrogen atom or a group —CO—R in which R represents a $C_1$–$C_4$ alkyl radical;
$R_{27}$ represents a hydrogen atom, a hydroxyl or $C_1$–$C_4$ alkyl radical or an —$SO_3H$ group;
$R_{28}$ represents a hydrogen atom or a hydroxyl radical; it being understood that at least one of the radicals $R_{26}$ to $R_{28}$ is other than a hydrogen atom.

Among the naphthols and acylated naphthols of formula (X) which may be used as couplers in the dye composition in accordance with the invention, mention may be made especially of 1,7-dihydroxynaphthalene, 2,7-dihydroxynaphthalene, 2,5-dihydroxynaphthalene, 2,3-dihydroxynaphthalene, 1-acetoxy-2-methylnaphthalene, 1-hydroxy-2-methylnaphthalene and 1-hydroxy-4-naphthalenesulfonic acid, and the addition salts thereof with an acid.

When they are present, the coupler(s) preferably represent(s) from 0.0001% to 10% by weight approximately relative to the total weight of the dye composition, and even preferentially from 0.005% to 5% by weight approximately relative to this weight.

The dye composition in accordance with the invention may furthermore also contain at least one additional oxidation base, which may be chosen from the oxidation bases conventionally used in oxidation dyeing, and among which mention may be made especially of para-phenylenediamines other than the compounds of formula (I) in accordance with the invention, bis(phenyl)alkylenediamines, para-aminophenols, ortho-aminophenols and heterocyclic bases, and the addition salts thereof with an acid.

According to one particular embodiment, the addition base is chosen from heterocyclic oxidation bases, double bases, substituted para-aminophenols, ortho-aminophenols, the para-phenylenediamine derivatives of formula (II) below, and the addition salts thereof with an acid:

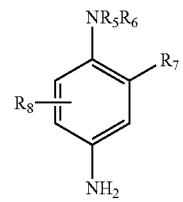

(II)

in which:
$R_5$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical, a $C_1$–$C_4$ alkyl radical substituted with one or more nitrogenous groups, a phenyl radical or a 4'-aminophenyl radical;
$R_6$ represents a hydrogen atom, a $C_1$–$C_4$ alkyl radical, a $C_1$–$C_4$ monohydroxyalkyl radical, a $C_2$–$C_4$ polyhydroxyalkyl radical, a ($C_1$–$C_4$)alkoxy($C_1$–$C_4$)alkyl radical or a $C_1$–$C_4$ alkyl radical substituted with one or more nitrogenous groups;
$R_7$ represents a hydrogen atom, a halogen atom such as a chlorine, bromine, iodine or fluorine atom, a $C_1$–$C_4$ alkyl radical, a $C_1$–$C_4$ monohydroxyalkyl radical, a $C_1$–$C_4$ hydroxyalkoxy radical, an acetylamino($C_1$–$C_4$) alkoxy radical, a $C_1$–$C_4$ mesylaminoalkoxy radical or a carbamoylamino ($C_1$–$C_4$) alkoxy radical,
$R_8$ represents a hydrogen or halogen atom or a $C_1$–$C_4$ alkyl radical.

Among the para-phenylenediamines of formula (II) which can be used as additional oxidation bases in the dye composition in accordance with the invention, mention may be made more particularly of 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-amino-N,N-bis(β-hydroxyethyl)-2-methylaniline, 4-amino-2-chloro-N,N-bis(β-hydroxyethyl)aniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl-β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylamino-ethyloxy-para-phenylenediamine and N-(β-methoxyethyl)-para-phenylenediamine, and the addition salts thereof with an acid.

Among the para-phenylenediamines of formula (II) above, 2-isopropyl-para-phenylenediamine, 2-β-hydroxyethyl-para-phenylenediamine, 2-β-hydroxy-ethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxy-ethyl)-para-phenylenediamine, and 2-β-acetylamino-ethyloxy-para-phenylenediamine and the addition salts thereof with an acid are most particularly preferred.

Even more preferentially, 2-β-hydroxyethyl-para-phenylenediamine, N,N-bis(β-hydroxyethyl)-para-phenylenediamine, and the addition salts thereof with an acid, are preferred among the para-phenylenediamines of formula (II) above.

According to the invention, the term "double bases" is understood to refer to the compounds containing at least two aromatic rings bearing amino and/or hydroxyl groups.

Among the double bases which can be used as additional oxidation bases in the dye composition in accordance with the invention, mention may be made in particular of the double bases corresponding to formula (III) below, and the addition salts thereof with an acid:

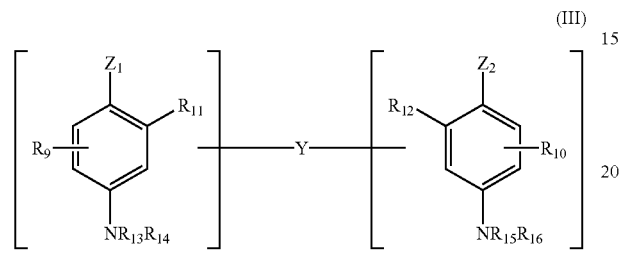

in which:
- $Z_1$ and $Z_2$, which may be identical or different, represent a hydroxyl or —$NH_2$ radical which may be substituted with a $C_1$–$C_4$ alkyl radical or with a linker arm Y;
- the linker arm Y represents a linear or branched alkylene chain containing from 1 to 14 carbon atoms, which may be interrupted or terminated with one or more nitrogenous groups and/or one or more hetero atoms such as oxygen, sulfur or nitrogen atoms, and optionally substituted with one or more hydroxyl or $C_1$–$C_6$ alkoxy radicals;
- $R_9$ and $R_{10}$ represent a hydrogen or halogen atom, a $C_1$–$C_4$ alkyl radical, a $C_1$–$C_4$ monohydroxyalkyl radical, a $C_2$–$C_4$ polyhydroxyalkyl radical, a $C_1$–$C_4$ aminoalkyl radical or a linker arm Y;
- $R_{11}$, $R_{12}$, $R_{13}$, $R_{14}$, $R_{15}$ and $R_{16}$, which may be identical or different, represent a hydrogen atom, a linker arm Y or a $C_1$–$C_4$ alkyl radical; it being understood that the double bases of formula (III) contain only one linker arm Y per molecule.

Among the nitrogenous groups present in the double base of formula (III) above, mention may be made in particular of amino, mono($C_1$–$C_4$)alkylamino, di($C_1$–$C_4$)alkylamino, tri($C_1$–$C_4$)alkylamino, monohydroxy($C_1$–$C_4$)alkylamino, imidazolinium and ammonium radicals.

Among the double bases of formula (III) above, mention may be made more particularly of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)-tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,5-dioxaoctane, and the addition salts thereof with an acid.

Among these double bases of formula (III), N,N'-bis(β-hydroxyethyl)-N,N'-bis(4'-aminophenyl)-1,3-diaminopropanol, 1,8-bis(2,5-diaminophenoxy)-3,5-dioxaoctane, or one of the addition salts thereof with an acid, are particularly preferred.

Among the substituted para-aminophenols which can be used as second oxidation base in the dye composition in accordance with the invention, mention may be made in particular of the substituted para-aminophenols of formula (IV) below, and the addition salts thereof with an acid:

in which:
- $R_{17}$ represents a hydrogen or halogen atom or a $C_1$–$C_4$ alkyl, $C_1$–$C_4$ monohydroxyalkyl, ($C_1$–$C_4$)alkoxy ($C_1$–$C_4$)alkyl, $C_1$–$C_4$ aminoalkyl or hydroxy($C_1$–$C_4$) alkylamino ($C_1$–$C_4$) alkyl radical,
- $R_{18}$ represents a hydrogen or halogen atom or a $C_1$–$C_4$ alkyl, $C_1$–$C_4$ monohydroxyalkyl, $C_2$–$C_4$ polyhydroxyalkyl, $C_1$–$C_4$ aminoalkyl, $C_1$–$C_4$ cyanoalkyl or ($C_1$–$C_4$) alkoxy-($C_1$–$C_4$)alkyl radical, it being understood that at least one of the radicals $R_{17}$ or $R_{18}$ is other than a hydrogen atom.

Among the para-aminophenols of formula (IV) above, mention may be made more particularly of para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(p-hydroxyethylaminomethyl)phenol, 4-amino-2-fluorophenol, and the addition salts thereof with an acid.

Among the ortho-aminophenols which can be used as additional oxidation bases in the dye compositions in accordance with the invention, mention may be made more particularly of 2-aminophenol, 2-amino-5-methylphenol, 2-amino-6-methylphenol and 5-acetamido-2-aminophenol, and the addition salts thereof with an acid.

Among the heterocyclic bases which can be used as oxidation bases in the dye compositions in accordance with the invention, mention may be made more particularly of pyridine derivatives, pyrimidine derivatives, pyrazole derivatives, and the addition salts thereof with an acid.

Among the pyridine derivatives, mention may be made more particularly of the compounds described, for example, in patents GB 1 026 978 and GB 1 153 196, such as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid.

Among the pyrimidine derivatives, mention may be made more particularly of the compounds described, for example, in German patent DE 2 359 399 or Japanese patents JP 88-169 571 and JP 05 163 124; European Patent 0 770 375 or patent application WO 96/15765, such as 2,4,5,6-tetramino-pyrimidine, 4-hydroxy-2,5,6-triaminopyrimidine, 2-hydroxy-4,5,6-triaminopyrimidine, 6-hydroxy-2,4,5-triaminopyrimidine 2,4-dihydroxy-5,6-diaminopyrimidine, 2,5,6-triaminopyrimidine and pyrazolopyrimidine derivatives such as those mentioned in patent application FR-A-2 750 048, and among which mention may be made of pyrazolo[1,5-a]pyrimidine-3,7-diamine;

2,5-dimethylpyrazolo[1,5-a]pyrimidine-3,7-diamine;
pyrazolo[1,5-a]pyrimidine-3,5-diamine;
2,7-dimethylpyrazolo[1,5-a]pyrimidine-3,5-diamine;
3-aminopyrazolo[1,5-a]pyrimidin-7-ol;
3-aminopyrazolo[1,5-a]pyrimidin-5-ol;
2-(3-aminopyrazolo[1,5-a]pyrimidin-7-ylamino)ethanol;
2-(7-aminopyrazolo[1,5-a]pyrimidin-3-ylamino)ethanol,
2-[(3-aminopyrazolo[1,5-a]pyrimidin-7-yl)-(2-hydroxyethyl)amino]ethanol, 2-[(7-amino-pyrazol[1,5-a]pyrimidin-3-yl)-(2-hydroxyethyl)amino]-ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a-[pyrimidine-3,7-diamine, 3-amino-5-methyl-7-imidazolylpropylaminopyrazolo[1,5-a]pyrimidine, the addition salts thereof with an acid, and the tautomeric forms thereof, when a tautomeric equilibrium exists.

Among the pyrazole derivatives, mention may be made more particularly of the compounds described in patents DE 3 843 892, DE 4 133 957 and patent applications WO 94/08969, WO 94/08970, FR-A-2 733 749 and DE 195 43 988, such as 4,5-diamino-1-methylpyrazole, 3,4-diaminopyrazole, 4,5-diamino-1-(4'-chlorobenzyl)pyrazole, 4,5-diamino-1,3-dimethyl-pyrazole, 4,5-diamino-1-(β-hydroxyethyl)pyrazole 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof with an acid.

When they are used, the additional oxidation base(s) preferably represent(s) from 0.0005% to 12% by weight approximately relative to the total weight of the dye composition, and even more preferentially from 0.005% to 6% by weight approximately relative to this weight.

In general, the addition salts with an acid which may be used in the context of the dye compositions of the invention (compounds of formula (I), couplers and additional oxidation bases) are chosen especially from the hydrochlorides, hydrobromides, sulfates, citrates, succinates, tartrates, lactates, phosphates and acetates.

The dye composition in accordance with the invention may also contain one or more direct dyes. This direct dye may be a synthetic direct dye chosen from azo dyes, quinone dyes, triarylmethane dyes, indoamine dyes and azine dyes and/or a natural dye. The synthetic direct dyes which may be used according to the invention may be nonionic, anionic or cationic.

Among the synthetic azo direct dyes which may be used according to the invention, mention may be made of cationic azo dyes described in patent applications WO 95/15144, WO 95/01772 and EP-714 954, the content of which forms an integral part of the invention.

Among the azo direct dyes, mention may also be made of the following dyes, described in the Colour Index International 3rd edition: Disperse Red 17, Acid Yellow 9, Acid Black 1, Basic Red 22, Basic Red 76, Basic Yellow 57, Basic Brown 16, Acid Yellow 36, Acid Orange 7, Acid Red 33, Acid Red 35, Basic Brown 17, Acid Yellow 23, Acid Orange 24, Disperse Black 9. Among these, mention may also be made of 1-(4'-aminodiphenyl-azo)-2-methyl-4-bis(β-hydroxyethyl)aminobenzene and 4-hydroxy-3-(2-methoxyphenylazo)-1-naphthalene sulfonic acid.

Among the synthetic quinone direct dyes, mention may be made of the following: Disperse Red 15, Solvent Violet 13, Acid Violet 43, Disperse Violet 1, Disperse Violet 4, Disperse Blue 1, Disperse Violet 8, Disperse Blue 3, Disperse Red 11, Acid Blue 62, Disperse Blue 7, Basic Blue 22, Disperse Violet 15, Basic Blue 99, and also the compounds:
1-N-methylmorpholiniumpropylamino-4-hydroxyanthraquinone,
1-aminopropylamino-4-methylaminoanthraquinone,
1-aminopropylaminoanthraquinone,
5-β-hydroxyethyl-1,4-diaminoanthraquinone,
2-aminomethylaminoanthraquinone,
1,4-bis(β,γ-dihydroxypropylamino)anthraquinone.

Among the synthetic azine direct dyes, mention may be made of the following: Basic Blue 17, Basic Red 2.

Among the synthetic triarylmethane direct dyes which may be used according to the invention, mention may be made of the following: Basic Green 1, Acid Blue 9, Basic Violet 3, Basic Violet 14, Basic Blue 7, Acid Violet 49, Basic Blue 26, Acid Blue 7.

Among the synthetic indoamine direct dyes which may be used according to the invention, mention may be made of the following:
2-β-hydroxyethylamino-5-[bis(β-4'-hydroxyethyl)-amino]anilino-1,4-benzoquinone
2-β-hydroxyethylamino-5-(2'-methoxy-4'-amino)anilino-1,4-benzoquinone
3-N-(2'-chloro-4'-hydroxy)phenylacetylamino-6-methoxy-1,4-benzoquinoneimine
3-N-(3'-chloro-4'-methylamino)phenylureido-6-methyl-1,4-benzoquinoneimine
3-[4'-N-(ethylcarbamylmethyl)amino]phenylureido-6-methyl-1,4-benzoquinoneimine.

For the purposes of the invention, the term "natural dye" means compounds which exist in nature, whether they have been obtained by extraction or reproduced chemically. Among the natural direct dyes which may be used according to the invention, mention may be made of lawsone, juglone, alizarin, purpurine, carminic acid, kermesic acid, purpurogallin, protocatechaldehyde, indigo, isatin, curcumin, spinulosin and apigenidin. Extracts or decoctions containing these natural dyes, and especially henna-based poultices or extracts, may also be used.

The synthetic direct dye(s) according to the invention and/or the natural dye(s) represent(s) from 0.001% to 20% by weight approximately relative to the total weight of the composition, and even more preferentially from 0.005% to 10% by weight approximately.

The dye composition in accordance with the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, mineral or organic thickeners, antioxidants, penetration agents, sequestering agents, fragrances, buffers, dispersants, conditioners such as, for example, volatile or non-volatile silicones, modified or unmodified silicones, film-forming agents, ceramides, preserving agents and opacifiers.

According to one particular embodiment, the dye composition of the invention comprises at least one polymer chosen from:
(i) amphoteric polymers,
(ii) cationic polymers containing repeating units of structures (II) or (III) below, and
(iii) polymers other than the above, which are amphiphilic and comprise at least one fatty chain, Structure (II):

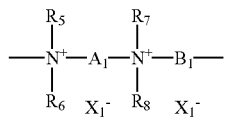

(II)

in which:

$R_5$, $R_6$, $R_7$ and $R_8$, which may be identical or different, represent aliphatic, alicyclic or arylaliphatic radicals containing from 1 to 20 carbon atoms or lower hydroxyalkylaliphatic radicals, or alternatively $R_5$, $R_6$, $R_7$ and $R_8$, together or separately, constitute, with the nitrogen atoms to which they are attached, heterocycles optionally containing a second heteroatom other than nitrogen, or alternatively $R_5$, $R_6$, $R_7$ and $R_8$ represent a linear or branched $C_1$–$C_6$ alkyl radical substituted with a nitrile, ester, acyl, amide or —CO—O—$R_{13}$—D or —CO—NH—$R_{13}$—D group in which $R_{13}$ is an alkylene and D is a quaternary ammonium group;

$A_1$ and $B_1$ represent polymethylene groups containing from 2 to 20 carbon atoms which may be linear or branched, saturated or unsaturated and which may contain, linked to or intercalated in the main chain, one or more aromatic rings, or one or more oxygen or sulfur atoms or sulfoxide, sulfone, disulfide, amino, alkylamino, hydroxyl, quaternary ammonium, ureido, amide or ester groups.

$A_1$, $R_5$ and $R_7$ may form with the two nitrogen atoms to which they are attached a piperazine ring; in addition, if $A_1$ denotes a linear or branched, saturated or unsaturated alkylene or hydroxyalkylene radical, $B_1$ can also denote a group —$(CH_2)_n$—CO—T—OC—$(CH_2)_n$— in which n is between 1 and 100 and preferably between 1 and 50, and T denotes:
a) a glycol residue of formula: —O—Z—O—, in which Z denotes a linear or branched hydrocarbon-based radical or a group corresponding to one of the following formulae:

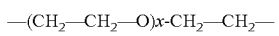

—[$CH_2$—$CH(CH_3)$—O]$y$-$CH_2$—$CH(CH_3)$— in which x and y denote an integer from 1 to 4, representing a defined and unique degree of polymerization, or any number from 1 to 4 representing an average degree of polymerization;
b) a bis-secondary diamine residue such as a piperazine derivative;
c) a bis-primary diamine residue of formula: —NH—Y—NH—, in which Y denotes a linear or branched hydrocarbon-based radical, or alternatively the divalent radical

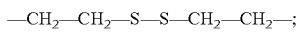

d) a ureylene group of formula: —NH—CO—NH—;

$X_1^-$ is an anion derived from a mineral or organic acid and preferably chlorine or bromine;

Structure (III)

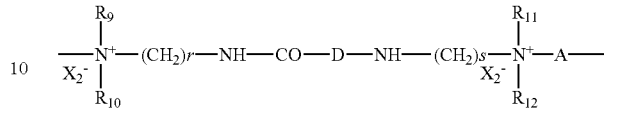

(III)

in which:

$R_9$, $R_{10}$, $R_{11}$ and $R_{12}$, which may be identical or different, represent a hydrogen atom or a methyl, ethyl, propyl, β-hydroxyethyl, β-hydroxypropyl or —$CH_2CH_2$($OCH_2CH_2$)$p$OH radical, in which p is equal to 0 or to an integer between 1 and 6, with the proviso that $R_9$, $R_{10}$, $R_{11}$ and $R_{12}$ do not simultaneously represent a hydrogen atom, r and s, which may be identical or different, are integers between 1 and 6, D is zero or denotes a group —$(CH_2)_q$—CO— in which q is zero or equal to an integer between 1 and 34, A denotes a dihalide radical or, preferably, represents —$CH_2$—$CH_2$—O—$CH_2$—$CH_2$—, $X_2^-$ denotes an anion derived from a mineral or organic acid, preferably a halogen atom.

The cationic polymers containing repeating units of structure (II) preferably have a number-average molecular mass generally between 1 000 and 100 000.

Polymers of this type are especially described in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

According to the invention, among these cationic polymers containing units of structure (II), those more particularly used are those consisting of repeating units corresponding to structure (IV) below:

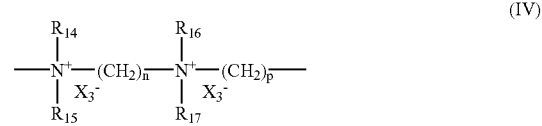

(IV)

in which $R_{14}$, $R_{15}$, $R_{16}$ and $R_{17}$, which may be identical or different, denote an alkyl or hydroxyalkyl radical containing from 1 to 4 carbon atoms approximately, n and p are integers ranging from 2 to 20 approximately, and $X_3^-$ is an anion derived from a mineral or organic acid.

More particularly, it is also preferred to use the polymer containing units of structure (IV) in which $R_{14}$, $R_{15}$, $R_{16}$ and $R_{17}$ denote a methyl radical, n and p are equal to 6 and 3, respectively, and $X_3^-$ is equal to Cl$^-$; this polymer has the INCI name: Hexadimethrine Chloride.

The cationic polymers containing repeating units of structure (III) are especially described in patent application EP-A-122 324 and may be prepared according to the processes described in U.S. Pat. Nos. 4,157,388, 4,390,689, 4,702,906 and 4,719,282.

Among these polymers, it is more particularly preferred according to the invention to use those consisting of repeating units corresponding to structure (V) below:

$$-[-N^+(CH_3)_2-(CH_2)_r-NH-CO-D-NH-(CH_2)_r-N^+(CH_3)_2-(CH_2)_2-O-(CH_2)_2]- \quad 2X^-$$  (V)

in which r denotes an integer ranging from 1 to 6 approximately, D may be 0 or may represent a group $-(CH_2)_q-CO-$ in which q denotes a number equal to 4 or to 7, and $X^-$ is an anion derived from a mineral or organic acid, and preferably with a molecular mass, measured by carbon-13 NMR, of less than 100 000.

Among the cationic polymers of structure (V) which are even more particularly preferred are those for which:
a) D represents a group $-(CH_2)_4-CO-$, X denotes a chlorine atom, the molecular mass, measured by carbon-13 NMR ($C^{13}$ NMR), being about 5 600; a polymer of this type is proposed by the company Miranol under the name Mirapol-AD1,
b) D represents a group $-(CH_2)_7-CO-$ and X denotes a chlorine atom, the molecular mass, measured by carbon-13 NMR ($C^{13}$NMR) being about 8100; a polymer of this type is proposed by the company Miranol under the name Mirapol-AZ1,
c) D denotes the value zero and X denotes a chlorine atom, the molecular mass, measured by carbon-13 NMR ($C^{13}$ NMR), being about 25 500; a polymer of this type is sold by the company Miranol under the name Mirapol-A15,
d) a "block copolymer" formed from units corresponding to the polymers described in paragraphs a) and c), sold by the company Miranol under the names Mirapol-9 ($C^{13}$ NMR molecular mass of about 7 800) Mirapol-175 ($C^{13}$ NMR molecular mass of about 8 000) and Mirapol-95 ($C^{13}$ NMR molecular mass of about 12 500).

Even more particularly, the polymer which is preferred according to the invention is the polymer of formula (V) in which D denotes the value zero, X denotes a chlorine atom, the molecular mass, measured by carbon-13 NMR ($C^{13}$ NMR), being about 25 500.

According to the invention, the cationic polymer(s) can represent from 0.01% to 10% by weight approximately relative to the total weight of the composition, preferably from 0.05% to 5% and even more preferentially from 0.1% to 3%.

The amphoteric polymers which can be used in accordance with the present invention can be chosen from polymers containing units K and M distributed randomly in the polymer chain, in which K denotes a unit derived from a monomer containing at least one basic nitrogen atom and M denotes a unit derived from an acid monomer containing one or more carboxylic or sulfonic groups, or alternatively K and M can denote groups derived from carboxybetaine or sulfobetaine zwitterionic monomers;

K and M can also denote a cationic polymer chain containing primary, secondary, tertiary or quaternary amine groups, in which at least one of the amine groups bears a carboxylic or sulfonic group connected via a hydrocarbon-based radical, or alternatively K and M form part of a chain of a polymer containing an α,β-dicarboxylic ethylene unit in which one of the carboxylic groups has been made to react with a polyamine containing one or more primary or secondary amine groups.

The amphoteric polymers which are more particularly preferred are chosen from the following polymers:
(1) Polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides. Such compounds are described in U.S. Pat. No. 3,836,537. Mention may also be made of the sodium acrylate/acrylamidopropyltrimethylammonium chloride copolymer sold under the name Polyquart KE 3033 by the company Henkel.

The substituted vinyl compound which contains at least one basic atom can also be a dialkyldiallylammonium salt such as dimethyldiallylammonium chloride. The copolymers of acrylic acid and of the latter monomer are sold under the names Merquat 280, Merquat 295 and Merquat Plus 3330 by the company Calgon.
(2) Polymers containing units derived from:
a) at least one monomer chosen from acrylamides and methacrylamides substituted on the nitrogen with an alkyl radical,
b) at least one acidic comonomer containing one or more reactive carboxylic groups, and
c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides which are more particularly preferred according to the invention are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid, fumaric acid and alkyl monoesters, having 1 to 4 carbon atoms, or maleic or fumaric acids or anhydrides.

The preferred basic comonomers are aminoethyl, butylaminoethyl, N,N'-dimethylaminoethyl and N-tert-butylaminoethyl methacrylates.

The copolymers whose CTFA (4th edition, 1991) name is octylacrylamide/acrylates/butylaminoethyl methacrylate copolymer such as the products sold under the name Amphomer or Lovocryl 47 by the company National Starch are particularly used.
(3) Crosslinked and alkylated polyamino amides partially or totally derived from polyamino amides of general formula:

$$-[CO-R-CO-Z]-$$ (VI)

in which $R_{18}$ represents a divalent radical derived from a saturated dicarboxylic acid, a mono- or dicarboxylic aliphatic acid containing an ethylenic double bond, an ester of a lower alkanol, having 1 to 6 carbon atoms of these acids or a radical derived from the addition of any one of said acids to a bis(primary) or bis(secondary) amine, and Z denotes a bis(primary), mono- or bis(secondary) polyalkylene-polyamine radical and preferably represents:

a) in proportions of from 60 to 100 mol %, the radical

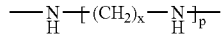
(VII)

where x=2 and p=2 or 3, or alternatively x=3 and p=2
this radical being derived from diethylenetriamine, from triethylenetetraamine or from dipropylenetriamine;

b) in proportions of from 0 to 40 mol %, the radical (VII) above, in which x=2 and p=1 and which is derived from ethylenediamine, or the radical derived from piperazine:

c) in proportions of from 0 to 20 mol %, the —NH—(CH$_2$)$_6$—NH— radical derived from hexamethylenediamine, these polyamino amines being crosslinked by addition of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids having 6 to 10 carbon atoms, such as adipic acid, 2,2,4-trimethyladipic acid and 2,4,4-trimethyladipic acid, terephthalic acid, acids containing an ethylenic double bond such as, for example, acrylic acid, methacrylic acid and itaconic acid.

The alkane sultones used in the alkylation are preferably propane sultone or butane sultone, the salts of the alkylating agents are preferably the sodium or potassium salts.

(4) Polymers containing zwitterionic units of formula:

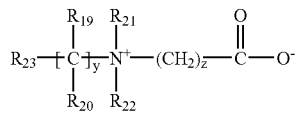
(VIII)

in which R$_{23}$ denotes a polymerizable unsaturated group such as an acrylate, methacrylate, acrylamide or methacrylamide group, y and z represent an integer from 1 to 3, R$_{19}$ and R$_{20}$ represent a hydrogen atom, methyl, ethyl or propyl, R$_{21}$ and R$_{22}$ represent a hydrogen atom or an alkyl radical such that the sum of the carbon atoms in R$_{21}$ and R$_{22}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate.

By way of example, mention may be made of the copolymer of butyl methacrylate/dimethyl carboxymethylammonio ethyl methacrylate such as the product sold under the name Diaformer Z301 by the company Sandoz.

(5) Polymers derived from chitosan containing monomer units corresponding to the following formulae (IX), (X) and (XI):

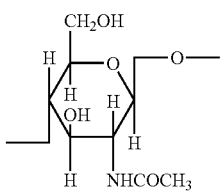
(IX)

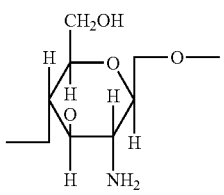
(X)

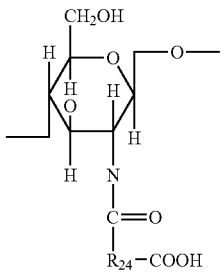
(XI)

the unit (IX) being present in proportions of between 0 and 30%, the unit (X) in proportions of between 5 and 50% and the unit (XI) in proportions of between 30 and 90%, it being understood that, in this unit (XI), R$_{24}$ represents a radical of formula:

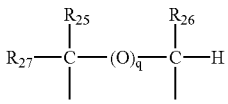

in which if q=0, R$_{25}$, R$_{26}$ and R$_{27}$, which may be identical or different, each represent a hydrogen atom, a methyl, hydroxyl, acetoxy or amino residue, a monoalkylamine residue or a dialkylamine residue which are optionally interrupted by one or more nitrogen atoms and/or optionally substituted with one or more amine, hydroxyl, carboxyl, alkylthio or sulfonic groups, an alkylthio residue in which the alkyl group bears an amino residue, at least one of the radicals R$_{25}$, R$_{26}$ and R$_{27}$ being, in this case, a hydrogen atom;

or, if q=1, R$_{25}$, R$_{26}$ and R$_{27}$ each represent a hydrogen atom, as well as the salts formed by these compounds with bases or acids.

(6) Polymers derived from the N-carboxyalkylation of chitosan, such as N-carboxymethylchitosan or N-carboxybutylchitosan sold under the name "Evalsan" by the company Jan Dekker.

(7) Polymers corresponding to the general formula (XII) are described, for example, in French patent 1 400 366:

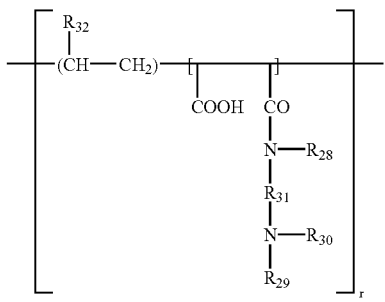

in which $R_{32}$ represents a hydrogen atom, a $CH_3O$, $CH_3CH_2O$ or phenyl radical, $R_{28}$ denotes hydrogen or a lower alkyl radical such as methyl or ethyl, $R_{29}$ denotes hydrogen or a lower alkyl radical such as methyl or ethyl, $R_{30}$ denotes a lower alkyl radical such as methyl or ethyl or a radical corresponding to the formula: $-R_{31}-N(R_{29})_2$, $R_{31}$ representing a $-CH_2-CH_2-$, $-CH_2-CH_2-CH_2-$ or $-CH_2-CH(CH_3)-$ group, $R_{29}$ having the meanings mentioned above, as well as the higher homologs of these radicals and containing up to 6 carbon atoms.

r is such that the molecular weight is between 500 and 6 000 000 and preferably between 1 000 and 1 000 000.

(8) Amphoteric polymers of the type -D-X-D-X chosen from:

a) polymers obtained by the action of chloroacetic acid or sodium chloroacetate on compounds containing at least one unit of formula:

-D-X-D-X-D- (XIII)

where D denotes a radical

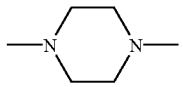

and X denotes the symbol E or E'. E or E', which may be identical or different, denote a divalent radical which is an alkylene radical containing a straight or branched chain containing up to 7 carbon atoms in the main chain, which is unsubstituted or substituted with hydroxyl groups and which can contain, in addition to the oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups.

b) polymers of formula:

-D-X-D-X- (XIV)

in which D denotes a radical

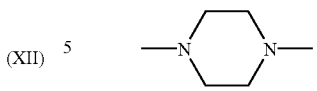

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) ($C_1$–$C_5$)alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also contain other vinyl comonomers such as vinylcaprolactam.

The amphoteric polymers which are particularly preferred according to the invention are those of family (1).

According to the invention, the amphoteric polymer(s) can represent from 0.01% to 10% by weight, preferably from 0.05% to 5% by weight and even more preferably from 0.1% to 3% by weight, relative to the total weight of the composition.

The polymers other than the above which are amphiphilic and contain at least one fatty chain, which are useful in the present invention, are also known as associative polymers; they may be of nonionic, anionic or cationic type.

Among the amphiphilic polymers comprising at least one fatty chain and of anionic type, mention may be made of:

(I) those comprising at least one hydrophilic unit and at least one allyl ether unit containing a fatty chain, more particularly those of which the hydrophilic unit consists of an ethylenic unsaturated anionic monomer, even more particularly a vinylcarboxylic acid and most particularly an acrylic acid, a methacrylic acid or mixtures thereof, the allyl ether unit containing a fatty chain corresponding to the monomer of formula (XV) below:

$CH_2=CR'CH_2OB_nR$ (XV)

in which R' denotes H or $CH_3$, B denotes an ethyleneoxy radical, n is zero or denotes an integer ranging from 1 to 100, R denotes a hydrocarbon-based radical chosen from alkyl, arylalkyl, aryl, alkylaryl and cycloalkyl radicals, containing 8 to 30 carbon atoms, preferably 10 to 24 carbon atoms and even more particularly from 12 to 18 carbon atoms. A unit of formula (XV) which is more particularly preferred is a unit in which R' denotes H, n is equal to 10 and R denotes a stearyl ($C_{18}$) radical.

Anionic amphiphilic polymers of this type are described and prepared, according to an emulsion polymerization process, in patent EP-0 216 479.

Among these fatty-chain anionic polymers, those which are particularly preferred according to the invention are polymers formed from 20% to 60% by weight of acrylic acid and/or of methacrylic acid, from 5% to 60% by weight of lower alkyl (meth)acrylates, from 2% to 50% by weight of allyl ether containing a fatty chain of formula (XV), and from 0% to 1% by weight of a crosslinking agent which is a well-known copolymerizable unsaturated polyethylenic monomer, for instance diallyl phthalate, allyl (meth)acrylate, divinylbenzene, (poly)ethylene glycol dimethacrylate or methylenebisacrylamide.

Among the latter polymers, those most particularly preferred are crosslinked terpolymers of methacrylic acid, of ethyl acrylate and of polyethylene glycol (10 EO) stearyl ether (Steareth-10), in particular those sold by the company Allied Colloids under the names Salcare SC 80 and Salcare SC 90, which are aqueous 30% emulsions of a crosslinked terpolymer of methacrylic acid, of ethyl acrylate and of steareth-10 allyl ether (40/50/10).

(II) those comprising at least one hydrophilic unit of unsaturated olefinic carboxylic acid type, and at least one hydrophobic unit of $(C_{10}-C_{30})$alkyl ester of unsaturated carboxylic acid type.

Preferably, these polymers are chosen from those in which the hydrophilic unit of unsaturated olefinic carboxylic acid type corresponds to the monomer of formula (XVI) below:

(XVI)

in which $R_1$ denotes H or $CH_3$ or $C_2H_5$, that is to say acrylic acid, methacrylic acid or ethacrylic acid units, and in which the hydrophobic unit of $(C_{10}-C_{30})$alkyl ester of unsaturated carboxylic acid type corresponds to the monomer of formula (XVII) below:

(XVII)

in which $R_2$ denotes H or $CH_3$ or $C_2H_5$ (that is to say acrylate, methacrylate or ethacrylate units) and preferably H (acrylate units) or $CH_3$ (methacrylate units), $R_3$ denoting a $C_{10}-C_{30}$ and preferably $C_{12}-C_{22}$ alkyl radical.

$(C_{10}-C_{30})$ alkyl esters of unsaturated carboxylic acids according to the invention include, for example, lauryl acrylate, stearyl acrylate, decyl acrylate, isodecyl acrylate and dodecyl acrylate, and the corresponding methacrylates, lauryl methacrylate, stearyl methacrylate, decyl methacrylate, isodecyl methacrylate and dodecyl methacrylate.

Anionic polymers of this type are described and prepared, for example, according to U.S. Pat. Nos. 3,915,921 and 4,509,949.

Among the fatty-chain anionic polymers of this type which will be used more particularly are polymers formed from a monomer mixture comprising:
(i) essentially acrylic acid,
(ii) an ester of formula (XVI) described above in which $R_2$ denotes H or $CH_3$, $R_3$ denoting an alkyl radical containing from 12 to 22 carbon atoms,
(iii) and a crosslinking agent, which is a well-known copolymerizable polyethylenic unsaturated monomer, for instance diallyl phthalate, allyl (meth)acrylate, divinylbenzene, (poly)ethylene glycol dimethacrylate and methylenebisacrylamide.

Among fatty-chain anionic polymers of this type which will be used more particularly are those consisting of from 95% to 60% by weight of acrylic acid (hydrophilic unit), 4% to 40% by weight of $C_{10}-C_{30}$ alkyl acrylate (hydrophobic unit) and 0% to 6% by weight of crosslinking polymerizable monomer, or alternatively those consisting of from 98% to 96% by weight of acrylic acid (hydrophilic unit), 1% to 4% by weight of $C_{10}-C_{30}$ alkyl acrylate (hydrophobic unit) and 0.1% to 0.6% by weight of crosslinking polymerizable monomer such as those described above.

Among said above polymers, those most particularly preferred according to the present invention are the products sold by the company Goodrich under the trade names Pemulen TR1, Pemulen TR2 and Carbopol 1382, and even more preferentially Pemulen TR1, and the product sold by the company S.E.P.P.I.C under the name Coatex SX.

(III) maleic anhydride/$C_{30}-C_{38}$ α-olefin/alkyl maleate terpolymers, such as the product (maleic anhydride/$C_{30}-C_{38}$ α-olefin/isopropyl maleate copolymer) sold under the name Performa V 1608 by the company Newphase Technologies.

(IV) acrylic terpolymers comprising:
(a) about 20% to 70% by weight of a carboxylic acid containing α,β-monoethylenic unsaturation,
(b) about 20% to 80% by weight of a non-surfactant monomer containing α,β-monoethylenic unsaturation other than (a),
(c) about 0.5% to 60% by weight of a nonionic monourethane which is the product of reaction of a monohydric surfactant with a monoisocyanate containing monoethylenic unsaturation, such as those described in patent application EP-A-0 173 109 and more particularly the terpolymer described in example 3, namely a methacrylic acid/methyl acrylate/behenyl dimethyl-meta-isopropenylbenzylisocyanate ethoxylated (40 EO) terpolymer, as an aqueous 25% dispersion.

(V) copolymers comprising among their monomers a carboxylic acid containing α,β-monoethylenic unsaturation and an ester of a carboxylic acid containing α,β-monoethylenic unsaturation and of a $(C_8-C_{30})$ oxyalkylenated fatty alcohol.

Preferentially, these compounds also comprise as monomer an ester of a carboxylic acid containing α,β-monoethylenic unsaturation and of a $C_1-C_4$ alcohol.

An example of a compound of this type which may be mentioned is Aculyn 22 sold by the company Rohm & Haas, which is a methacrylic acid/ethyl acrylate/stearyl methacrylate oxyalkylenated terpolymer.

The fatty-chain amphiphilic polymers of nonionic type which are used according to the invention are preferably chosen from:

(1) celluloses modified with groups comprising at least one fatty chain;

examples which may be mentioned include:
hydroxyethylcelluloses modified with groups comprising at least one fatty chain, such as alkyl, arylalkyl or alkylaryl groups, or mixtures thereof, and in which the alkyl groups are preferably $C_8-C_{22}$, for instance the product Natrosol Plus Grade 330 CS($C_{16}$ alkyls) sold by the company Aqualon, or the product Bermocoll EHM 100 sold by the company Berol Nobel.
those modified with alkylphenyl polyalkylene glycol ether groups, such as the product Amercell Polymer HM-1500 (nonylphenyl polyethylene glycol (15) ether) sold by the company Amerchol.

(2) hydroxypropylguars modified with groups comprising at least one fatty chain, such as the product Esaflor HM 22 ($C_{22}$ alkyl chain) sold by the company Lamberti, and the products RE210-18 ($C_{14}$ alkyl chain) and RE205-1 ($C_{20}$ alkyl chain) sold by the company Rhône-Poulenc.

(3) copolymers of vinylpyrrolidone and of fatty-chain hydrophobic monomers;

examples which may be mentioned include:
the products Antaron V216 or Ganex V216 (vinylpyrrolidone/hexadecene copolymer) sold by the company I.S.P
the products Antaron V220 or Ganex V220 (vinylpyrrolidone/eicosene copolymer) sold by the company I.S.P.

(4) copolymers of $C_1$–$C_6$ alkyl methacrylates or acrylates and of amphiphilic monomers comprising at least one fatty chain, such as, for example, the oxyethylenated methyl acrylate/stearyl acrylate copolymer sold by the company Goldschmidt under the name Antil 208.

(5) copolymers of hydrophilic methacrylates or acrylates and of hydrophobic monomers comprising at least one fatty chain, such as, for example, the polyethylene glycol methacrylate/lauryl methacrylate copolymer.

(6) polymers with an aminoplast ether skeleton containing at least one fatty chain, such as the Pure Thix compounds sold by the company Sud-Chemie.

(7) polyurethane polyethers comprising in their chain both hydrophilic blocks usually of polyoxyethylenated nature and hydrophobic blocks which may be aliphatic sequences alone and/or cycloaliphatic and/or aromatic sequences, Preferably, the polyether polyurethanes comprising at least two hydrocarbon-based lipophilic chains containing from 6 to 30 carbon atoms, separated by a hydrophilic block, the hydrocarbon-based chains possibly being pendent chains, or chains at the end of the hydrophilic block. In particular, it is possible for one or more pendent chains to be included. In addition, the polymer may comprise a hydrocarbon-based chain at one end or at both ends of a hydrophilic block.

The polyether polyurethanes may be multiblock, in particular in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyether polyurethanes may be triblock copolymers in which the hydrophilic block is a polyoxyethylenated chain comprising from 50 to 1 000 oxyethylene groups. The nonionic polyether polyurethanes comprise a urethane linkage between the hydrophilic blocks, whence arises the name.

By extension, also included among the nonionic fatty-chain polyether polyurethanes are those in which the hydrophilic blocks are linked to the lipophilic blocks via other chemical bonds.

As examples of nonionic fatty-chain polyether polyurethanes which may be used in the invention, mention may also be made of Rheolate 205 containing a urea function, sold by the company Rheox, or the Rheolates 208, 204 or 211, and also Acrysol RM 184, Aculyn or Acrysol 44 and Aculyn or Acrysol 46 from the company Rohm & Haas [Aculyn 46 is a polycondensate of polyethylene glycol containing 150 or 180 mol of ethylene oxide, of stearyl alcohol and of methylenebis(4-cyclohexyl isocyanate) (SMDI), at 15% by weight in a matrix of maltodextrin (4%) and water (81%); Aculyn 44 is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%)].

Mention may also be made of the product Elfacos T210 containing a $C_{12-14}$ alkyl chain, and the product Elfacos T212 containing a $C_{18}$ alkyl chain, from Akzo.

The product DW 1206B from Rohm & Haas containing a $C_{20}$ alkyl chain and urethane linkage, sold at a solids content of 20% in water, may also be used.

It is also possible to use solutions or dispersions of these polymers, especially in water or in aqueous-alcoholic medium. Examples of such polymers which may be mentioned are Rheolate 255, Rheolate 278 and Rheolate 244 sold by the company Rheox. The products DW 1206F and DW 1206J sold by the company Rohm & Haas may also be used.

The polyether polyurethanes which may be used according to the invention are in particular those described in the article by G. Formum, J. Bakke and Fk. Hansen—Colloid Polym. Sci 271, 380.389 (1993).

The amphiphilic polymers of cationic type comprising at least one fatty chain which are used in the present invention are preferably chosen from quaternized cellulose derivatives and polyacrylates containing acyclic amino side groups.

The quaternized cellulose derivatives are, in particular,
quaternized celluloses modified with groups comprising at least one fatty chain, such as alkyl, aralalkyl or alkylaryl groups containing at least 8 carbon atoms, or mixtures thereof.
quaternized hydroxyethylcelluloses modified with groups comprising at least one fatty chain, such as alkyl, aralalkyl or alkylaryl groups containing at least 8 carbon atoms, or mixtures thereof.

The alkyl radicals borne by the above quaternized celluloses or hydroxyethylcelluloses preferably contain from 8 to 30 carbon atoms. The aryl radicals preferably denote phenyl, benzyl, naphthyl or anthryl groups.

Examples of quaternized alkylhydroxyethylcelluloses containing $C_8$–$C_{30}$ fatty chains which may be mentioned include the products Quatrisoft LM 200, Quatrisoft LM-X 529-18-A, Quatrisoft LM-X 529-18B ($C_{12}$ alkyl) and Quatrisoft LM-X 529 8 ($C_{18}$ alkyl) sold by the company Amerchol, and the products Crodacel QM, Crodacel Q1 ($C_{12}$ alkyl) and Crodacel QS ($C_{18}$ alkyl) sold by the company Croda.

The polyacrylates containing quaternized or nonquaternized amino side groups contain, for example, hydrophobic groups of the type such as Steareth 20 (polyoxyethylenated (20) stearyl alcohol).

Examples of polyacrylates containing amino side chains which may be mentioned include the polymers 8781-121B and 9492-103 sold by the company National Starch.

In the oxidation dye composition according to the invention, among the fatty-chain amphiphilic polymers, it is preferred to use an amphiphilic polymer of nonionic or cationic type comprising at least one fatty chain.

According to the invention, the amphiphilic polymer(s) comprising at least one fatty chain may represent about 0.01% to 10% by weight relative to the total weight of the composition. Preferably, this amount ranges from about 0.1% to 5% by weight.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The dye composition according to the invention may be in various forms, such as in the form of liquids, creams or gels or any other form which is suitable for dyeing keratin fibers, and in particular human hair.

A subject of the invention is also a process for dyeing keratin fibers, and in particular human keratin fibers such as the hair, using the dye composition as defined above.

According to this process, at least one dye composition as defined above is applied to the fibers, the color being developed at acidic, neutral or alkaline pH with the aid of an oxidizing agent which is added just at the time of use to the dye composition, or which is present in an oxidizing composition that is applied simultaneously or sequentially.

According to one preferred embodiment of the dyeing process of the invention, the dye composition described above is preferably mixed, at the time of use, with an oxidizing composition containing, in a medium which is suitable for dyeing, at least one oxidizing agent present in an amount which is sufficient to develop a coloration. The mixture obtained is then applied to the keratin fibers and left to stand on them for 3 to 50 minutes approximately, preferably 5 to 30 minutes approximately, after which the fibers are rinsed, washed with shampoo, rinsed again and dried.

The oxidizing agent may be chosen from the oxidizing agents conventionally used for the oxidation dyeing of keratin fibers, and among which mention may be made of hydrogen peroxide, urea peroxide, alkali metal bromates, persalts such as perborates and persulfates, peracids and enzymes, among which mention may be made of peroxidases, 2-electron oxidoreductases such as uricases, and 4-electron oxygenases, for instance laccases. Hydrogen peroxide is particularly preferred.

The pH of the oxidizing composition containing the oxidizing agent as defined above is such that, after mixing with the dye composition, the pH of the resulting composition applied to the keratin fibers preferably ranges between 3 and 12 approximately, and even more preferentially between 5 and 11. It is adjusted to the desired value with the aid of acidifying or basifying agents usually used for the dyeing of keratin fibers and as defined above.

The oxidizing composition as defined above may also contain various adjuvants conventionally used in compositions for dyeing the hair and as defined above.

The composition which is finally applied to the keratin fibers may be in various forms, such as in the form of liquids, creams or gels, or in any other form which is suitable for dyeing keratin fibers, and especially human hair.

Another subject of the invention is a multi-compartment dyeing "kit" or any other multi-compartment packaging system, a first compartment of which contains the dye composition as defined above, and a second compartment of which contains the oxidizing composition as defined above. These devices may be equipped with a means for delivering the desired mixture onto the hair, such as the devices described in patent FR-2 586 913 in the name of the applicant.

Finally, a subject of the invention is also the colored product resulting from the oxidation of at least one compound of formula (I) as defined above in the presence of at least one oxidizing agent as defined above and optionally in the presence of at least one coupler and/or of at least one optional oxidation base.

These colored products may especially be in the form of pigments and may be used as direct dyes for the direct dyeing of the hair, or alternatively may be incorporated into cosmetic products such as, for example, make-up products.

The examples which follow are intended to illustrate the invention.

EXAMPLES OF SYNTHESES

Example 1

(4-Amino-3-methylphenyl)pyrrolidin-3-ylamine dihydrochloride (3)

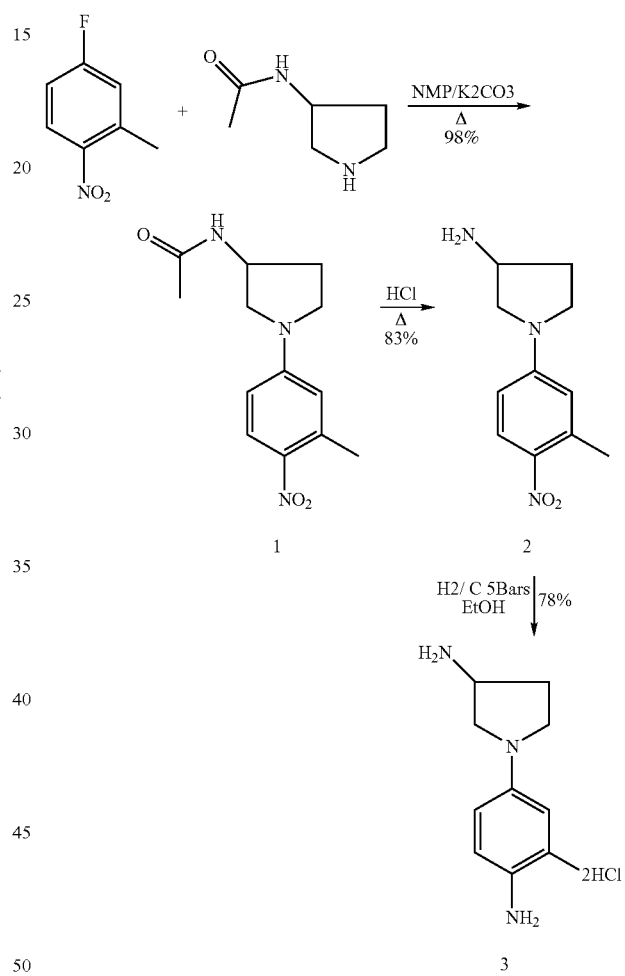

Synthesis of N-[1-(3-methyl-4-nitrophenyl)pyrrolidin-3-yl]acetamide (1)

After dissolving 15.5 g of 5-fluoro-2-nitrotoluene (0.1 mol) and 12.8 g of 3-acetamido-pyrrolidine (0.1 mol) in 75 ml of NMP, 15.8 g of potassium carbonate (0.12 mol) are added under a nitrogen atmosphere and the mixture is heated at 95° C. for 20 h. The reaction medium is allowed to cool and is then poured into 600 ml of saturated aqueous sodium chloride solution. The yellow precipitate formed is filtered off, washed with 15% NaCl solution until a pH equal to 7 is obtained for the washing waters, and washed with petroleum ether and then dried in a vacuum oven over $P_2O_5$. 25.7 g (98%) of N-[1-(3-methyl-4-nitrophenyl)pyrrolidin-3-yl]acetamide are thus obtained in the form of a yellow solid.

Synthesis of 1-(3-methyl-4-nitrophenyl)pyrrolidin-3-ylamine (2)

24 g (0.0911 mol) of N-[1-(3-methyl-4-nitrophenyl)pyrrolidin-3-yl]acetamide (1) are introduced into a solution containing 75 ml of 37% hydrochloric acid and 165 ml of water in a 500 ml three-necked flask. The reaction medium is heated at 90° C. for 2 hours 30 minutes. After cooling, the medium is neutralized carefully with 75 ml of aqueous 35% sodium hydroxide (pH=approximately 8). The resulting solid is then filtered off, after which-it is washed with water until the washing waters are neutral. The product is then dried under vacuum over $P_2O_5$. 16.8 g (83%) of 1-(3-methyl-4-nitrophenyl)pyrrolidin-3-ylamine (2) are thus obtained in the form of a yellow solid.

Synthesis of (4-amino-3-methylphenyl)pyrrolidin-3-ylamine dihydrochloride (3)

16 g of 1-(3-methyl-4-nitrophenyl)pyrrolidin-3-ylamine (2) (72,3 mmol) are partially dissolved in 320 ml of 96° ethanol in a stainless-steel hydrogenation reactor. 4 g of 5% Pd/C (50% water) are added and the reactor is closed and purged with nitrogen 3 times with stirring (1 600 rpm). The hydrogen is then introduced under a pressure of 5–6 bar at ambient temperature. The temperature rises to 35° C. and then falls back to 27° C. over 1 hour. The reactor is then purged with nitrogen and the reaction medium is filtered under a nitrogen atmosphere, and the filtrate is immediately recovered in a solution containing 27 ml of 37% hydrochloric acid and 200 ml of isopropanol. The filtrate is then concentrated until a precipitate is obtained. The solid is filtered off, washed with isopropanol and then with ethyl ether, and dried under vacuum in the presence of potassium hydroxide. 15 g (78%) of (4-amino-3-methylphenyl)pyrrolidin-3-ylamine dihydrochloride (3) are thus obtained in the form of a white solid. The 1H-NMR spectrum and the mass spectrum are in accordance with the spectra for product (3).

| elemental analysis (MW = 264.198; C11H17N3 · 2HCl) | | | | |
|---|---|---|---|---|
| | % C | % H | % N | % Cl |
| Theory | 50.01 | 7.25 | 15.9 | 26.84 |
| Found | 48.29 | 7.84 | 14.23 | 24.37 |

Example 2

1-(4-Amino-3-methoxyphenyl)pyrrolidin-3-ol dihydrochloride (3)

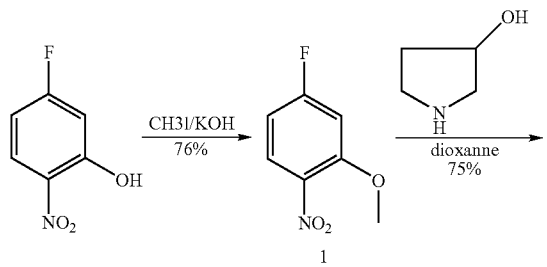

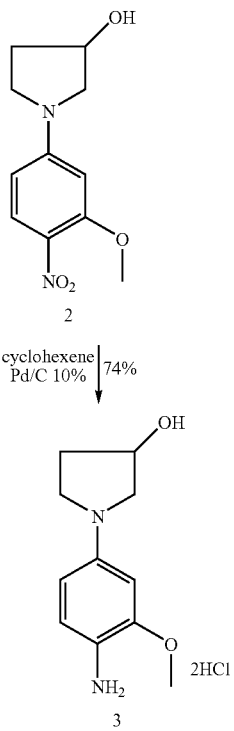

Synthesis of 4-fluoro-2-methoxy-1-nitrobenzene (1)

25 g (0.159 mol) of 5-fluoro-2-nitrophenol are added to 125 ml of DMSO. 22.5 g (0.159 mol) of methyl iodide are then added, followed by dropwise addition, while keeping the temperature below 25° C., of 17.8 g of aqueous 50% potassium hydroxide solution. The mixture is stirred for one hour at ambient temperature and a further 22.5 g (0.159 mol) of methyl iodide are then added. After stirring for 24 hours, the reaction medium is poured into 125 ml of water and then extracted with 60 ml of dichloromethane. The organic phase is washed with 90 ml of aqueous sodium hydroxide solution (1N) and then with 60 ml of water. After drying over $MgSO_4$, the organic phase is concentrated under reduced pressure. 20.59 g (76%) of 4-fluoro-2-methoxy-1-nitrobenzene (1) are thus recovered.

Synthesis of 1-(3-methoxy-4-nitrophenyl)pyrrolidin-3-ol (2)

8 g (46 mmol) of 4-fluoro-2-methoxy-1-nitrobenzene 1,80 ml of dioxane and 8.14 g (0.095 mol) of (R)-(+)-3-pyrrolidinol are respectively placed in the reactor. The mixture is refluxed for one hour. The reaction medium is poured into a mixture of water (100 ml)-ice (200 g). A yellow product precipitates. This product is filtered off, washed with water (3×30 ml) and then dried under vacuum at 45° C. 8.38 g (75%) of 1-(3-methoxy-4-nitrophenyl)pyrrolidin-3-ol (2) are thus recovered.

Synthesis of 1-(4-amino-3-methoxyphenyl)pyrrolidin-3-ol dihydrochloride (3)

12 g (0.05 mol) of 1-(3-methoxy-4-nitro-phenyl)pyrrolidin-3-ol (2), 36 ml of ethanol, 24 ml of cyclohexene and 5.4 g of 10% Pd/C (50% water) are respectively added to the reactor and the reaction medium is then refluxed for 5 hours. The medium is then filtered through Celite, collecting the filtrate onto a 5N hydrochloric ethanol solution. The Celite is washed with ethanol (3×20 ml). The organic phases are combined and then concentrated until a yellow precipitate appears. After cooling to 0° C. and stirring for 1 hour, the product is filtered off, rinsed with water and then dried under vacuum. 10.5 g (74.1%) of 1-(4-amino-3-methoxyphenyl) pyrrolidin-3-ol dihydrochloride (3) are thus recovered in the form of a slightly orange solid. The 1H-NMR spectrum and the mass spectrum are in accordance with the spectra for product (3).

| Elemental analysis (MW = 281.181; C11H16N2O2.2HCl) | | | | | |
|---|---|---|---|---|---|
| | % C | % H | % N | % O | % Cl |
| Theory | 46.99 | 6.45 | 9.96 | 11.38 | 25.25 |
| Found | 46.88 | 6.83 | 9.58 | 11.28 | 24.98 |

Example 3

(R)-1-(4-Aminophenyl)pyrrolidin-3-ol dihydrochloride (2)

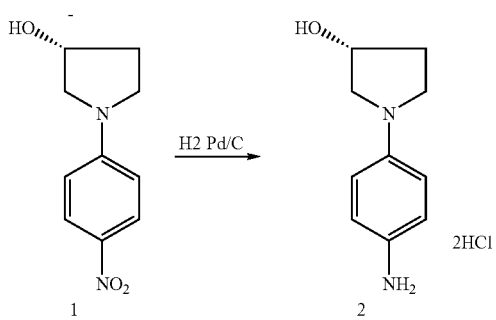

Synthesis of (R)-1-(4-aminophenyl)pyrrolidin-3-ol dihydrochloride (2)

5 g (24 mmol) of (R)-1-(4-nitrophenyl)-pyrrolidin-3-ol and 1 g of palladium on charcoal are introduced, under a gentle stream of nitrogen, into a fully equipped 200 ml stainless-steel hydrogenator. 50 ml of ethanol are then added and the mixture is then stirred at 1 500 rpm while flushing three times with nitrogen and once with hydrogen. Hydrogen is then introduced under a pressure of 5.5 bar. The exothermicity is allowed to develop to 55° C. After one hour 30 minutes, the temperature has fallen back to 31° C. The mixture is purged under nitrogen and then filtered through a closed filter under a nitrogen pressure of 2 bar. The filtrate is recovered in an ice-cold mixture of 7 ml of concentrated hydrochloric acid and 21 ml of isopropanol. The partially crystalline mixture is transferred into a round-bottomed flask with 20 ml of additional isopropanol to be subsequently evaporated therefrom under reduced pressure. After concentrating, the product crystallizes abundantly. Next, 40 ml of isopropanol are added and the mixture is then left stirring overnight while flushing gently with nitrogen. The mixture is then filtered, spin-filtered, washed with 20 ml of isopropanol and dried under high vacuum (~10 mmHg) at a temperature of 40° C. 4.3 g (71%) of (R)-1-(4-aminophenyl) pyrrolidin-3-ol dihydrochloride (2) are thus obtained. The 1H-NMR spectrum and mass spectrum are in accordance with the spectra for product (3).

| | % C | % H | % N | % O | % Cl |
|---|---|---|---|---|---|
| Theory | 47.82 | 6.82 | 11.15 | 6.37 | 28.23 |
| Found | 47.27 | 6.40 | 11.06 | 6.99 | 27.95 |

Example 4

N-[1-(4-Aminophenyl)pyrrolidin-3-yl]-acetamide dihydrochloride (2)

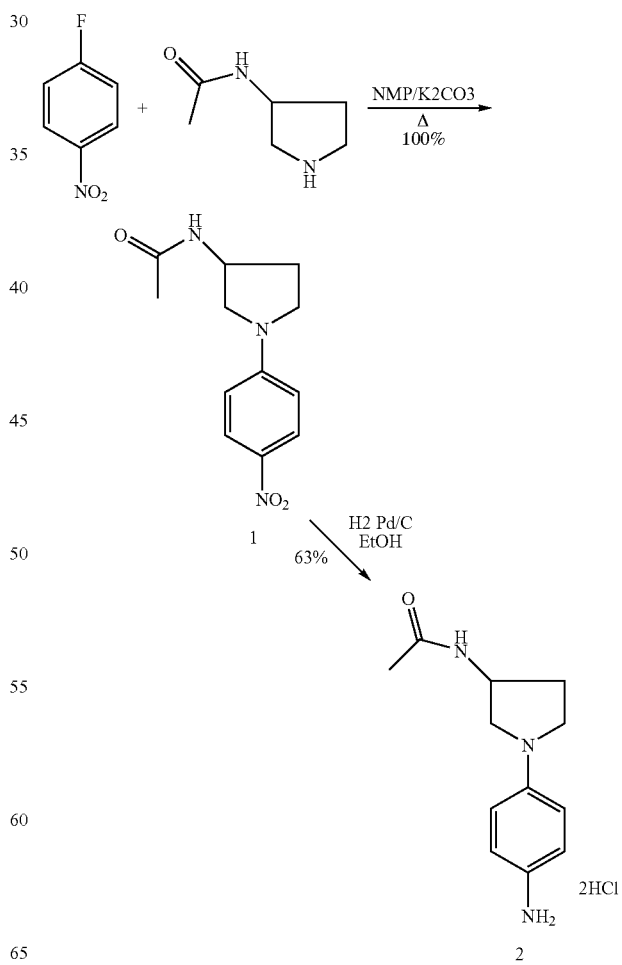

Synthesis of N-[1-(4-nitrophenyl)pyrrolidin-3-yl]-acetamide (1)

After dissolving 56.4 g of 1-fluoro-4-nitrobenzene (0.4 mol) and 51.2 g of 3-acetamidopyrrolidine (0.4 mol) in 400 ml of NMP, 66.4 g of potassium carbonate (0.48 mol) are added under a nitrogen atmosphere and the mixture is heated at 100° C. for 18 hours. The reaction medium is allowed to cool and is then poured into 2 l of water. The yellow precipitate formed is filtered off, washed with water and then dried in a vacuum oven over $P_2O_5$. 100 g (100%) of N-[1-(4-nitrophenyl)pyrrolidin-3-yl]acetamide (1) are thus obtained in the form of a yellow solid.

Synthesis of N-[1-(4-aminophenyl)pyrrolidin-3-yl]-acetamide monohydrochloride (2)

30 g of N-[1-(4-nitrophenyl)pyrrolidin-3-yl]-acetamide (1) (120 mmol) are partially dissolved in 670 ml of absolute ethanol in a stainless-steel hydrogenation reactor. 4.5 g of 5% Pd/C (50% water) are added and the reactor is closed and purged with nitrogen 3 times with stirring (1 600 rpm). Hydrogen is then introduced to a pressure of 10 bar at ambient temperature. The reaction medium is heated to 55° C. and is then cooled to 27° C. over 3 hours. The reactor is then purged with nitrogen and the reaction medium is filtered under a nitrogen atmosphere, and the filtrate is immediately recovered in 90 ml of hydrochloric ethanol solution (5N). The filtrate is then concentrated until a precipitate is obtained. The solid is filtered off, washed with isopropanol and then with ethyl ether and dried under vacuum in the presence of potassium hydroxide. 19.4 g (63%) of N-[1-(4-amino-phenyl)pyrrolidin-3-yl]acetamide dihydrochloride (2) are thus obtained in the form of a white solid. The 1H-NMR spectrum and mass spectrum are in accordance with the spectra for product (2).

| Elemental analysis (MW = 292.208; C12H17N3O · 2HCl) | | | | | |
| --- | --- | --- | --- | --- | --- |
| | % C | % H | % N | % O | % Cl |
| Theory | 49.33 | 6.55 | 14.38 | 5.48 | 24.27 |
| Found | 48.35 | 6.62 | 14.19 | 7.17 | 20.52 |

Example 5

[1-(4-Aminophenyl)pyrrolidin-3-yl]dimethylamine dihydrochloride (2)

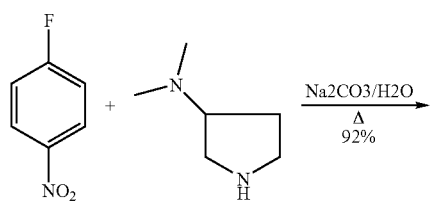

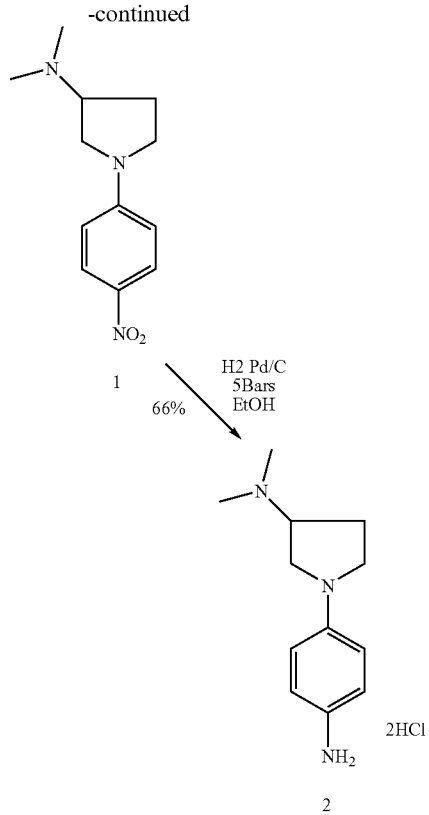

Synthesis of dimethyl-[1-(4-nitrophenyl)pyrrolidin-3-yl]amine (1)

32.38 g of potassium carbonate (308 mmol) are added to a solution of 250 ml of water containing 29.3 g of N,N-dimethylaminopyrrolidine (257 mmol) and 36.23 g of 4-fluoronitrobenzene (257 mmol), and the mixture is then refluxed for 3 hours. The reaction medium dissolves and a product then precipitates. The product is filtered off and washed with water. It is dried in a vacuum oven at 40° C. over $P_2O_5$. 55.9 g (92%) of dimethyl-[1-(4-nitrophenyl)pyrrolidin-3-yl]amine (1) are thus obtained in the form of a yellow solid.

Synthesis of [1-(4-aminophenyl)pyrrolidin-3-yl]dimethylamine dihydrochloride (2)

50 g of dimethyl-[1-(4-nitrophenyl)-pyrrolidin-3-yl]amine (1) (212 mmol) are added to 500 ml of absolute ethanol in a stainless-steel hydrogenation reactor. 10 g of 5% Pd/C (50% water) are added and the reactor is closed and purged with nitrogen 3 times with stirring (1 600 rpm). Hydrogen is then introduced at a pressure of 5–6 bar at ambient temperature. The temperature rises to 35° C. and then falls back to 27° C. over 1 hour. The reactor is then purged with nitrogen and the reaction medium is filtered under a nitrogen atmosphere, and the filtrate is recovered immediately in a solution containing 62 ml of 37% hydrochloric acid and 240 ml of isopropanol. The filtrate is then concentrated until a precipitate is obtained. The solid is filtered off, washed with isopropanol and then with ethyl ether and dried under vacuum at 50° C. in the presence of potassium hydroxide. 39.1 g (66%) of [1-(4-aminophenyl)pyrrolidin-3-yl]dimethylamine dihydrochloride (2) are thus obtained in the form of a white solid. The 1 H-NMR spectrum is in accordance with the spectrum for the product.

| Elemental analysis (MW = 278.225; C12H19N3 · 2HCl) | | | | |
|---|---|---|---|---|
| | % C | % H | % N | % Cl |
| Theory | 51.8 | 7.61 | 15.1 | 25.49 |
| Found | 51.2 | 7.73 | 14.83 | 25.46 |

Example 6

1-(4-Aminophenyl)pyrrolidin-3-ylamine dihydrochloride (3)

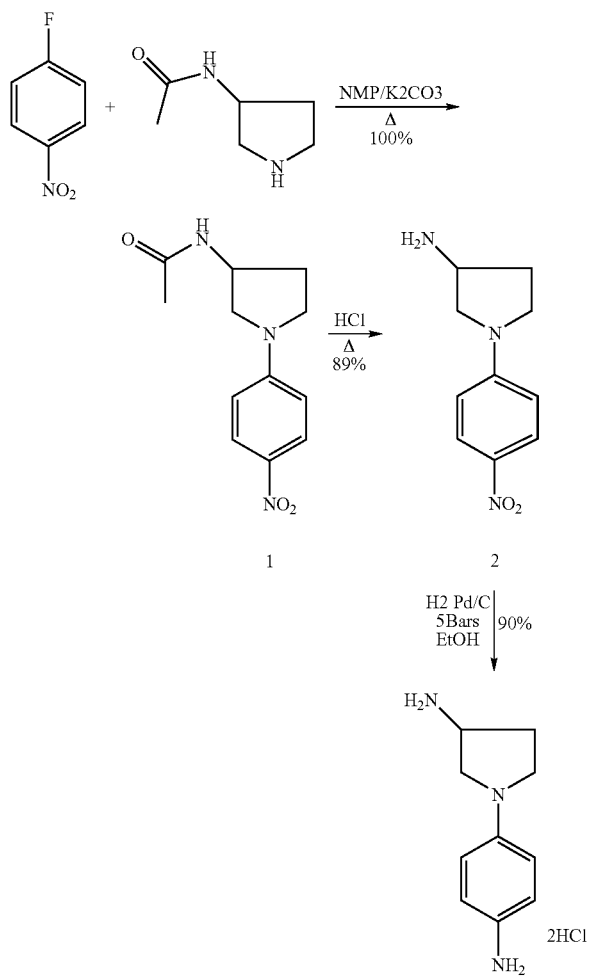

Synthesis of N-[1-(4-nitrophenyl)pyrrolidin-3-yl]acetamide (1)

After dissolving 56.4 g of 1-fluoro-4-nitrobenzene (0.4 mol) and 51.2 g of 3-acetamido-pyrrolidine (0.4 mol) in 400 ml of NMP, 66.4 g of potassium carbonate (0.48 mol) are added under a nitrogen atmosphere and the mixture is heated at 100° C. for 18 hours. The reaction medium is allowed to cool and is then poured into 2 l of water. The yellow precipitate formed is filtered off, washed with water and then dried in a vacuum oven over $P_2O_5$. 100 g (100%) of N-[1-(4-nitrophenyl)pyrrolidin-3-yl]acetamide (1) are thus obtained in the form of a yellow solid.

Synthesis of 1-(4-nitrophenyl)pyrrolidin-3-ylamine (2)

100 g (0.4 mol) of N-[1-(4-nitrophenyl)-pyrrolidin-3-yl]acetamide (1) are introduced as a suspension into a solution containing 300 ml of 37% hydrochloric acid and 660 ml of water in a 2 l three-necked flask. The reaction medium is heated at 90° C. for 7 hours 45 minutes. After cooling, the medium is neutralized carefully with 300 ml of aqueous 35% sodium hydroxide (pH=approximately 8). The resulting solid is then filtered off, after which it is washed with water (until the washing waters are neutral). The product is then dried under vacuum over $P_2O_5$. 74 g (89%) of 1-(4-nitrophenyl)pyrrolidin-3-ylamine (2) are thus obtained in the form of a yellow solid.

Synthesis of 1-(4-aminophenyl)pyrrolidin-3-ylamine dihydrochloride (3)

72 g of 1-(4-nitrophenyl)pyrrolidin-3-ylamine (2) (347 mmol) are added to 600 ml of methanol in a stainless-steel hydrogenation reactor. 15 g of 5% Pd/C (50% water) are added and the reactor is closed and purged with nitrogen 3 times with stirring (1 600 rpm). Hydrogen is then introduced at a pressure of 5 bar at ambient temperature. The temperature rises to 52° C. and then falls back to 38° C. over 2 hours 50 minutes. The reactor is then purged with nitrogen and the reaction medium is filtered under a nitrogen atmosphere, and the filtrate is immediately recovered in a solution containing 130 ml of 37% hydrochloric acid, 200 ml of isopropanol and 200 ml of absolute ethanol. The filtrate is then concentrated until a precipitate is obtained. The solid is filtered off, washed with isopropanol and then with ethyl ether and dried under vacuum at 50° C. in the presence of potassium hydroxide. 71 g (82%) of 1-(4-aminophenyl)pyrrolidin-3-ylamine dihydrochloride (3) are thus obtained in the form of a white solid. The 1 H-NMR spectrum and mass spectrum are in accordance with product (3).

| Elemental analysis (MW = 250.171; C10H15N3 · 2HCl) | | | | |
|---|---|---|---|---|
| | % C | % H | % N | % Cl |
| Theory | 48.01 | 6.85 | 16.8 | 28.34 |
| Found | 46.33 | 6.78 | 16.5 | 28.97 |

Example 7

Synthesis of 1-(4-aminophenyl)pyrrolidin-3-ol hydrochloride

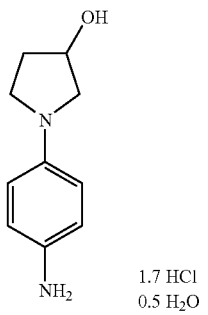

1.7 HCl
0.5 H₂O

Step 1: Preparation of 1-(4-nitrophenyl)pyrrolidin-3-ol 2 g of 1-fluoro-4-nitrobenzene (0.0155 mol), 1.3 g of sodium hydrogen carbonate (0.0155 mol) and 15 ml of a dioxane/water mixture (8/2) were introduced into a three-necked flask. 1.35 g of racemic 3-pyrrolidinol (0.0155 mol) were rapidly added to this mixture. The heterogeneous mixture was refluxed (87° C.) for 10 hours. The reaction mixture was then poured into ice-cold water; a yellow precipitate was obtained, which was filtered off and rinsed with water. After drying under vacuum in the presence of $P_2O_5$, 2.95 g of a yellow solid were obtained (97% yield).

$^1$H NMR analysis (DMSO-$d_6$, 200 MHz, ppm), in accordance with the expected product, was as follows:

8.04 (d, J=9 Hz, 2H); 6.58 (d, J=9 Hz, 2H); 5.06 (d, J=3.6 Hz, 1H); 4.41 (m, 1H); 3.45 (m, 3H); 3.20 (m, 1H); 2.04 (m, 2H).

The elemental analysis was as follows:

| % | C | H | N | O |
|---|---|---|---|---|
| Calculated | 57.89 | 5.81 | 13.45 | 23.05 |
| Found | 57.17 | 5.72 | 13.23 | 23.28 |

Step 2: Preparation of 1-(4-aminophenyl)pyrrolidin-3-ol hydrochloride

The 1-(4-nitrophenyl)pyrrolidin-3-ol obtained above in the preceding step (2 g, 9.605 mmol) was suspended in 40 ml of absolute ethanol and 8 ml of cyclohexene, and in the presence of 1 g of wet palladium-on-charcoal. Argon was then bubbled into the reaction medium for a few minutes, followed by refluxing for 4 hours. The reaction mixture was filtered into a vacuum flask containing 100 ml of diisopropyl ether, 50 ml of isopropanol and 4 equivalents of hydrochloric ethanol (6.2 ml) cooled to −5° C. The precipitate obtained was filtered quickly and dried in a vacuum oven at 30° C. 1.22 g of a slightly pink solid were obtained in a yield of 59%, the melting point of which is greater than 200° C.

The $^1$H NMR analysis (MeOH-$d_4$, 200 MHz, ppm) in accordance with the expected product, was as follows:

7.26 (d, J=9 Hz, 2H); 7.08 (d, J=9 Hz, 2H); 4.48 (m, 1H); 3.54 (m, 3H); 3.30 (m, 1H); 2.09 (m, 2H).

The elemental analysis was as follows:

| % | C | H | N | O | Cl |
|---|---|---|---|---|---|
| Calculated | 48.18 | 6.70 | 11.24 | 9.64 | 24.23 |
| Found | 48.54 | 6.62 | 11.16 | 9 | 24.67 |

The product obtained contains 1.7 molecules of HCl and 0.5 molecule of water.

Example 8

Synthesis of 1-(4-amino-2-methylphenyl)-pyrrolidin-3-ol hydrochloride

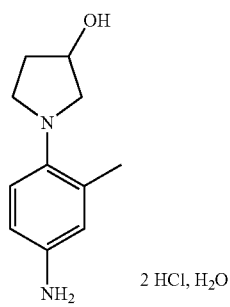

2 HCl, H₂O

Step 1: Preparation of 1-(4-nitro-2-methylphenyl)-pyrrolidin-3-ol 2.4 g of 1-fluoro-2-methyl-4-nitrobenzene (0.0155 mol), 1.3 g of sodium hydrogen carbonate (0.0155 mol) and 15 ml of a dioxane/water mixture (8/2) were introduced into a three-necked flask. 1.35 g of racemic 3-pyrrolidinol (0.0155 mol) were rapidly added to this mixture. The heterogeneous mixture was refluxed (87° C.) for 24 hours. The reaction mixture was then poured into ice-cold water; an orange precipitate was obtained, which was filtered off and rinsed with water. After drying under vacuum in the presence of $P_2O_5$, 3.19 g of an orange solid were obtained (93% yield).

The $^1$H NMR analysis (DMSO-$d_6$, 200 MHz, ppm), in accordance with the expected product, was as follows:

7.80 (m, 2H); 6.58 (m, 1H); 4.91 (d, J=3.3 Hz, 1H); 4.25 (m, 1H); 3.60 (m, 2H); 3.41 (m, 1H); 3.18 ppm (m, 1H); 2.34 (s, 3H); 1.82 (m, 2H)

The elemental analysis was as follows:

| % | C | H | N | O |
|---|---|---|---|---|
| Calculated | 59.45 | 6.35 | 12.60 | 21.60 |
| Found | 58.91 | 6.40 | 12.20 | 21.42 |

Step 2: Preparation of 1-(4-amino-2-methylphenyl)-pyrrolidin-3-ol hydrochloride The 1-(4-nitro-2-methylphenyl)pyrrolidin-3-ol obtained above in the preceding step (2 g, 9.00 mmol) was suspended in 40 ml of absolute ethanol and 8 ml of cyclohexene, and in the presence of 1 g of wet palladium-on-charcoal. Argon was then bubbled through the reaction medium for a few minutes, followed by refluxing for 4 hours. The reaction mixture was filtered into a vacuum flask containing 100 ml of diisopropyl ether, 50 ml of isopropanol and 4 equivalents of hydrochloric ethanol (6.2 ml) cooled to −5° C. The precipitate obtained was filtered quickly and dried in a vacuum oven at 30° C. 1.20 g of a slightly pink solid were obtained in a yield of 58%.

The $^1$H NMR analysis (MeOH-$d_4$, 200 MHz, ppm), in accordance with the expected product, was as follows:
7.79 (d, J=9 Hz, 1H); 7.28 (m, 2H); 4.58 (m, 1H): 3.94 (m, 2H); 3.53 (m, 1H); 3.13 (m, 1H); 2.48 (s, 3H); 2.20 (m, 2H).

The elemental analysis was as follows:

| % | C | H | N | O | Cl |
|---|---|---|---|---|---|
| Calculated | 46.80 | 7.09 | 9.93 | 11.34 | 24.82 |
| Found | 46.58 | 7.31 | 9.39 | 11.26 | 23.34 |

The product obtained contains 2 molecules of HCl and 1 molecule of water.

Example 9

Synthesis of 1-(4-amino-3-methylphenyl)-pyrrolidin-3-ol hydrochloride

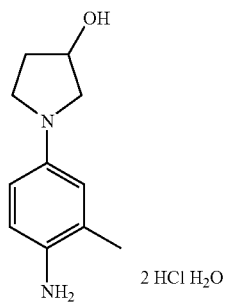

2 HCl H$_2$O

Step 1: Preparation of 1-(4-nitro-3-methylphenyl)-pyrrolidin-3-ol 1.90 ml of 1-fluoro-3-methyl-4-nitrobenzene (0.0155 mol), 1.3 g of sodium hydrogen carbonate (0.0155 mol) and 15 ml of a dioxane/water mixture (8/2) were introduced into a three-necked flask. 1.35 g of racemic 3-pyrrolidinol (0.0155 mol) were rapidly added to this mixture. The heterogeneous mixture was refluxed (87° C.) for 24 hours. The reaction mixture was then poured into ice-cold water; a yellow precipitate was obtained, which was filtered off and rinsed with water. After drying under vacuum in the presence of P$_2$O$_5$, 2.7 g of a yellow solid were obtained (78% yield).

The $^1$H NMR analysis (DMSO-$d_6$, 200 MHz, ppm), in accordance with the expected product, was as follows:
8.03 (d, J=9 Hz, 1H); 6.52 (m, 2H); 5.08 (d, J=3.2, 1H); 4.44 (m, 1H); 3.50 (m, 3H); 3.25 (m, 1H); 2.58 (s, 3H); 2.05 (m, 2H).

The elemental analysis was as follows:

| % | C | H | N | O |
|---|---|---|---|---|
| Calculated | 59.45 | 6.35 | 12.60 | 21.60 |
| Found | 58.82 | 6.48 | 12.16 | 21.50 |

Step 2: Preparation of 1-(4-amino-3-methylphenyl)-pyrrolidin-3-ol hydrochloride The 1-(4-nitro-3-methylphenyl)pyrrolidin-3-ol obtained above in the preceding step (2 g, 9.00 mmol) was suspended in 40 ml of absolute ethanol and 8 ml of cyclohexene, and in the presence of 1 g of wet palladium-on-charcoal. Argon was then bubbled through the reaction medium for a few minutes, followed by refluxing for 4 hours. The reaction mixture was filtered into a vacuum flask containing 100 ml of diisopropyl ether, 50 ml of isopropanol and 4 equivalents of hydrochloric ethanol (6.2 ml) cooled to −5° C. The precipitate obtained was filtered off rapidly and dried in a vacuum oven at 30° C. 1.93 g of a slightly pink solid were obtained in a yield of 94%.

The $^1$H NMR analysis (MeOH-$d_4$, 200 MHz, ppm), in accordance with the expected product, was as follows:
7.44 (m, 1H); 7.33 (m, 2H); 4.66 (m, 1H): 3.79 (m, 3H); 3.52 (m, 1H); 2.45 (s, 3H); 2.37 (m, 2H).

The elemental analysis was as follows:

| % | C | H | N | O | Cl |
|---|---|---|---|---|---|
| Calculated | 46.80 | 7.09 | 9.93 | 11.36 | 24.82 |
| Found | 47.49 | 6.95 | 9.66 | 11.32 | 24.56 |

The product obtained contains 2 molecules of HCl and 1 molecule of water.

DYEING EXAMPLES

The dye compositions below in accordance with the invention, were prepared:

| Examples | 1 | 2 | 3 |
|---|---|---|---|
| (4-Amino-3-methylphenyl)-pyrrolidin-3-ylamine, dihydrochloride | 3 × 10$^{-3}$ | 3 × 10$^{-3}$ | 3 × 10$^{-3}$ |
| Resorcinol | 3 × 10$^{-3}$ | | |
| 1-β-Hydroxyethyloxy-2,4-diaminobenzene | | 3 × 10$^{-3}$ | |
| 1-Methyl-4-aminophenol | | | 3 × 10$^{-3}$ |
| Common dye support | (*) | (*) | (*) |
| Demineralized water qs | 100 g | 100 g | 100 g |

| Examples | 4 | 5 | 6 | 7 |
|---|---|---|---|---|
| 1-(4-Amino-3-methoxyphenyl)-pyrrolidin-3-ol, dihydrochloride | 3 × 10$^{-3}$ | 3 × 10$^{-3}$ | 3 × 10$^{-3}$ | 3 × 10$^{-3}$ |

-continued

| | | | | |
|---|---|---|---|---|
| Resorcinol | $3 \times 10^{-3}$ | — | — | — |
| 1-β-Hydroxyethyloxy-2,4-diaminobenzene | — | $3 \times 10^{-3}$ | — | — |
| 1-Methyl-4-aminophenol | — | — | $3 \times 10^{-3}$ | — |
| Common dye support | (*) | (*) | (*) | (*) |
| Demineralized water qs | 100 g | 100 g | 100 g | 100 g |

| Examples | 8 | 9 | 10 |
|---|---|---|---|
| (R)-1-(4-Aminophenyl)pyrrolidin-3-ol, dihydrochloride | $3 \times 10^{-3}$ | $3 \times 10^{-3}$ | $3 \times 10^{-3}$ |
| Resorcinol | $3 \times 10^{-3}$ | | |
| 1-β-Hydroxyethyloxy-2,4-diaminobenzene | | $3 \times 10^{-3}$ | |
| 1-Methyl-4-aminophenol | | | $3 \times 10^{-3}$ |
| Common dye support | (*) | (*) | (*) |
| Demineralized water qs | 100 g | 100 g | 100 g |

| Examples | 11 | 12 |
|---|---|---|
| N-[1-(4-Aminophenyl)pyrrolidin-3-yl] acetamide dihydrochloride | $3 \times 10^{-3}$ | $3 \times 10^{-3}$ |
| Resorcinol | $3 \times 10^{-3}$ | |
| 1-β-Hydroxyethyloxy-2,4-diaminobenzene | | $3 \times 10^{-3}$ |
| Common dye support | (*) | (*) |
| Demineralized water qs | 100 g | 100 g |

| Examples | 13 | 14 | 15 | 16 |
|---|---|---|---|---|
| [1-(4-Aminophenyl)pyrrolidin-3-yl] dimethylamine dihydrochloride | $3 \times 10^{-3}$ | $3 \times 10^{-3}$ | $3 \times 10^{-3}$ | $3 \times 10^{-3}$ |
| Resorcinol | $3 \times 10^{-3}$ | — | — | — |
| 1-β-Hydroxyethyloxy-2,4-diaminobenzene | — | $3 \times 10^{-3}$ | — | — |
| 1-Methyl-4-aminophenol | — | — | $3 \times 10^{-3}$ | — |
| Common dye support | (*) | (*) | (*) | (*) |
| Demineralized water qs | 100 g | 100 g | 100 g | 100 g |

| Examples | 17 | 18 | 19 | 20 |
|---|---|---|---|---|
| 1-(4-Aminophenyl)pyrrolidin-3-ylamine dihydrochloride | $3 \times 10^{-3}$ | $3 \times 10^{-3}$ | $3 \times 10^{-3}$ | $3 \times 10^{-3}$ |
| Resorcinol | $3 \times 10^{-3}$ | — | — | — |
| 1-β-Hydroxyethyloxy-2,4-diaminobenzene | — | $3 \times 10^{-3}$ | — | — |
| 1-Methyl-4-aminophenol | — | — | $3 \times 10^{-3}$ | — |
| Common dye support | (*) | (*) | (*) | (*) |
| Demineralized water qs | 100 g | 100 g | 100 g | 100 g |

| Examples | 21 | 22 | 23 | 24 |
|---|---|---|---|---|
| 1-(4-Aminophenyl)pyrrolidin-3-ol, dihydochloride | $3 \times 10^{-3}$ | $3 \times 10^{-3}$ | $3 \times 10^{-3}$ | $3 \times 10^{-3}$ |
| Resorcinol | $3 \times 10^{-3}$ | — | — | — |
| 1-β-Hydroxyethyloxy-2,4-diaminobenzene | — | $3 \times 10^{-3}$ | — | — |
| 1-Methyl-4-aminophenol | — | — | $3 \times 10^{-3}$ | — |
| Common dye support | (*) | (*) | (*) | (*) |
| Demineralized water qs | 100 g | 100 g | 100 g | 100 g |

(*) Common dye support:

| | |
|---|---|
| Oleyl alcohol polyglycerolated with 2 mol of glycerol | 4.0 g |
| Oleyl alcohol polyglycerolated with 4 mol of glycerol, containing 78% active material (A.M.) | 5.69 g A.M. |
| Oleic acid | 3.0 g |
| Oleylamine containing 2 mol of ethylene oxide, sold under the trade name Ethomeen O12 ® by the company Akzo | 7.0 g |
| Diethylaminopropyl laurylaminosuccinamate, sodium salt containing 55% A.M. | 3.0 g A.M. |
| Oleyl alcohol | 5.0 g |
| Oleic acid diethanolamide | 12.0 g |
| Propylene glycol | 3.5 g |
| Ethyl alcohol | 7.0 g |
| Dipropylene glycol | 0.5 g |
| Propylene glycol monomethyl ether | 9.0 g |
| Sodium metabisulphite as an aqueous solution containing 35% A.M. | 0.455 g A.M. |
| Ammonium acetate | 0.8 g |
| Antioxidant, sequestering agent | qs |
| Fragrance, preserving agent | qs |
| Aqueous ammonia containing 20% $NH_3$ | 10.2 g |

At the time of use, each dye composition was mixed with an equal amount of an oxidizing composition consisting of a 20-volumes aqueous hydrogen peroxide solution (6% by weight) with a pH of about 3.

Each mixture obtained has a pH of about 9.5. Each mixture is applied to locks of natural gray hair containing 90% white hairs. After leaving the mixture to stand on the locks for 30 minutes, the locks of hair are rinsed, washed with a standard shampoo, rinsed and then dried.

The colour of the locks was evaluated in the L*a*b* system using a Minolta CM 2002® spectro-photometer (Illuminant D65).

In the L*a*b* system, the three parameters denote, respectively, the intensity (L*), the red-green chromatic component (a*) and the yellow-blue chromatic component (b*). According to this system, the higher the value of L, the paler or less intense the color. Conversely, the smaller the value of L, the darker or more intense the color.

| | Natural white hairs | | |
|---|---|---|---|
| Examples | L* | a* | b* |
| Ex. 1 | 35.2 | 3.8 | 6.1 |
| Ex. 2 | 23.8 | −1.9 | −8.3 |
| Ex. 3 | 25.4 | 4.8 | −10.45 |
| Ex. 4 | 33.5 | 0.4 | −4.9 |
| Ex. 5 | 26.2 | −3.3 | −11.5 |
| Ex. 6 | 29.5 | −0.5 | −13.3 |
| Ex. 7 | 48.2 | 2.6 | 6.8 |
| Ex. 8 | 28.2 | 4.0 | 0.3 |
| Ex. 9 | 22.2 | 2.1 | −13.3 |
| Ex. 10 | 20.1 | 3.5 | −8.0 |
| Ex. 11 | 31.3 | 3.9 | 1.2 |
| Ex. 12 | 23.2 | 0.06 | −13.05 |
| Ex. 13 | 37.35 | 5.4 | 5.6 |
| Ex. 14 | 26.0 | 0.01 | −11.8 |
| Ex. 15 | 34.6 | 8.0 | −6.3 |
| Ex. 16 | 49.2 | 2,5 | 8.75 |
| Ex. 17 | 29.9 | 5.45 | 3.4 |
| Ex. 18 | 22.1 | 2.22 | −12.8 |
| Ex. 19 | 24.1 | 8.1 | −9.7 |
| Ex. 20 | 40.9 | 3.3 | 6.7 |
| Ex. 21 | 29.9 | 4.44 | 0.58 |
| Ex. 22 | 23.6 | 0.7 | −13.8 |
| Ex. 23 | 22.9 | 5.8 | −14.2 |
| Ex. 24 | 47.6 | 1.0 | 8.45 |

The dye compositions below, in accordance with the invention, were prepared:

| Examples | 25 | 26 | 27 | 28 | 29 | 30 |
|---|---|---|---|---|---|---|
| N-(4-Aminophenyl)-3-hydroxylpyrrolidine, dihydrochloride (compound of formula (I)) | $3 \cdot 10^{-3}$ mol | $3 \cdot 10^{-3}$ mol | — | — | — | — |
| N-(4-Amino-2-methylphenyl)-3-hydroxylpyrrolidine, dihydrochloride (compound of formula (I)) | — | — | $3 \cdot 10^{-3}$ mol | $3 \cdot 10^{-3}$ mol | — | — |
| N-(4-Amino-3-methylphenyl)-3-hydroxylpyrrolidine, dihydrochloride (compound of formula (I)) | — | — | — | — | $3 \cdot 10^{-3}$ mol | $3 \cdot 10^{-3}$ mol |
| 2,4-Diamino-1-(β-hydroxyethyloxy)benzene, dihydrochloride (coupler) | $3 \cdot 10^{-3}$ mol | — | $3 \cdot 10^{-3}$ mol | — | $3 \cdot 10^{-3}$ mol | — |
| 1,3-Dihydroxybenzene (coupler) | — | $3 \cdot 10^{-3}$ mol | — | $3 \cdot 10^{-3}$ mol | — | $3 \cdot 10^{-3}$ mol |
| Common dye support | (*) | (*) | (*) | (*) | (*) | (*) |
| Demineralized water qs | 100 g | 100 g | 100 g | 100 g | 100 g | 100 g |

(*) Common dye support: identical to that described above

At the time of use, each dye composition is mixed with an equal amount of an oxidizing composition consisting of a 20 volumes aqueous hydrogen peroxide solution (6% by weight) with a pH of about 3.

Each mixture obtained has a pH of about 9.5, and is applied to locks of natural gray hair containing 90% white hairs. After 30 minutes, the locks of hair are then rinsed, washed with a standard shampoo and then dried.

The locks of hair were dyed in the shades given in the table below:

| EXAMPLE | SHADE ON NATURAL HAIR |
|---|---|
| 25 | Blue |
| 26 | Ash violet iridescent blonde |
| 27 | Ash light blue |
| 28 | Very slightly golden ash beige |
| 29 | Slightly matt blue |
| 30 | Slightly golden ash grey |

The invention claimed is:

1. A composition for oxidation dyeing of keratinous fibers, comprising, in a medium suitable for dyeing, at least one oxidation base chosen from para-phenylenediamine derivatives containing a pyrrolidinyl group of formula (I) and their acid addition salts:

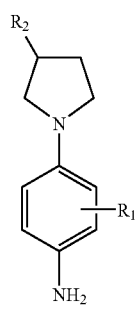

(I)

wherein:

$R_1$ is chosen from a hydrogen atom; a chlorine atom; a bromine atom; and linear and branched, saturated and unsaturated ($C_1$–$C_7$) alkyl groups, optionally substituted with at least one halogen atom, wherein at least one carbon atom is optionally replaced by an oxygen atom, a nitrogen atom, a sulfur atom or an $SO_2$ group, and, when present, at least one branch of said branched groups may form at least one 3- to 6-membered ring containing at least one carbon atom, with the proviso that said $R_1$ does not comprise a group chosen from a peroxide bond, a diazo group, a nitro group, and a nitroso group; and $R_2$ is chosen from a hydroxyl group; an amino group; a group —$OR_3$, wherein $R_3$ is chosen from linear and branched ($C_1$–$C_4$) alkyl groups substituted with at least one group chosen from halogen atoms, ($C_1$–$C_2$) alkoxy groups, amino groups substituted with at least one hydroxyl group, ($C_1$–$C_2$) aminoalkyl groups substituted with at least one hydroxyl group, and ($C_3$–$C_4$) alkyl groups substituted with at least one hydroxyl group; a methylcarbonyl group; an acetamido group; and a group —$NR_4R_5$, wherein $R_4$ and $R_5$, which are identical or different, are each independently chosen from a hydrogen atom, linear and branched ($C_1$–$C_4$) alkyl groups substituted with at least one group chosen from a halogen atom, a hydroxyl group, ($C_1$–$C_2$) alkoxy groups, an amino group and ($C_1$–$C_2$) aminoalkyl groups, wherein said at least one oxidation base of formula (I) is chosen from:

N-(4-aminophenyl)-3-hydroxypyrrolidine,
N-(4-amino-2-methylphenyl)-3-hydroxypyrrolidine,
N-(4-amino-2-ethylphenyl)-3-hydroxypyrrolidine,
N-(4-amino-2-methoxyphenyl)-3-hydroxypyrrolidine,
N-(4-amino-2-(2-hydroxyethyl)phenyl)-3-hydroxypyrrolidine,
N-(4-amino-2-(1-hydroxyethyl)phenyl)-3-hydroxypyrrolidine,
N-(4-amino-2-(1,2-dihydroxyethyl)phenyl)-3-hydroxypyrrolidine,
N-(4-amino-3-methylphenyl)-3-hydroxypyrrolidine,
N-(4-amino-3-ethylphenyl)-3-hydroxypyrrolidine,
N-(4-amino-3-methoxyphenyl)-3-hydroxypyrrolidine,
N-(4-amino-3-(2-hydroxyethyl)phenyl)-3-hydroxypyrrolidine, N-(4-amino-3-(1-hydroxyethyl)phenyl)-3-hydroxypyrrolidine,
N-(4-amino-3-(1,2-dihydroxyethyl)phenyl)-3-hydroxypyrrolidine,
N-(4-aminophenyl)-3-aminopyrrolidine,
N-(4-amino-2-methylphenyl)-3-aminopyrrolidine,
N-(4-amino-2-ethylphenyl)-3-aminopyrrolidine,
N-(4-amino-2-methoxyphenyl)-3-aminopyrrolidine,
N-(4-amino-2-(2-hydroxyethyl)phenyl)-3-aminopyrrolidine,
N-(4-amino-2-(1-hydroxyethyl)phenyl)-3-aminopyrrolidine,
N-(4-amino-2-(1,2-dihydroxyethyl)phenyl)-3-hydroxypyrrolidine,
N-(4-amino-3-methylphenyl)-3-aminopyrrolidine,
N-(4-amino-3-ethylphenyl)-3-aminopyrrolidine,
N-(4-amino-3-methoxyphenyl)-3-aminopyrrolidine,
N-(4-amino-3-(2-hydroxyethyl)phenyl)-3-aminopyrrolidine,
N-(4-amino-3-(1-hydroxyethyl)phenyl)-3-aminopyrrolidine,
N-(4-amino-3-(1,2-dihydroxyethyl)phenyl)-3-aminopyrrolidine,
N-[1-(4-Aminophenyl)pyrrolidin-3-yl]-acetamide,
[1-(4-Aminophenyl)pyrrolidin-3-yl]dimethyl-amine,
and their acid addition salts.

2. A composition according to claim 1, wherein $R_1$ is chosen from a hydrogen atom, saturated and unsaturated, linear and branched hydrocarbon-based chains, alkoxy groups, alkoxyalkyl groups, monohydroxyalkyl groups, polyhydroxyalkyl groups, aminoalkyl groups, carboxyalkyl groups, hydroxyaminoalkyl groups, and hydroxyalkoxy groups.

3. A composition according to claim 2, wherein $R_1$ is chosen from a hydrogen atom, a methyl group, an ethyl group, an isopropyl group, a vinyl group, an allyl group, a methoxymethyl group, a hydroxymethyl group, a 1-carboxymethyl group, a 1-aminomethyl group, a 2-carboxyethyl group, a 2-hydroxyethyl group, a 3-hydroxypropyl group, a 1,2-dihydroxyethyl group, a 1-hydroxy-2-aminoethyl group, a methoxy group, an ethoxy group, an allyloxy group, a 2-hydroxyethyloxy group and a 3-hydroxyethyloxy group.

4. A composition according to claim 3, wherein $R_1$ is chosen from a hydrogen atom, a methyl group, a hydroxymethyl group, a 2-hydroxyethyl group, a 1,2-dihydroxyethyl group, a methoxy group, and a 2-hydroxyethyloxy group.

5. A composition according to claim 1, wherein $R_2$ is chosen from a hydroxyl group; an amino group; a group —$OR_3$, wherein $R_3$ is chosen from linear and branched ($C_1$–$C_4$) alkyl groups substituted with at least one group chosen from halogen atoms, ($C_1$–$C_2$) alkoxy groups, an amino group; ($C_1$–$C_2$) aminoalkyl groups; a methylcarbonyl group; a group —$NR_4R_5$, wherein $R_4$ and $R_5$, which are identical or different, are each independently chosen from a hydrogen atom, linear and branched ($C_1$–$C_4$) alkyl groups substituted with at least one group chosen from halogen atoms, a hydroxyl group, ($C_1$–$C_2$) alkoxy groups, an amino group, and ($C_1$–$C_2$) aminoalkyl groups.

6. A composition according to claim 5, wherein $R_2$ is chosen from a hydroxyl group, an acetoxy group, an amino group, a methylamino group, a dimethylamino group and a 2-hydroxyethylamino group.

7. A composition according to claim 1, wherein said at least one oxidation base of formula (I) is present in an amount ranging from 0.0005% to 12% by weight relative to the total weight of the dye composition.

8. A composition according to claim 7, wherein said at least one oxidation base of formula (I) is present in an amount ranging from 0.005% to 6% by weight relative to the total weight of the dye composition.

9. A composition according to claim 1, wherein said medium suitable for dyeing comprises water and optionally at least one organic solvent.

10. A composition according to claim 9, wherein said at least one organic solvent is chosen from ($C_1$–$C_4$) alkanols, glycerol, glycols, glycol ethers, and aromatic alcohols.

11. A composition according to claim 10, wherein said ($C_1$–$C_4$) alkanols are chosen from ethanol and isopropanol.

12. A composition according to claim 10, wherein said glycols are chosen from 2-butoxyethanol and propylene glycol.

13. A composition according to claim 10, wherein said glycol ethers are chosen from propylene glycol monomethyl ether, diethylene glycol monoethyl ether, and monomethyl ether.

14. A composition according to claim 10, wherein said aromatic alcohols are chosen from benzyl alcohol and phenoxyethanol.

15. A composition according to claim 9, wherein said at least one organic solvent is present in an amount ranging from 1% to 40% by weight relative to the total weight of the dye composition.

16. A composition according to claim 15, wherein said at least one organic solvent is present in an amount ranging from 5% to 30% by weight relative to the total weight of the dye composition.

17. A composition according to claim 1, wherein said composition further comprising at least one coupler.

18. A composition according to claim 17, wherein said at least one coupler is chosen from substituted meta-phenylenediamines, substituted meta-aminophenols, substituted meta-diphenols, optionally substituted naphthols and acylated naphthols, optionally substituted heterocyclic couplers, and their acid addition salts.

19. A composition according to claim 18, wherein said optionally substituted heterocyclic couplers are chosen from pyrazolo[1,5-b]-1,2,4-triazole, pyrazolo[3,2,-c]-1,2,4-triazpole, pyrazol-5-one, pyridines, indoles, indolines, indazoles, benzimidazoles, benzothiazoles, bensoxazoles, 1,3-benzodioxoles and quinolines.

20. A composition according to claim 18, wherein said substituted meta-aminophenols are chosen from meta-aminophenols of formula (III) and their acid addition salts:

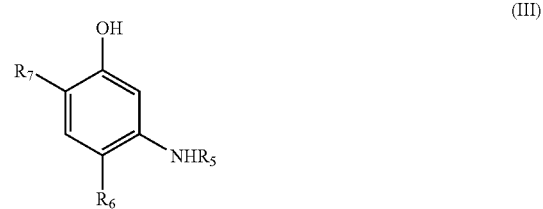

(III)

wherein:
$R_5$ is chosen from a hydrogen atom, ($C_1$–$C_4$) alkyl groups, ($C_1$–$C_4$) monohydroxyalkyl groups and ($C_2$–$C_4$) polyhydroxyalkyl groups;
$R_6$ is chosen from a hydrogen atom, ($C_1$–$C_4$) alkyl groups, ($C_1$–$C_4$) alkoxy groups and halogen atoms chosen from chlorine, bromine and fluorine; and $R_7$ is chosen from a hydrogen atom, $(C_1–C_4)$ alkyl groups, $(C_1–C_4)$ alkoxy groups, $(C_1–C_4)$ monohydroxyalkyl groups, $(C_2–C_4)$ polyhydroxyalkyl groups, $(C_1–C_4)$ monohydroxyalkoxy groups and $(C_2–C_4)$ polyhydroxyalkoxy groups.

21. A composition according to claim 18, wherein said substituted meta-diphenols are chosen from meta-diphenols of formula (VI) and their acid addition salts:

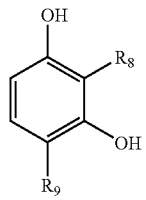

(VI)

wherein:

$R_8$ and $R_9$, which are identical or different, are each chosen from a hydrogen atom, $(C_1–C_4)$ alkyl groups and halogen atoms chosen from chlorine, bromine and fluorine, provided that at least one of $R_8$ and $R_9$ is other than a hydrogen atom.

22. A composition according to claim 18, wherein said substituted meta-phenylenediamines are chosen from meta-phenylenediamines of formula (V) and their acid addition salts:

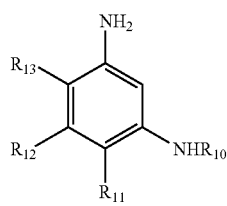

(V)

wherein:

$R_{10}$ is chosen from a hydrogen atom, $(C_1–C_4)$ alkyl groups, $(C_1–C_4)$ monohydroxyalkyl groups, and $(C_2–C_4)$ polyhydroxyalkyl groups;

$R_{11}$ and $R_{12}$, which are identical or different, are each chosen from a hydrogen atom, $(C_1–C_4)$ alkyl groups, $(C_1–C_4)$ monohydroxyalkoxy groups, and $(C_2–C_4)$ polyhydroxyalkoxy groups;

$R_{13}$ is chosen from a hydrogen atom, $(C_1–C_4)$ alkoxy groups, $(C_1–C_4)$ aminoalkoxy groups, $(C_1–C_4)$ monohydroxyalkoxy groups, $(C_2–C_4)$ polyhydroxalkoxy groups, and 2,4-diaminophenoxyalkoxy groups; provided that at least one substituent chosen from $R_{10}$, $R_{11}$, $R_{12}$, and $R_{13}$ is other than a hydrogen atom.

23. A composition according to claim 18, wherein said optionally substituted heterocyclic couplers are chosen from indole derivatives, indoline derivatives, benzimidazole derivatives, benzomorpholine derivatives, sesamol derivatives, pyrazoloazole derivatives, pyrroloazole derivatives, imidazoloazole derivatives, pyrazolopyrimidine derivatives, pyrazolin-3,5-dione derivatives, pyrrolo[3,2-d]oxazole derivatives, pyrazolo[3,4-d]thiazole derivatives, thiazoloazole S-oxide derivatives, thiazoloazole S,S-dioxide derivatives, and their acid addition salts.

24. A composition according to claim 23, wherein said indole derivatives are chosen from the compounds of formula (VI) and their acid addition salts:

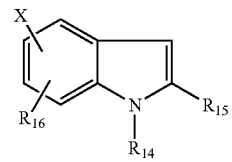

(VI)

wherein:

$R_{14}$ is chosen from a hydrogen atom, $(C_1–C_4)$ alkyl groups, $(C_1–C_4)$ monohydroxyalkyl groups, $(C_2–C_4)$ polyhydroxyalkyl groups, and $(C_1–C_4)$ aminoalkyl groups, wherein the nitrogen atom of the amino group is substituted with one or two $(C_1–C_4)$ alkyl groups;

$R_{15}$ is chosen from a hydrogen atom and $(C_1–C_4)$ alkyl groups;

$R_{16}$ is chosen from a hydrogen atom, $(C_1–C_4)$ alkyl groups, and a hydroxyl group; and X is chosen from a hydroxyl group and a group $NHR_{17}$, wherein $R_{17}$ is chosen from a hydrogen atom, $(C_1–C_4)$ alkyl groups, and $(C_1–C_4)$ hydroxyalkyl groups.

25. A composition according to claim 23, wherein said indoline derivatives are chosen from 4-hydroxyindoline, 6-hydroxyindoline, 6-aminoindoline, 5,6-dihydroxyindoline, and their acid addition salts.

26. A composition according to claim 23, wherein said benzimidazole derivatives are chosen from compounds of formula (VII) and their acid addition salts:

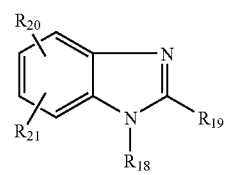

(VII)

wherein:

$R_{18}$ is chosen from a hydrogen atom and $(C_1–C_4)$ alkyl groups, $R_{19}$ is chosen from a hydrogen atom, $(C_1–C_4)$ alkyl groups, and a phenyl group, $R_{20}$ is chosen from a hydroxyl group, an amino group, and a methoxy group, $R_{21}$ is chosen from a hydrogen atom, a hydroxyl group, a methoxy group, and $(C_1–C_4)$ alkyl groups, with the proviso that:

when $R_{20}$ is an amino group, then $R_{20}$ occupies position 4, when $R_{20}$ occupies position 4, then $R_{21}$ occupies position 7, and when $R_{20}$ occupies position 5, then $R_{21}$ occupies position 6.

27. A composition according to claim 23, wherein said benzomorpholine derivatives are chosen from compounds of formula (VIII) and their acid addition salts:

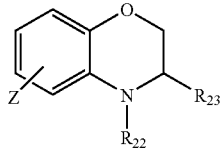

(VIII)

wherein:
$R_{22}$ and $R_{23}$, which are identical or different, are each chosen from a hydrogen atom and ($C_1$–$C_4$) alkyl groups, and
Z is chosen from a hydroxyl group and an amino group.

28. A composition according to claim 23, wherein said sesamol derivatives are chosen from compounds of formula (IX) and their acid addition salts:

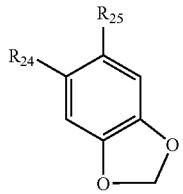

(IX)

wherein:
$R_{24}$ is chosen from a hydroxyl group, an amino group, ($C_1$–$C_4$) alkylamino groups, ($C_1$–$C_4$) monohydroxyalkylamino groups, and ($C_2$–$C_4$) polyhydroxyalkylamino groups, and
$R_{25}$ is chosen from a hydrogen atom, halogen atoms, and ($C_1$–$C_4$) alkoxy groups.

29. A composition according to claim 23, wherein said pyrazoloazole derivatives are chosen from:
2-methylpyrazolo[1,5-b]-1,2,4-triazole,
2-ethylpyrazolo[1,5-b]-1,2,4-triazole,
2-isopropylpyrazolo[1,5-b]-1,2,4-triazole,
2-phenylpyrazolo[1,5-b]-1,2,4-triazole,
2,6-dimethylpyrazolo[1,5-b]-1,2,4-triazole,
7-chloro-2,6-dimethylpyrazolo[1,5-b]-1,2,4-triazole,
3,6-dimethylpyrazolo[3,2-c]-1,2,4-triazole,
6-phenyl-3-methylthiopyrazolo[3,2-c]-1,2,4-triazole,
6-aminopyrazolo[1,5-a]benzimidazole,
5-cyano-4-ethoxycarbonyl-8-methylpyrrolo[1,2-b]-1,2,4-triazole,
5-cyano-8-methyl-4-phenylpyrrolo[1,2-b]-1,2,4-triazole,
7-amido-6-ethoxycarbonylpyrrolo[1,2-a]benzimidazole, and their acid addition salts.

30. A composition according to claim 29, wherein said pyrroloazole derivatives are chosen from:
5-cyano-4-ethoxycarbonyl-8-methylpyrrolo[1,2-b]-1,2,4-triazole,
5-cyano-8-methyl-4-phenylpyrrolo[1,2-b]-1,2,4-triazole,
7-amido-6-ethoxycarbonylpyrrolo[1,2-a]benzimidazole, and their acid addition salts.

31. A composition according to claim 23, wherein said imidazoloazole derivatives are chosen from:
7,8-dicyanoimidazolo[3,2-a]imidazole,
7,8-dicyano-4-methylimidazolo[3,2-a]imidazole, and their acid addition salts.

32. A composition according to claim 23, wherein said pyrazolopyrimidine derivatives are chosen from:
pyrazolo[1,5-a]pyrimidin-7-one,
2,5-dimethylpyrazolo[1,5-a]pyrimidin-7-one,
2-methyl-6-ethoxycarbonylpyrazolo[1,5-a]pyrimidin-7-one,
2-methyl-5-methoxymethylpyrazolo[1,5-a]pyrimidin-7-one,
2-tert-butyl-5-trifluoromethylpyrazolo[1,5-a]pyrimidin-7-one,
2,7-dimethylpyrazolo[1,5-a]pyrimidin-5-one, and their acid addition salts.

33. A composition according to claim 23, wherein said pyrazoline-3,5-dione derivatives are chosen from:
1,2-diphenylpyrazoline-3,5-dione,
1,2-diethylpyrazoline-3,5-dione, and their acid addition salts.

34. A composition according to claim 18, wherein said naphthols and acylated naphthols are chosen from compounds of formula (X) and their acid addition salts:

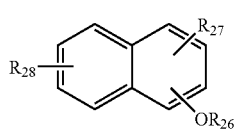

(X)

wherein:
$R_{26}$ is chosen from a hydrogen atom, and a group —CO—R, wherein R is chosen from ($C_1$–$C_4$) alkyl groups;
$R_{27}$ is chosen from a hydrogen atom, a hydroxyl group, ($C_1$–$C_4$) alkyl groups, and a —$SO_3H$ group; and
$R_{28}$ is chosen from a hydrogen atom and a hydroxyl group; provided that at least one of $R_{26}$, $R_{27}$, and $R_{28}$ is other than a hydrogen atom.

35. A composition according to claim 17, wherein said at least one coupler is chosen from 2-methyl-5-aminophenol, 5-N-(β-hydroxyethyl) amino-2-methylphenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy) benzene, 2-amino-4-(β-hydroxyethylamino)-1-methoxybenzene, 1,3-diaminobenzene, 1,3-bis(2,4-diaminophenoxy) propane, sesamol, α-naphthol, 2-methyl-1-naphthol, 6-hydroxyindole, 4-hydroxyindole, 4-hydroxy-N-methylindole, 6-hydroxyindoline, 2,6-dihydroxy-4-methylpyridine, 1H-3-methylpyrazol-5-one, 1-phenyl-3-methylpyrazol-5-one, 2-amino-3-hydroxypyridine, 3,6-dimethylpyrazolo[3,2-c]-1,2,4-triazole and 2,6-dimethylpyrazolo[1,5-b]-1,2,4-triazole, and their acid addition salts.

36. A composition according to claim 17, wherein said at least one coupler is present in an amount ranging from 0.0001% to 10% by weight relative to the total weight of said composition.

37. A composition according to claim 36, wherein said at least one coupler is present in an amount ranging from 0.005% to 5% by weight relative to the total weight of said composition.

38. A composition according to claim 1, further comprising at least one additional oxidation base provided that said at least one additional oxidation base is other than said at least one oxidation base of formula (I).

39. A composition according to claim 38, wherein said at least one additional oxidation base is chosen from para-phenylenediamines other than the para-phenylenediamine derivatives containing a pyrrolidinyl group of formula (I), bis(phenyl) alkylenediamines, para-aminophenols, ortho-aminophenols, heterocyclic bases, and their acid addition salts.

40. A composition according to claim 38, wherein said at least one additional base is chosen from heterocyclic oxidation bases, double bases, substituted para-aminophenols, ortho-aminophenols, para-phenylenediamine derivatives of formula (II), and their acid addition salts:

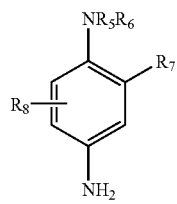

(II)

wherein:
- $R_5$ is chosen from a hydrogen atom, $(C_1-C_4)$ alkyl groups optionally substituted with at least one nitrogen containing group, $(C_1-C_4)$ monohydroxyalkyl groups, $(C_2-C_4)$ polyhydroxyalkyl groups, $(C_1-C_4)$ alkoxy $(C_1-C_4)$ alkyl groups, $(C_1-C_4)$ alkyl groups, a phenyl group, and a 4'-aminophenyl group;
- $R_6$ represents a hydrogen atom, $(C_1-C_4)$ alkyl groups optionally substituted with at least one nitrogen containing group, $(C_1-C_4)$ monohydroxyalkyl groups, $(C_2-C_4)$ polyhydroxyalkyl groups, and $(C_1-C_4)$ alkoxy $(C_1-C_4)$ alkyl groups;
- $R_7$ is chosen from a hydrogen atom, halogen atoms, $(C_1-C_4)$ alkyl groups, $(C_1-C_4)$ monohydroxyalkyl groups, $(C_1-C_4)$ hydroxyalkoxy groups, acetylamino $(C_1-C_4)$ alkoxy groups, $(C_1-C_4)$ mesylaminoalkoxy groups, and carbamoylamino$(C_1-C_4)$ alkoxy groups; and
- $R_8$ is chosen from a hydrogen atom, halogen atoms, and $(C_1-C_4)$ alkyl groups.

41. A composition according to claim 40, wherein said double bases are chosen from the compounds of formula (III) and their acid addition salts:

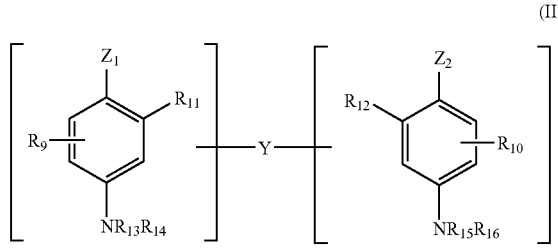

(III)

wherein:
- $Z_1$ and $Z_2$, which are identical or different, are each chosen from a hydroxyl group, —$NH_2$ groups optionally substituted with a group chosen from $(C_1-C_4)$ alkyl groups and linkers Y;
- linker Y is chosen from linear and branched $(C_1-C_{14})$ alkylene chains optionally substituted with at least one group chosen from hydroxyl groups and $(C_1-C_6)$ alkoxy groups, and wherein said linear and branched $(C_1-C_{14})$ alkylene chains are optionally interrupted or terminated with at least one group chosen from nitrogen containing groups and hetero atoms;
- $R_9$ and $R_{10}$, which are identical or different, are each chosen from a hydrogen atom, halogen atoms, $(C_1-C_4)$ alkyl groups, $(C_1-C_4)$ monohydroxyalkyl groups, $(C_2-C_4)$ polyhydroxyalkyl groups, $(C_1-C_4)$ aminoalkyl groups and linkers Y;
- $R_{11}$, $R_{12}$, $R_{13}$, $R_{14}$, $R_{15}$ and $R_{16}$, which are identical or different, are each chosen from a hydrogen atom, linkers Y, and $(C_1-C_4)$ alkyl groups; provided that said double bases of formula (III) contain only one linker Y per molecule.

42. A composition according to claim 40, wherein said double bases are chosen from the compounds of formula (IV) and their acid addition salts:

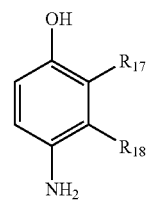

(IV)

wherein:
- $R_{17}$ is chosen from a hydrogen atom, halogen atoms, $(C_1-C_4)$ alkyl groups, $(C_1-C_4)$ monohydroxyalkyl groups, $(C_1-C_4)$ alkoxy$(C_1-C_4)$ alkyl groups, $(C_1-C_4)$ aminoalkyl groups, and hydroxy$(C_1-C_4)$ alkylamino $(C_1-C_4)$ alkyl groups;
- $R_{18}$ is chosen from a hydrogen atom, halogen atoms, $(C_1-C_4)$ alkyl groups, $(C_1-C_4)$ monohydroxyalkyl groups, $(C_2-C_4)$ polyhydroxyalkyl groups, $(C_1-C_4)$ aminoalkyl groups, $(C_1-C_4)$ cyanoalkyl groups, and $(C_1-C_4)$ alkoxy-$(C_1-C_4)$ alkyl groups;
- provided that at least one group chosen from $R_{17}$ and $R_{18}$ is other than a hydrogen atom.

43. A composition according to claim 40, wherein said ortho-aminophenols are chosen from 2-aminophenol, 2-amino-5-methylphenol, 2-amino-6-methylphenol, 5-acetamido-2-aminophenol, and their acid addition salts.

44. A composition according to claim 39, wherein said heterocyclic bases are chosen from pyridine derivatives, pyrimidine derivatives, pyrazole derivatives, and their acid addition salts.

45. A composition according to claim 44, wherein said pyridine derivatives are chosen from 2,5-diaminopyridine, 2-(4-methoxyphenyl) amino-3-aminopyridine, 2,3-diamino-6-methoxypyridine, 2-(β-methoxyethyl) amino-3-amino-6-methoxypyridine, 3,4-diaminopyridine, and their acid addition salts.

46. A composition according to claim 44, wherein said pyrimidine derivatives are chosen from 2,4,5,6-tetraaminopyrimidine, 4-hydroxy-2,5,6-triaminopyrimidine, 2-hydroxy-4,5,6-triaminopyrimidine, 6-hydroxy-2,4,5-triaminopyrimidine 2,4-dihydroxy-5,6-diaminopyrimidine, 2,5,6-triaminopyrimidine, pyrazolopyrimidine derivatives, their acid addition salts, and their corresponding tautomeric forms.

47. A composition according to claim 44, wherein said pyrazole derivatives are chosen from 4,5-diamino-1-methylpyrazole, 3,4-diaminopyrazole,
- 4,5-diamino-1-(4'-chlorobenzyl) pyrazole, 4,5-diamino-1, 3-dimethylpyrazole,
- 4,5-diamino-1-(β-hydroxyethyl) pyrazole, 4,5-diamino-3-methyl-1-phenylpyrazole,
- 4,5-diamino-1-methyl-3-phenylpyrazole, 4-amino-1,3-dimethyl-5-hydrazinopyrazole,
- 1-benzyl-4,5-diamino-3-methylpyrazole, 4,5-diamino-3-tert-butyl-1-methylpyrazole,
- 4,5-diamino-1-tert-butyl-3-methylpyrazole,
- 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole,
- 4,5-diamino-1-ethyl-3-hydroxymethylpyrazole,
- 4,5-diamino-3-hydroxymethyl-1-methylpyrazole,
- 4,5-diamino-3-hydroxymethyl-1-isopropylpyrazole,
- 4,5-diamino-3-methyl-1-isopropylpyrazole,
- 4-amino-5-(2'-aminoethyl) amino-1,3-dimethylpyrazole, 3,4,5-triaminopyrazole,
- 1-methyl-3,4,5-triaminopyrazole, 3,5-diamino-1-methyl-4-methylaminopyrazole,
- 3,5-diamino-4-(β-hydroxyethyl) amino-1-methylpyrazole, and their acid addition salts.

48. A composition according to claim 38, wherein said at least one additional oxidation base is present in an amount ranging from 0.0005% to 12% by weight relative to the total weight of said composition.

49. A composition according to claim 48, wherein said at least one additional oxidation base is present in an amount ranging from 0.005% to 6% by weight relative to the total weight of said composition.

50. A composition according to claim 1, wherein said acid addition salts are chosen from hydrochlorides, hydrobromides, sulfates, citrates, succinates, tartrates, lactates, phosphates and acetates.

51. A composition according to claim 1, further comprising at least one direct dye.

52. A composition according to claim 51, wherein said at least one direct dye is chosen from synthetic dyes and natural dyes.

53. A composition according to claim 52, wherein said synthetic dyes are chosen from azo dyes, quinone dyes, triarylmethane dyes, indoamine dyes, and azine dyes.

54. A composition according to claim 51, wherein said at least one direct dye is present in an amount ranging from 0.001% to 20% by weight relative to the total weight of the composition.

55. A composition according to claim 54, wherein said at least one direct dye is present in an amount ranging from 0.005% to 10% by weight relative to the total weight of the composition.

56. A composition according to claim 1, further comprising at least one polymer chosen from:
(i) amphoteric polymers;
(ii) cationic polymers comprising at least two repeating units; and
(iii) amphiphilic polymers comprising at least one fatty chain, wherein said amphiphilic polymers are chosen from polymers other than said amphoteric polymers (i) and said cationic polymers (ii);

wherein said at least two repeating units of said cationic polymers are independently chosen from compounds of formula (II):

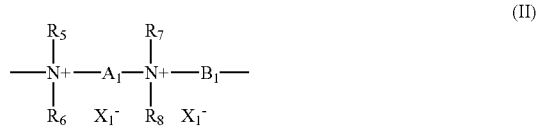

wherein:
$R_5$, $R_6$, $R_7$ and $R_8$, which are identical or different, are each chosen from ($C_1$–$C_{20}$) aliphatic groups, ($C_1$–$C_{20}$) alicyclic groups, ($C_1$–$C_{20}$) arylaliphatic groups, and lower hydroxyalkylaliphatic groups; or $R_5$, $R_6$, $R_7$ and $R_8$, together or separately, form, with the nitrogen atoms to which they are attached, at least one heterocycle optionally containing an additional hetero atom other than nitrogen; or $R_5$, $R_6$, $R_7$ and $R_8$, which are identical or different, are each chosen from linear and branched ($C_1$–$C_6$) alkyl groups substituted with at least one group chosen from nitrile groups, ester groups, acyl groups, amide groups and groups chosen from units of formulae —CO—O—$R_{13}$—D and —CO—NH—$R_{13}$—D, wherein $R_{13}$ is chosen from alkylene groups and D is a quaternary ammonium group;

$A_1$ and $B_1$ which are identical or different, are each chosen from linear and branched, saturated and unsaturated ($C_2$–$C_{20}$) polyalkylene groups, wherein said ($C_2$–$C_{20}$) polyalkylene groups optionally contain, linked to or intercalated in the main chain, at least one entity chosen from aromatic rings, oxygen atoms, sulfur atoms, sulfoxide groups, sulfone groups, disulfide groups, amino groups, alkylamino groups, hydroxyl groups, quaternary ammonium groups, ureido groups, amide groups, and ester groups; and $A_1$, $R_5$, and $R_7$ may form, together with the nitrogen atoms to which they are attached, a piperazine ring;

with the proviso that if $A_1$ is chosen from linear and branched, saturated and unsaturated ($C_2$–$C_{20}$) polyalkylene groups, and linear and branched, saturated and unsaturated hydroxy($C_2$–$C_{20}$) polyalkylene groups, $B_1$ may also be chosen from groups of formula:

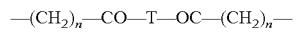

wherein n is a number ranging from 1 to 100, and T is chosen from:

a) a glycol residue of formula: —O—Z—O—, wherein Z is chosen from linear and branched hydrocarbon groups and groups chosen from formulae:

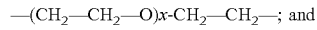

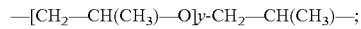

wherein x and y are identical or different and are each chosen from a number ranging from 1 to 4 representing a defined and unique degree of polymerization or an average degree of polymerization;

b) bis-secondary diamine residues;
c) bis-primary diamine residues chosen from residues of formula:
—NH—Y—NH—, wherein Y is chosen from linear and branched hydrocarbon groups, and residues of formula:

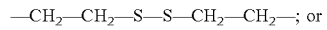

d) a ureylene group of formula: —NH—CO—NH—; and $X_1^-$ is an anion derived from mineral acids and organic acids; and compounds of formula (III):

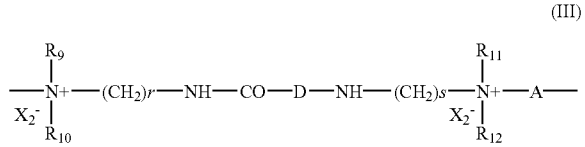

(III)

wherein:

$R_9$, $R_{10}$, $R_{11}$ and $R_{12}$, which are identical or different, are each chosen from a hydrogen atom, methyl groups, ethyl groups, propyl groups, β-hydroxyethyl groups, β-hydroxypropyl groups, and —CH$_2$CH$_2$(OCH$_2$CH$_2$)pOH groups, wherein p is chosen from 0 and integers ranging from 1 to 6;

provided that $R_9$, $R_{10}$, $R_{11}$, and $R_{12}$ are simultaneously not each a hydrogen atom;

r and s, which are identical or different, are each chosen from integers ranging from 1 to 6;

D is chosen from a direct bond and groups having formula: —(CH$_2$)q—CO— wherein q is chosen from zero and integers ranging from 1 to 34;

A is chosen from dihalide groups and a group having formula:

—CH$_2$—CH$_2$—O—CH$_2$—CH$_2$—; and $X_2^-$ is an anion derived from mineral acids and organic acids.

57. The composition according to claim 56, wherein said cationic polymers are present in an amount ranging from 0.01% to 10% by weight relative to the total weight of said composition.

58. The composition according to claim 57, wherein said cationic polymers are present in an amount ranging from 0.1% to 3% by weight relative to the total weight of said composition.

59. A composition according to claim 56, wherein said amphoteric polymers are chosen from polymers comprising randomly distributed units of K and M within their polymer chain, in which:

i)-K is chosen from groups derived from monomers containing at least one basic nitrogen group, and M is chosen from units derived from acid monomers containing at least one group chosen from carboxylic groups and sulfonic groups;

ii)-K is chosen from groups derived from carboxybetaine and sulfobetaine zwitterionic monomers, and M is chosen from groups derived from carboxybetaine and sulfobetaine zwitterionic monomers;

iii)-K and M together form a cationic polymer chain containing at least one amine group, wherein a group chosen from a carboxylic group and a sulfonic group is connected to one or more of said at least one amine groups by a hydrocarbon group, further wherein said at least one amine group is chosen from primary amine groups, secondary amine groups, tertiary amine groups, and quaternary amine groups; or iv)-K and M together form part of a polymer chain containing at least one α,β-dicarboxylic ethylene unit, wherein one of the carboxylic groups has been reacted with a polyamine unit containing at least one group chosen from primary amine groups and secondary amine groups.

60. A composition according to claim 56, wherein said amphoteric polymers are present in an amount ranging from 0.01% to 10% by weight relative to the total weight of said composition.

61. A composition according to claim 60, wherein said amphoteric polymers are present in an amount ranging from 0.05% to 5% by weight relative to the total weight of said composition.

62. A composition according to claim 61, wherein said amphoteric polymers are present in an amount ranging from 0.1% to 3% by weight relative to the total weight of said composition.

63. A composition according to claim 56, wherein said amphiphilic polymers containing at least one fatty chain are anionic polymers chosen from:

(i) polymers containing at least one hydrophilic unit and at least one allyl ether unit containing a fatty chain; and (ii) polymers containing at least one hydrophilic unit chosen from unsaturated olefinic carboxylic acids, and at least one hydrophobic unit chosen from (C$_{10}$–C$_{30}$) alkyl esters formed from unsaturated carboxylic acids and alcohols.

64. A composition according to claim 56, wherein said amphiphilic polymers containing at least one fatty chain are nonionic polymers chosen from:

(i) celluloses modified with groups containing at least one fatty chain;

(ii) hydroxypropylguars modified with groups containing at least one fatty chain;

(iii) copolymers formed from vinylpyrrolidone and fatty-chain hydrophobic monomers;

(iv) copolymers formed from at least one monomer chosen from (C$_1$–C$_6$) alkylmethacrylates and (C$_1$–C$_6$) alkyacrylates, and at least one amphiphilic monomer containing at least one fatty chain;

(v) copolymers formed from at least one monomer chosen from hydrophilic methacrylates and hydrophilic alkyacrylates, and at least one hydrophobic monomer containing at least one fatty chain;

(vi) polymers having an aminoplast ether skeleton containing at least one fatty chain; and (vii) polyurethane polyethers formed from at least one hydrophilic block and at least one hydrophobic block.

65. A composition according to claim 56, wherein said amphiphilic polymers containing at least one fatty chain are cationic polymers chosen from quatemized cellulose derivatives and polyacrylates containing acyclic amino side groups.

66. A composition according to claim 56, wherein said amphiphilic polymers are present in an amount ranging from 0.01% to 10% by weight relative to the total weight of said composition.

67. A composition according to claim 66, wherein said amphiphilic polymers are present in an amount ranging from 0.1% to 5% by weight relative to the total weight of said composition.

68. A composition according to claim 56, wherein n is a number ranging from 1 to 50.

69. A composition according to claim 56, wherein $X_1^-$ is chosen from Cl$^-$ or and Br$^-$.

70. A composition according to claim 56, wherein $X_2^-$ is a halogen atom.

71. A composition according to claim 1, wherein said composition is in the form of liquid, a cream, a gel, or any other form suitable for dyeing keratinous fibers.

72. A composition according to claim 1, wherein said composition has a pH ranging from 3 to 12.

73. A composition according to claim 72, wherein said composition has a pH ranging from 5 to 11.

74. A composition according to claim 1, further comprising at least one adjuvant chosen from anionic surfactants, cationic surfactants, nonionic surfactants, amphoteric surfactants, zwitterionic surfactants, anionic polymers, cationic polymers, nonionic polymers, amphoteric polymers, zwitterionic polymers, inorganic thickners, organic thickners, antioxidants, penetration agents, sequestering agents, fragrances, buffers, dispersants, conditioners, volatile silicones, non-volatile silicones, modified silicones, unmodified silicones, film-forming agents, ceramides, preserving agents and opacifiers.

75. A composition according to claim 1, further comprising at least one agent chosen from acidifying agents and basifying agents.

76. A composition according to claim 75, wherein said acidifying agents are chosen from mineral acids and organic acids.

77. A composition according to claim 75, wherein said basifying agents are chosen from alkanolamines, diaminoalkanes and aqueous ammonia.

78. A composition according to claim 1, wherein said keratinous fibers are human hair.

79. A process for oxidation dyeing of keratinous fibers, said process comprising:
(1) applying to said keratinous fibers, at least one composition (A) for oxidation dyeing of keratinous fibers, said composition comprising:
at least one oxidation base chosen from para-phenylenediamine derivatives containing a pyrrolidinyl group of formula (I) and their acid addition salts:

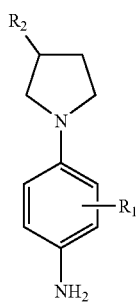

(f)

wherein:
$R_1$ is chosen from a hydrogen atom; a chlorine atom; a bromine atom; and linear and branched, saturated and unsaturated ($C_1$–$C_7$) alkyl groups, optionally substituted with at least one halogen atom, wherein at least one carbon atom is optionally replaced by an oxygen atom, a nitrogen atom, a sulfur atom or an $SO_2$ group, and when present, at least one branch of said branched groups may form at least one 3- to 6-membered ring containing at least one carbon atom, with the proviso that said $R_1$ does not comprise a group chosen from a peroxide bond, a diazo group, a nitro group, and a nitroso group; and $R_2$ is chosen from a hydroxyl group; an amino group; a group —$OR_3$, wherein $R_3$ is chosen from linear and branched ($C_1$–$C_4$) alkyls groups substituted with at least one group chosen from halogen atoms, ($C_1$–$C_2$) alkoxy groups, amino groups substituted with at least one hydroxyl group, ($C_1$–$C_2$) aminoalkyl groups substituted with at least one hydroxyl group, and ($C_3$–$C_4$) alkyl groups substituted with at least one hydroxyl group; a methylcarbonyl group; an acetamido group; and a group —$NR_4R_5$, wherein $R_4$ and $R_5$, which are identical or different, are each independently chosen from a hydrogen atom, linear and branched ($C_1$–$C_4$) alkyl groups substituted with at least one group chosen from a halogen atom, a hydroxyl group, ($C_1$–$C_2$) alkoxy groups, an amino group and ($C_1$–$C_2$) aminoalkyl groups, wherein said at least one oxidation base of formula (I) is chosen from:

N-(4-aminophenyl)-3-hydroxypyrrolidine,
N-(4-amino-2-methylphenyl)-3-hydroxypyrrolidine,
N-(4-amino-2-ethylphenyl)-3-hydroxypyrrolidine,
N-(4-amino-2-methoxyphenyl)-3-hydroxypyrrolidine,
N-(4-amino-2-(2-hydroxyethyl)phenyl)-3-hydroxypyrrolidine,
N-(4-amino-2-(1-hydroxyethyl)phenyl)-3-hydroxypyrrolidine,
N-(4-amino-2-(1,2-dihydroxyethyl)phenyl)-3-hydroxypyrrolidine,
N-(4-amino-3-methylphenyl)-3-hydroxypyrrolidine,
N-(4-amino-3-ethylphenyl)-3-hydroxypyrrolidine,
N-(4-amino-3-methoxyphenyl)-3-hydroxypyrrolidine,
N-(4-amino-3-(2-hydroxyethyl)phenyl)-3-hydroxypyrrolidine,
N-(4-amino-3-(1-hydroxyethyl)phenyl)-3-hydroxypyrrolidine,
N-(4-amino-3-(1,2-dihydroxyethyl)phenyl)-3-hydroxypyrrolidine,
N-(4-aminophenyl)-3-aminopyrrolidine,
N-(4-amino-2-methylphenyl)-3-aminopyrrolidine,
N-(4-amino-2-ethylphenyl)-3-aminopyrrolidine,
N-(4-amino-2-methoxyphenyl)-3-aminopyrrolidine,
N-(4-amino-2-(2-hydroxyethyl)phenyl)-3-aminopyrrolidine,
N-(4-amino-2-(1-hydroxyethyl)phenyl)-3-aminopyrrolidine,
N-(4-amino-2-(1,2-dihydroxyethyl)phenyl)-3-hydroxypyrrolidine,
N-(4-amino-3-methylphenyl)-3-aminopyrrolidine,
N-(4-amino-3-ethylphenyl)-3-aminopyrrolidine,
N-(4-amino-3-methoxyphenyl)-3-aminopyrrolidine,
N-(4-amino-3-(2-hydroxyethyl)phenyl)-3-aminopyrrolidine,
N-(4-amino-3-(1-hydroxyethyl)phenyl)-3-aminopyrrolidine,
N-(4-amino-3-(1,2-dihydroxyethyl)phenyl)-3-aminopyrrolidine,
N-[1-(4-Aminophenyl)pyrrolidin-3-yl]-acetamide,
[1-(4-Aminophenyl)pyrrolidin-3-yl]dimethyl-amine,
and their acid addition salts; and
(2) developing a color by applying to said keratinous fibers a composition (B), said composition comprising at least one oxidizing agent, wherein: said at least one composition (B) is combined at the time of use with said at least one composition (A), or said at least one composition (B) is applied simultaneously with or immediately after applying said at least one composition (A).

80. A process according to claim 79, wherein said composition (B) has a pH ranging from 3 to 12.

81. A process according to claim 80, wherein said composition (B) has a pH ranging from 5 to 11.

82. A process according to claim 79, wherein said keratinous fibers are hair.

83. A process for oxidation dyeing of keratinous fibers, said process comprising:
(1) applying to said keratinous fibers, at least one composition (A) for oxidation dyeing of keratinous fibers, said composition comprising:
at least one oxidation base chosen from para-phenylenediamine derivatives containing a pyrrolidinyl group of formula (I) and their acid addition salts:

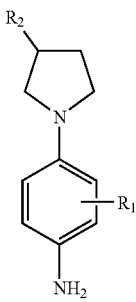

(f)

wherein:
R$_1$ is chosen from a hydrogen atom; a chlorine atom; a bromine atom; and linear and branched, saturated and unsaturated (C$_1$–C$_7$) alkyl groups, optionally substituted with at least one halogen atom, wherein at least one carbon atom is optionally replaced by an oxygen atom, a nitrogen atom, a sulfur atom or an SO$_2$ group, and when present, at least one branch of said branched groups may form at least one 3- to 6-membered ring containing at least one carbon atom, with the proviso that R$_1$ does not comprise a group chosen from a peroxide bond, a diazo group, a nitro group, and a nitroso group; and R$_2$ is chosen from a hydroxyl group; an amino group; a group —OR$_3$, wherein R$_3$ is chosen from linear and branched (C$_1$–C$_4$) alkyls groups substituted with at least one group chosen from halogen atoms, (C$_1$–C$_2$) alkoxy groups, amino groups substituted with at least one hydroxyl group, (C$_1$–C$_2$) aminoalkyl groups substituted with at least one hydroxyl group, and (C$_3$–C$_4$) alkyl groups substituted with at least one hydroxyl group; a methylcarbonyl group; an acetamido group; and a group —NR$_4$R$_5$, wherein R$_4$ and R$_5$, which are identical or different, are each independently chosen from a hydrogen atom, linear and branched (C$_1$–C$_4$) alkyl groups substituted with at least one group chosen from a halogen atom, a hydroxyl group, (C$_1$–C$_2$) alkoxy groups, an amino group and (C$_1$–C$_2$) aminoalkyl groups wherein said at least one oxidation base of formula (I) is chosen from:
N-(4-aminophenyl)-3-hydroxypyrrolidine,
N-(4-amino-2-methylphenyl)-3-hydroxypyrrolidine,
N-(4-amino-2-ethylphenyl)-3-hydroxypyrrolidine,
N-(4-amino-2-methoxyphenyl)-3-hydroxypyrrolidine,
N-(4-amino-2-(2-hydroxyethyl)phenyl)-3-hydroxypyrrolidine,
N-(4-amino-2-(1-hydroxyethyl)phenyl)-3-hydroxypyrrolidine,
N-(4-amino-2-(1,2-dihydroxyethyl)phenyl)-3-hydroxypyrrolidine,
N-(4-amino-3-methylphenyl)-3-hydroxypyrrolidine,
N-(4-amino-3-ethylphenyl)-3-hydroxypyrrolidine,
N-(4-amino-3-methoxyphenyl)-3-hydroxypyrrolidine,
N-(4-amino-3-(2-hydroxyethyl)phenyl)-3-hydroxypyrrolidine,
N-(4-amino-3-(1-hydroxyethyl)phenyl)-3-hydroxypyrrolidine,
N-(4-amino-3-(1,2-dihydroxyethyl)phenyl)-3-hydroxypyrrolidine,
N-(4-aminophenyl)-3-aminopyrrolidine,
N-(4-amino-2-methylphenyl)-3-aminopyrrolidine,
N-(4-amino-2-ethylphenyl)-3-aminopyrrolidine,
N-(4-amino-2-methoxyphenyl)-3-aminopyrrolidine,
N-(4-amino-2-(2-hydroxyethyl)phenyl)-3-aminopyrrolidine,
N-(4-amino-2-(1-hydroxyethyl)phenyl)-3-aminopyrrolidine,
N-(4-amino-2-(1,2-dihydroxyethyl)phenyl)-3-hydroxypyrrolidine,
N-(4-amino-3-methylphenyl)-3-aminopyrrolidine,
N-(4-amino-3-ethylphenyl)-3-aminopyrrolidine,
N-(4-amino-3-methoxyphenyl)-3-aminopyrrolidine,
N-(4-amino-3-(2-hydroxyethyl)phenyl)-3-aminopyrrolidine,
N-(4-amino-3-( 1-hydroxyethyl)phenyl)-3-aminopyrrolidine,
N-(4-amino-3-(1,2-dihydroxyethyl)phenyl)-3-aminopyrrolidine.
N-[1-(4-Aminophenyl)pyrrolidin-3-yl]-acetamide,
[1-(4-Aminophenyl)pyrrolidin-3-yl]dimethyl-amine.
and their acid addition salts;

(2) developing a color by applying to said keratinous fibers a composition (B), said composition comprising at least one oxidizing agent, wherein: said at least one composition (B) is combined at the time of use with said at least one composition (A) to form a combination (C);
(3) allowing said combination (C) to remain on said keratinous fibers for a time ranging from 3 to 50 minutes;
(4) rinsing said keratinous fibers;
(5) shampooing said keratinous fibers;
(6) rinsing said keratinous fibers; and
(5) drying said keratinous fibers.

84. A process according to claim 83, wherein said combination (C) is allowed to remain on said keratinous fibers for a time ranging from 5 to 30 minutes.

85. A process according to claim 83, wherein said at least one oxidizing agent is chosen from hydrogen peroxide, urea peroxide, alkali metal bromates, persalts, peracids and enzymes.

86. A process according to claim 83, wherein said composition (B) has a pH ranging from 3 to 12.

87. A process according to claim 86, wherein said composition (B) has a pH ranging from 5 to 11.

88. A process according to claim 83, wherein said keratinous fibers are hair.

89. A kit comprising at least two compartments, wherein:
(1) a first compartment comprises a composition of claim 1; and (2) a second compartment comprises, a composition (B) comprising at least one oxidizing agent.

90. A colored product formed by the oxidation of at least one oxidation base of claim 1 in the presence of at least one oxidizing agent, and optionally in the presence of at least one compound chosen from couplers and additional oxidation bases.

91. A process according to claim 79, wherein said at least one oxidizing agent is chosen from hydrogen peroxide, urea peroxide, alkali metal bromates, persalts, peracids and enzymes.

92. A compound of the following formula and its acid addition salts:

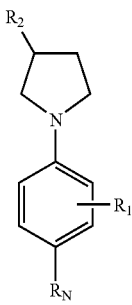

wherein:

$R_1$ is chosen from a hydrogen atom; a chlorine atom; a bromine atom; and linear and branched, saturated and unsaturated ($C_1$–$C_7$) alkyl groups, optionally substituted with at least one halogen atom, wherein at least one carbon atom is optionally replaced by an oxygen atom, a nitrogen atom, a sulfur atom or an $SO_2$ group, and, when present, at least one branch of said branched groups may form at least one 3- to 6-membered ring containing at least one carbon atom, with the proviso that said $R_1$ does not comprise a group chosen from a peroxide bond, a diazo group, a nitro group, and a nitroso group;

$R_2$ is chosen from a hydroxyl group; an amino group; a group —$OR_3$, wherein $R_3$ is chosen from linear and branched ($C_1$–$C_4$) alkyl groups substituted with at least one group chosen from halogen atoms, ($C_1$–$C_2$) alkoxy groups, amino groups substituted with at least one hydroxyl group, ($C_1$–$C_2$) aminoalkyl groups substituted with at least one hydroxyl group, and ($C_3$–$C_4$) alkyl groups substituted with at least one hydroxyl group; a methylcarbonyl group; an acetamido group; and a group —$NR_4R_5$, wherein $R_4$ and $R_5$, which are identical or different, are each independently chosen from a hydrogen atom, linear and branched ($C_1$–$C_4$) alkyl groups substituted with at least one group chosen from a halogen atom, a hydroxyl group, ($C_1$–$C_2$) alkoxy groups, an amino group and ($C_1$–$C_2$) aminoalkyl groups; and $R_N$ is chosen from —$NO_2$ and —$NH_2$, with the proviso that if $R_N$ is an amino group, $R_2$ is a hydroxy group and $R_1$ is a methyl group, then $R_1$ is not ortho to $R_N$.

93. The compound according to claim 92 where $R_N$ is —$NO_2$.

94. The compound according to claim 92 wherein the compound is:

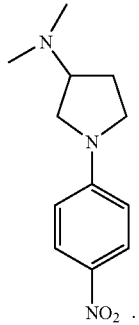

* * * * *

UNITED STATES PATENT AND TRADEMARK OFFICE
CERTIFICATE OF CORRECTION

PATENT NO. : 7,179,301 B2  Page 1 of 1
APPLICATION NO. : 09/959913
DATED : February 20, 2007
INVENTOR(S) : Laurent Vidal et al.

It is certified that error appears in the above-identified patent and that said Letters Patent is hereby corrected as shown below:

In claim 19, column 50, lines 42-43, "pyrazolo[3,2,-c]-1,2,4-triazpole," should read --pyrazolo[3,2-c]-1,2,4-triazole,--.

In claim 65, column 60, line 50, "quatemized" should read --quaternized--.

In claim 79, column 62, line 3, "alkyls" should read --alkyl--.

In claim 79, column 62, lines 27-28, "N-(4-amino-2-( 1,2-dihydroxyethyl)phenyl)-3-hydroxypyrrolidine," should read --N-(4-amino-2-(1,2-dihydroxyethyl)phenyl)-3-hydroxypyrrolidine,--.

In claim 83, column 63, line 47, "alkyls" should read --alkyl--.

In claim 83, column 63, line 61, "groups" should read --groups,--.

In claim 83, column 64, lines 31-32, "N-(4-amino-3-( 1-hydroxyethyl)phenyl)-3-aminopyrrolidine," should read --N-(4-amino-3-(1-hydroxyethyl)phenyl)-3-aminopyrrolidine,--.

In claim 83, column 64, line 36, "[1-(4-Aminophenyl)pyrrolidin-3-yl]dimethyl-amine." should read --[1-(4-Aminophenyl)pyrrolidin-3-yl]dimethyl-amine,--.

Signed and Sealed this

Twenty-fourth Day of April, 2007

JON W. DUDAS
*Director of the United States Patent and Trademark Office*